(12) United States Patent
Day et al.

(10) Patent No.: US 12,062,434 B2
(45) Date of Patent: Aug. 13, 2024

(54) SYSTEMS AND METHODS FOR RESOURCE AVAILABILITY MANAGEMENT

(71) Applicant: GE Precision Healthcare LLC, Waukesha, WI (US)

(72) Inventors: Andrew Day, Newtown, PA (US); Jeffrey Richardson Terry, Lewisville, TX (US); Siyun Hur, Hoffman Estates, IL (US); Tamas Fixler, Thornhill (CA); Mark Grum, Plymouth, MI (US); Younan Fakhouri, Des Plaines, IL (US); Gaurav Sahariya, Schaumburg, IL (US); Gabriella Devine, Chicago, IL (US); Sean Lister, Anderson, SC (US)

(73) Assignee: GE PRECISION HEALTHCARE LLC, Waukesha, WI (US)

( * ) Notice: Subject to any disclaimer, the term of this patent is extended or adjusted under 35 U.S.C. 154(b) by 388 days.

(21) Appl. No.: 17/227,221

(22) Filed: Apr. 9, 2021

(65) Prior Publication Data
US 2021/0319884 A1    Oct. 14, 2021

Related U.S. Application Data

(60) Provisional application No. 63/008,593, filed on Apr. 10, 2020.

(51) Int. Cl.
*G16H 40/20*    (2018.01)
*G06F 3/0482*    (2013.01)
(Continued)

(52) U.S. Cl.
CPC ............ *G16H 40/20* (2018.01); *G16H 10/60* (2018.01); *G16H 70/60* (2018.01); *G06F 3/0482* (2013.01)

(58) Field of Classification Search
CPC ........ G16H 40/20; G16H 70/60; G16H 10/60; G06F 3/0482
See application file for complete search history.

(56) References Cited

U.S. PATENT DOCUMENTS

| | | | | |
|---|---|---|---|---|
| 4,937,743 A | * | 6/1990 | Rassman | G06Q 10/06314 |
| | | | | 345/441 |
| 2003/0074222 A1 | * | 4/2003 | Rosow | G06Q 10/087 |
| | | | | 705/28 |

(Continued)

OTHER PUBLICATIONS

Tanei; M, Factors influencing the diagnostic accuracy of the rapid influenza antigen detection test (RIADT): a cross-sectional study, 2014, BMJ Open (Year: 2014).*

(Continued)

*Primary Examiner* — Kenneth Bartley
*Assistant Examiner* — David Choi
(74) *Attorney, Agent, or Firm* — McCoy Russell LLP

(57) ABSTRACT

Systems and methods are provided for collecting, aggregating, and visualizing resource availability information for one or more medical facilities. In one example, a method includes receiving first data from a first medical facility, the first data received via a first data streaming process and in a first format; receiving second data from a second medical facility, the second data received via a second data streaming process and in a second format; processing the first data and the second data to generate one or more resource availability graphical user interfaces (GUIs); and outputting the one or more resource availability GUIs for display on a display device.

19 Claims, 48 Drawing Sheets

(51) Int. Cl.
*G16H 10/60* (2018.01)
*G16H 70/60* (2018.01)

(56) References Cited

U.S. PATENT DOCUMENTS

| | | | | |
|---|---|---|---|---|
| 2007/0297589 | A1* | 12/2007 | Greischar | G16H 10/60 |
| | | | | 379/201.01 |
| 2014/0108035 | A1* | 4/2014 | Akbay | G06Q 10/0631 |
| | | | | 705/2 |
| 2015/0213222 | A1* | 7/2015 | Amarasingham | G16H 50/30 |
| | | | | 705/2 |
| 2016/0314432 | A1* | 10/2016 | Bhatti | G06F 16/951 |
| 2017/0039338 | A1* | 2/2017 | Khindaria | G16H 70/20 |
| 2018/0089781 | A1* | 3/2018 | Landrum | G06Q 30/0282 |
| 2018/0314802 | A1* | 11/2018 | Dreyer | G16H 40/63 |

OTHER PUBLICATIONS

Dugas; Andrea Freyer, Influenza Forecasting with Google Flu Trends, Feb. 2013. 14, PLoS One, vol. 8, Issue 2 (Year: 2013).*
Snell; Elizabeth, Healthcare Data Encryption not 'Required,' but Very Necessary, Jun. 14, 2017, Cybersecurity News (Year: 2017).*
Becker; Arielle Levin, AG: Hartford Hospital, contractor to pay $90,000 in 2012 data theft, Nov. 6, 2015, CT Mirror (Year: 2015).*
HITE-CT Board, Health Information Technology Exchange of Connecticut, Nov. 21, 2011, ct.gov (Year: 2011).*
Jones; Elysa, Emergency Data Exchange Language (EDXL) Hospital Availability Exchange (HAVE) Version 2.0, Mar. 18, 2019, OASIS (Year: 2019).*
How to configure Import from Flat File (CSV) from the Controller application server, Jun. 15, 2018, IBM Support (Year: 2018).*
EDI Format, Mar. 2009, Stack Overflow (Year: 2009).*

* cited by examiner

Configurable Thresholds ⟵ 1120

| Variable | Default | Definition |
|---|---|---|
| X | 14 days | time period in which a negative resulted patient may still become positive (incubation period) |
| Y | 5 days | waiting time after first post positive NEG in which a patient must remain asymptomatic before being considered to be recovered |
| Z | 24 hours | minimum time between 2 successive post positive negatives required to consider a patient to be clear |

PATIENT IS POSITIVE

| n-2+ most recent positive 1122 | | prior result | | T(cur)-T(prior) 1124 | current result 1126 | | Designation |
|---|---|---|---|---|---|---|---|
| >Y ago | <Y ago | >Y ago | <Y ago | >Z | >Y ago | <Y ago | |
| | Any or no values here - doesn't matter | | | | | Positive | CV19 + |
| | | Positive | | | Positive | | CV19 + |
| | | Positive | | | Negative | | drop from tile |
| | | Positive | | | Inconclusive | | CV19 + |
| | | Positive | Positive | | | Negative | PUI-NEG* |
| | | | Positive | | | Inconclusive | CV19 + |
| | | | | | | Negative | PUI-NEG* |
| | | | | | | Inconclusive | CV19 + |
| Positive | | Negative | | Y | Negative | | drop from tile |
| Positive | | Negative | | Y | | Negative | drop from tile |
| Positive | | Negative | | N | Negative | | drop from tile |
| Positive | | Negative | | N | | Negative | drop from tile |
| Positive | | Inconclusive | | Y | Negative | | drop from tile |
| Positive | | Inconclusive | | Y | | Negative | PUI-NEG* |
| Positive | | Inconclusive | | N | Negative | | drop from tile |
| Positive | | Inconclusive | | N | | Negative | PUI-NEG* |
| | Positive | | Negative | Y | Negative | | drop from tile |
| | Positive | | Negative | Y | | Negative | PUI-NEG* |
| | Positive | | Inconclusive | Y | | Inconclusive | CV19 + |
| | Positive | | Inconclusive | Y | | Negative | PUI-NEG* |

| Variable | Default | Definition |
|---|---|---|
| X | 14 days | ited patient may still become positive (incubation period) |
| Y | 5 days | atient must remain asymptomatic before being considered to be recovered |
| Z | 24 hours | st positive negatives required to consider a patient to be clear |

NEVER PREVIOUSLY POSITIVE

| n-2 prior result | | prior result | | current result | | Designation |
|---|---|---|---|---|---|---|
| >X ago | <X ago | >X ago | <X ago | >X ago | <X ago | |
| | | | | | Inconclusive | PUI-NEG |
| | | | | Inconclusive | | drop from tile |
| | | | | | Negative | PUI-NEG |
| | | | | Negative | | drop from tile |
| | | Inconclusive | | | Inconclusive | PUI-NEG |
| | | Inconclusive | | Inconclusive | | drop from tile |
| | | Inconclusive | | | Negative | PUI-NEG |
| | | Inconclusive | | Negative | | drop from tile |
| | | Negative | Inconclusive | | | PUI-NEG |
| | | Negative | Inconclusive | | | PUI-NEG |
| | | Negative | | | Inconclusive | drop from tile |
| | | Negative | | | Negative | drop from tile |
| | | Negative | | Inconclusive | | drop from tile |
| | | Negative | | Negative | | drop from tile |
| | | Negative | Negative | | | PUI-NEG |
| | | Negative | Negative | | | PUI-NEG |
| | | Negative | | | Inconclusive | drop from tile |
| | | Negative | | Inconclusive | | drop from tile |
| | | Negative | | | Negative | drop from tile |
| | | Negative | | Negative | | drop from tile |
| Negative | | Negative | | | Inconclusive | drop from tile |
| Negative | | Negative | | Inconclusive | | drop from tile |
| Negative | | Negative | | | Negative | drop from tile |
| Negative | | Negative | | Negative | | drop from tile |
| Inconclusive | | Negative | | | Inconclusive | drop from tile |
| Inconclusive | | Negative | | Inconclusive | | drop from tile |
| Inconclusive | | Negative | | | Negative | drop from tile |
| Inconclusive | | Negative | | Negative | | drop from tile |
| Negative | | Inconclusive | | | Inconclusive | drop from tile |
| Negative | | Inconclusive | | Inconclusive | | drop from tile |
| Negative | | Inconclusive | | | Negative | drop from tile |
| Negative | | Inconclusive | | Negative | | drop from tile |
| Inconclusive | | Inconclusive | | | Inconclusive | PUI-NEG |
| Inconclusive | | Inconclusive | | Inconclusive | | drop from tile |
| Inconclusive | | Inconclusive | | | Negative | PUI-NEG |
| Inconclusive | | Inconclusive | | Negative | | drop from tile |

1142  1144

| Hospital critical resources | CFD north | | Deland | | | Waterman | | | Fish memorial | | | Palm coast | | |
|---|---|---|---|---|---|---|---|---|---|---|---|---|---|---|
| Grouping adult | UNOCC | OCC | UNOCC | CAP NP | CENSUS OCC | UNOCC | CAP NP | CENSUS OCC | UNOCC | CAP NP | CENSUS OCC | UNOCC | CAP NP | CENSUS OCC |
| All | 465 | 84 % | 140 | 578 8/50 | 438 76 % | 132 | 1091 5/65 | 959 88 % | 71 | 444 6/30 | 373 84 % | 122 | 878 4/52 | 756 86 % |
| Adult ICU | 96 | 82 % | 42 | 98 0/20 | 56 57 % | 23 | 212 2/24 | 189 92 % | 10 | 80 0/10 | 70 90 % | 21 | 148 1/10 | 127 89 % |
| Adult PCU | 90 | 83 % | 75 | 440 6/25 | 365 83 % | 7 | 36 1/5 | 29 84 % | - | - - | - % | 8 | 49 1/10 | 41 87 % |
| Adult MT/MS | 240 | 87 % | 19 | 24 0/0 | 5 21 % | 90 | 813 1/33 | 723 92 % | 52 | 344 2/15 | 292 88 % | 79 | 656 2/30 | 577 91 % |
| Adult OBS | 39 | 57 % | 4 | 16 2/5 | 12 75 % | 12 | 30 1/3 | 18 40 % | 9 | 20 4/5 | 11 45 % | 14 | 25 0/2 | 11 44 % |
| Adult negative pressure | 16 | 94 % | 8 | 50 | 42 84 % | 5 | 65 | 60 92 % | 6 | 30 | 24 80 % | 4 | 52 | 48 92 % |
| Ventilators | 102 | 471 | 41 | 221 | 180 81 % | 8 | 90 | 82 91 % | 34 | 130 | 96 74 % | 19 | 90 | 71 79 % |

| Hospital critical resources — Region | CFD north UNOCC \| OCC | Deland UNOCC\|CAP CENSUS NP \| \_ OCC | Waterman UNOCC\|CAP CENSUS NP \| \_ OCC | Fish memorial UNOCC\|CAP CENSUS NP \| \_ OCC | Palm coast UNOCC\|CAP CENSUS NP \| \_ OCC |
|---|---|---|---|---|---|
| All | 465 \| 84 % | 140 \| 578   438 / 8 | 132 \| 1091  959 / — | 71 \| 444   373 / 6/30  ○ 84 % | 122 \| 878   756 / 4/52  ○ 86 % |
| Adult ICU | 96 \| 82 % | 42 \| —   — / 0/— | — | 10 \| 80   70 / 0/10  ⓐ 90 % | 21 \| 148   127 / 1/10  ○ 89 % |
| Adult PCU | 90 \| 83 % | 75 \| —   — / 6/— | — | — \| —   — / —  — % | 8 \| 49   41 / 1/10  ○ 87 % |
| Adult MT/MS | 240 \| 87 % | 19 \| —   — / 0 | — | 52 \| 344   292 / 2/15  ○ 88 % | 79 \| 656   577 / 2/30  ⓐ 91 % |
| Adult OBS | 39 \| 57 % | 4 \| —   — / — | — | 9 \| 20   11 / 4/5  ○ 45 % | 14 \| 25   11 / 0/2  ○ 44 % |
| Adult negative pressure | 16 \| 94 % | 2 \| —   — / — | 8 \| 90   — | 6 \| 30   24 / —  ○ 80 % | 4 \| 52   48 / —  ⓐ 92 % |
| Ventilators | 102 \| 471 | 41 \| 221   180 / —  ○ 81 % | 82   ⓐ 91 % | 34 \| 130   96 / —  ○ 74 % | 19 \| 90   71 / —  ○ 79 % |

Vents in use: 82

| Bed | Serial no. | Time in use |
|---|---|---|
| PD12-4 | 5465465 | 3d 23h 30m |
| PD12-5 | 6756456 | 3d 19h 52m |
| PD12-7 | 3546656 | 2d 22h 27m |
| PD12-8 | 4546556 | 2d 19h 22m |
| PD12-11 | 4546546 | 2d 18h 45m |
| PD12-14 | 4456555 | 2d 18h 24m |

1800, 1802, 1804

Hospital critical resources — Facility: Lakeside

| | CENSUS | OCC | UNOCC | NEG pressure IN USE | UNOCC | DC Orders | TX orders | Blocked |
|---|---|---|---|---|---|---|---|---|
| All | 466 | 90% | 53 | 54 | 10 | 17 | 12 | 13 |
| Adult ICU | 22 | 92% | 2 | 2 | 2 | 0 | 2 | 2 |
| Adult PCU | 15 | 94% | 1 | 2 | 1 | 0 | 1 | 0 |
| Adult MT/MS | 228 | 95% | 12 | 5 | 1 | 11 | 6 | 4 |
| Adult OBS | 28 | 80% | 7 | 1 | 0 | 4 | 1 | 2 |
| Peds ICU | 26 | 93% | 2 | 18 | 2 | 0 | 1 | 3 |
| Peds PCU | 10 | 83% | 2 | 1 | 1 | 0 | 0 | 0 |
| Peds MT/MS | 48 | 83% | 10 | 6 | 2 | 1 | 1 | 0 |
| Peds OBS | 24 | 80% | 6 | 0 | 1 | 1 | 0 | 0 |
| Specialty | 65 | 86% | 11 | 0 | 0 | 0 | 0 | 2 |

FIG. 19

Hospital critical resources — Lakeside

| Unit | CENSUS ICU/PCU | OCC | UNOCC | NEG pressure IN USE / UNOCC | DC Orders | TX orders | Blocked |
|---|---|---|---|---|---|---|---|
| Adult MT/MS | 228 | | 12 | 5 / 1 | 11 | 7 | 4 |
| 5 North | 14 / 0 / 1 | 93% | 1 | 1 / 0 | 0 | 2 | 0 |
| 7 North | 27 / 0 / 0 | 90% | 3 | 1 / 1 | 2 | 0 | 2 |
| 10 East | 20 / 0 / 1 | 100% | 0 | 2 / 0 | 0 | 1 | 0 |
| 11A | 29 / 1 / 2 | 97% | 1 | 0 / 0 | 2 | 0 | 0 |
| 11C | 26 / 0 / 0 | 96% | 1 | 0 / 0 | 1 | 1 | 0 |
| 13B | 28 / 2 / 1 | 93% | 2 | 1 / 0 | 2 | 2 | 1 |
| 14A | 30 / 1 / 1 | 100% | 0 | 0 / 0 | 3 | 0 | 0 |
| 14B | 29 / 0 / 2 | 97% | 1 | 0 / 0 | 6 | 0 | 1 |
| 16A | 25 / 0 / 0 | 89% | 3 | 0 / 0 | 6 | 1 | 0 |

FIG. 21

| Census | All beds | | Adult | | | | PEDS | | | | Vents | | Covid | |
|---|---|---|---|---|---|---|---|---|---|---|---|---|---|---|
| Unocc Ca... | | ICU | IMC | Acute | OBS | ICU | IMC/Acute | OBS | In use | | PUI | CV19+ |
| Total 240 | 94,273 82% | 94,273 82% | 57,114 85% | 432,254 86% | 34,067 81% | 16,853 81% | 16,208 83% | 19,837 79% | 57,974 81% | | 1,114,944 | 124,217 |
| ⚠ Northeast | 15,569 90% | 15,569 90% | 10,566 93% | 75,936 89% | 5,352 76% | 3,427 90% | 29,763 91% | 3,442 81% | 10,585 90% | | 666,738 | 74,082 |
| D1: New England > | 3,411 82% | 3,411 82% | 2,428 87% | 17,664 84% | 894 51% | 365 76% | 6,366 79% | 785 75% | 1,952 76% | | 59,904 | 6,656 |
| 🔴 D2: Mid Atlantic > | 12,158 92% | 12,158 92% | 8,138 95% | 58,272 91% | 4,448 83% | 3,062 92% | 23,397 95% | 2,657 83% | 8,633 94% | | 606,834 | 67,426 |
| Midwest | 172,275 82% | 19,375 80% | 12,084 83% | 91,643 84% | 7,432 81% | 3,453 82% | 33,883 81% | 4,403 80% | 12,562 86% | | 125,529 | 13,948 |
| D3: East N. Central > | 115,464 83% | 13,375 82% | 8,158 84% | 60,765 84% | 5,064 84% | 2,339 81% | 22,428 81% | 2,990 83% | 9,017 87% | | 106,533 | 11,837 |
| D4: West N. Central> | 56,810 81% | 5,654 76% | 3,926 79% | 30,878 83% | 2,369 77% | 1,115 83% | 11,455 81% | 1,413 76% | 3,545 83% | | 18,996 | 2,111 |
| South | 349,335 82% | 40,110 79% | 24,558 83% | 185,903 84% | 14,881 81% | 7,153 79% | 68,185 81% | 8,546 77% | 21,615 71% | | 184,203 | 20,467 |
| D5: South Atlantic > | 155,932 86% | 17,833 83% | 10,992 87% | 83,370 88% | 6,557 83% | 2,953 83% | 30,399 83% | 3,822 80% | 10,238 76% | | 95,391 | 10,599 |
| D6: East S. Central > | 99,660 80% | 11,366 77% | 7,037 82% | 53,313 83% | 4,257 79% | 2,131 77% | 19,211 78% | 2,344 73% | 6,268 73% | | 29,421 | 3,269 |
| D7: West S. Central> | 93,744 80% | 10,910 76% | 6,529 80% | 49,221 81% | 4,066 80% | 2,064 75% | 18,574 79% | 2,380 78% | 5,110 62% | | 59,391 | 6,599 |
| West | 148,942 85% | 19,220 85% | 9,906 83% | 78,772 88% | 6,402 86% | 2,819 76% | 28,377 82% | 3,446 77% | 11,540 79% | | 138,474 | 15,386 |
| D8: Mountain > | 45,841 81% | 5,816 81% | 3,140 81% | 23,800 82% | 1,848 76% | 962 75% | 9,148 82% | 1,128 76% | 3,339 76% | | 43,038 | 4,782 |
| ⚠ D9: Pacific > | 103,101 87% | 13,404 87% | 6,766 84% | 54,972 91% | 4,554 90% | 1,858 76% | 19,229 83% | 2,318 76% | 8,202 81% | | 95,436 | 10,604 |

| Census | Unocc | Ca... | All beds | Adult ICU | Adult IMC | Adult Acute | Adult OBS | PEDS ICU | PEDS IMC/Acute | PEDS OBS | Vents In use | Covid PUI | Covid CV19+ |
|---|---|---|---|---|---|---|---|---|---|---|---|---|---|
| > | Total | | 814,606 84% | 94,273 82% | 57,114 85% | 432,254 86% | 34,067 81% | 16,853 81% | 16,208 83% | 19,837 79% | 57,974 81% | 1,114,944 | 124,217 |
| ▽ | Northeast | | 144,055 89% | 15,569 90% | 10,566 93% | 75,936 89% | 5,352 76% | 3,427 90% | 29,763 91% | 3,442 81% | 10,585 90% | 666,738 | 74,082 |
|  | D1: New England > | | 31,912 81% | 3,411 82% | 2,428 87% | 17,664 84% | 894 51% | 365 76% | 6,366 92% | 785 95% | 1,952 76% | 59,904 | 6,656 |
|  | D2: Mid Atlantic ∨ | | 112,142 92% | 12,158 92% | 8,138 95% | 58,272 91% | 4,448 83% | 3,062 92% | 23,397 95% | 2,657 83% | 8,633 94% | 606,834 | 67,426 |
| ▽ | New jersey > | | 21,830 90% | 2,595 88% | 1,580 95% | 11,230 90% | 832 80% | 538 88% | 4,544 95% | 512 82% | 1,823 93% | 100,116 | 11,124 |
| ▽ | New York > | | 52,683 93% | 5,546 94% | 3,827 97% | 27,226 92% | 2,195 89% | 1,642 94% | 11,004 97% | 1,243 84% | 3,980 95% | 481,032 | 53,448 |
|  | NY Presbyterian | | 2,566 97% | 257 97% | 133 100% | 1,323 96% | 76 95% | 201 95% | 530 100% | 47 88% | 185 95% | 532 | 390 |
|  | NYU langone | | 1,585 97% | 155 95% | 79 96% | 830 98% | 48 99% | 125 96% | 319 98% | 29 90% | 111 93% | 372 | 211 |
| ⊙ | Long island jewish | | 1,500 97% | 152 98% | 77 100% | 773 96% | 44 94% | 118 95% | 310 100% | 26 85% | 109 95% | 297 | 209 |
| ⊙ | Montefiore | | 1,522 100% | 153 100% | 76 100% | 795 100% | 46 100% | 116 95% | 306 100% | 30 97% | 110 96% | 476 | 204 |
| △ | Mount sinai NY | | 1,121 93% | 109 92% | 55 78% | 586 86% | 33 78% | 88 84% | 228 89% | 22 100% | 78 81% / 52 97% | 257 | 152 |
| △ | Buffalo general | | 788 74% | 73 68% | 40 74% | 376 68% | 31 97% | 64 75% | 188 88% | 15 70% | 52 97% | 157 | 110 |
| △ | North shore LIJ | | 1,008 97% | 98 94% | 50 97% | 530 98% | 31 99% | 75 90% | 204 98% | 20 95% | 70 95% | 128 | 142 |
|  | NYC belleview | | 891 98% | 88 97% | 64 100% | 465 98% | 27 97% | 68 93% | 181 99% | 17 95% | 64 91% | 176 | 134 |

FIG. 25

| | | | | Adult | | | | PEDS | |
|---|---|---|---|---|---|---|---|---|---|
| USA | Census | Unocc | Ca... | ICU | IMC | Acute | OBS | ICU | IMC/Acute |
| | All beds | | | | | | | | |
| Total | 814,606 | | | 94,273 | 57,114 | 432,254 | 34,067 | 16,853 | 16,208 |
| | 84% | | | 82% | 85% | 86% | 81% | 81% | 83% |
| ⚠ Northeast | 144,055 | | | 15,569 | 10,566 | 75,936 | 5,352 | 3,427 | 29,763 |
| | 89% | | | 90% | 93% | 89% | 76% | 90% | 91% |
| D1: New England > | 31,912 | | | 3,411 | 2,428 | 17,664 | 894 | 365 | 6,366 |
| | 81% | | | 82% | 87% | 84% | 51% | 76% | 92% |
| ⚠ D2: Mid Atlantic ∨ | 112,142 | | | 12,158 | 8,138 | 58,272 | 4,448 | 3,062 | 23,397 |
| | 92% | | | 92% | 95% | 91% | 83% | 92% | 95% |
| ⚠ New jersey > | 21,830 | | | 2,595 | 1,580 | 11,230 | 832 | 538 | 4,544 |
| | 90% | | | 88% | 95% | 90% | 80% | 88% | 95% |
| ⚠ New York ∨ | 52,683 | | | 5,546 | 3,827 | 27,226 | 2,195 | 1,642 | 11,004 |
| | 93% | | | 94% | 97% | 92% | 89% | 94% | 97% |
| ⚠ NY Presbyterian | 2,566 | | | 257 | 133 | 1,323 | 76 | 201 | 530 |
| | 97% | | | 97% | 100% | 96% | 95% | 95% | 100% |
| ⚠ NYU langone | 1,585 | | | 155 | 79 | 830 | 48 | 125 | 319 |
| | 97% | | | 95% | 96% | 98% | 99% | 96% | 98% |
| ⚠ Long island jewish | 1,500 | | | 152 | 77 | 773 | 44 | 118 | 310 |
| | 97% | | | 98% | 100% | 96% | 94% | 95% | 100% |
| ⚠ Montefiore | 1,522 | | | 153 | 76 | 795 | 46 | 116 | 306 |
| | 100% | | | 100% | 100% | 100% | 100% | 95% | 100% |
| ⚠ Mount sinai NY | 1,121 | | | 109 | 55 | 586 | 33 | 88 | 228 |
| | 97% | | | 94% | 78% | 86% | 78% | 84% | 89% |
| ⚠ Buffalo general | 788 | | | 73 | 40 | 376 | 31 | 64 | 188 |
| | 74% | | | 68% | 74% | 68% | 97% | 75% | 88% |
| ⚠ North shore LIJ | 1,008 | | | 98 | 50 | 530 | 31 | 75 | 204 |
| | 97% | | | 94% | 97% | 98% | 99% | 90% | 98% |
| ⚠ NYC belleview | 891 | | | 88 | 64 | 465 | 27 | 68 | 181 |
| | 98% | | | 97% | 100% | 98% | 97% | 93% | 99% |

— 2600

Super capacity — 2602
National by state — 2604
MSA ● State — 2606

⚙ Settings

Expanded sections - read only, adjust on tile — 2608

| Region | Division | State | Facility |
|---|---|---|---|
| N | D2 | NY | NY presb... |
| N | D2 | NY | NYU lang... |
| N | D2 | NY | Long islan... |
| N | D2 | NY | Montefiore |
| N | D2 | NY | Mount sin... |
| N | D2 | NY | Buffalo ge... |
| N | D2 | NY | North sho... |
| N | D2 | NY | NYC belle... |

Sorting Clear all

Field — Sort by — Ascending / desce...
All — All beds count ⊕ — Descending ⊕

Filters

Alert level ⊕ — 2616 — AND OR — 2612 / 2614
— Remove filter — 2610
Select all / select none — 2618

Options
☑ ⚠ Critical
☑ ⚠ Warning
☑ ⚠ No alert
☑ ⚠ Beds available
— 2620

Save settings — 2622 — Reset — 2624 — Cancel — 2626 — + Add filter
Apply — 2628

FIG. 26

| Census | Unocc | Ca... | All beds | | | Adult | | | | PEDS | |
|---|---|---|---|---|---|---|---|---|---|---|---|
| | | | | ICU | IMC | Acute | OBS | ICU | IMC/Acute | | |
| Total | > | 814,606 84% | 94,273 82% | 57,114 85% | 432,254 86% | 34,067 81% | 16,853 81% | 16,208 83% | | | |
| △ Northeast | > | 144,055 89% | 15,569 90% | 10,566 93% | 75,936 89% | 5,352 76% | 3,427 90% | 29,763 91% | | | |
| D1: New England | > | 31,912 81% | 3,411 82% | 2,428 87% | 17,664 84% | 894 51% | 365 76% | 6,366 92% | | | |
| ⊘ D2: Mid Atlantic | > | 112,142 92% | 12,158 92% | 8,138 95% | 58,272 91% | 4,448 83% | 3,062 92% | 23,397 95% | | | |
| ⊘ New jersey | > | 21,830 90% | 2,595 88% | 1,580 95% | 11,230 90% | 832 80% | 538 88% | 4,544 95% | | | |
| ⊘ New York | > | 52,683 93% | 5,546 94% | 3,827 97% | 27,226 92% | 2,195 89% | 1,642 94% | 11,004 97% | | | |
| ⊘ NY Presbyterian | | 2,566 97% | 257 97% | 133 100% | 1,323 96% | 76 95% | 201 95% | 530 100% | | | |
| ⊘ NYU langone | | 1,585 97% | 155 95% | 79 96% | 830 98% | 48 99% | 125 96% | 319 98% | | | |
| ⊘ Long island jewish | | 1,500 97% | 152 98% | 77 100% | 773 96% | 44 94% | 118 95% | 310 100% | | | |
| ⊘ Montefiore | | 1,522 100% | 153 100% | 76 100% | 795 100% | 46 100% | 116 95% | 306 100% | | | |
| ⊘ Mount sinai NY | | 1,121 97% | 109 94% | 55 78% | 586 86% | 33 78% | 88 84% | 228 89% | | | |
| ⊘ Buffalo general | | 788 74% | 73 68% | 40 74% | 376 68% | 31 97% | 64 75% | 188 88% | | | |
| ⊘ North shore LIJ | | 1,008 97% | 98 94% | 50 97% | 530 98% | 31 99% | 75 90% | 204 98% | | | |
| NYC belleview | | 891 98% | 88 97% | 64 100% | 465 98% | 27 97% | 68 93% | 181 99% | | | |

Settings — 2602

Expanded sections - read only, adjust on tile — 2606

| Region | Division | State | Facility |
|---|---|---|---|
| N | D2 | NY | NY presb... |
| N | D2 | NY | NYU lang... |
| N | D2 | NY | Long islan... |
| N | D2 | NY | Montefiore |
| N | D2 | NY | Mount sin... |
| N | D2 | NY | Buffalo ge... |
| N | D2 | NY | North sho... |
| N | D2 | NY | NYC belle... |

Sorting  Clear all

| Field | Sort by | Ascending / desce... |
|---|---|---|
| All | All beds count ◆ | Descending ◆ |

Filters

Alert level — 2616 — Remove filter — AND | OR — 2610

Select all / select none

Options
- ☑ ◆ Critical
- ☐ △ Warning — 2618
- ☐ □ No alert — 2702
- ☑ △ Beds available — 2704

+ Add filter

Save settings  Reset  Cancel  Apply

FIG. 27

| Census | All beds | | ICU | | IMC | | Adult Acute | | OBS | | ICU | | PEDS IMC/Acute | | OBS | | Vents In use | | Covid PUI | CV19+ |
|---|---|---|---|---|---|---|---|---|---|---|---|---|---|---|---|---|---|---|---|---|
| Total | 814,606 | 84% | 94,273 | 82% | 57,114 | 85% | 432,254 | 86% | 34,067 | 81% | 16,853 | 81% | 16,208 | 83% | 19,837 | 79% | 57,974 | 81% | 1,114,944 | 124,217 |
| Northeast | 144,055 | 89% | 15,569 | 90% | 10,566 | 93% | 75,936 | 89% | 5,352 | 76% | 3,427 | 90% | 29,763 | 91% | 3,442 | 81% | 10,585 | 90% | 666,738 | 74,082 |
| D1: New England | 31,912 | 81% | 3,411 | 82% | 2,428 | 87% | 17,664 | 84% | 894 | 51% | 365 | 76% | 6,366 | 79% | 785 | 95% | 1,952 | 76% | 59,904 | 6,656 |
| D2: Mid Atlantic | 112,142 | 92% | 12,158 | 92% | 8,138 | 95% | 58,272 | 91% | 4,448 | 83% | 3,062 | 92% | 23,397 | 95% | 2,657 | 83% | 8,633 | 94% | 606,834 | 67,426 |
| New Jersey | 21,830 | 90% | 2,595 | 86% | 1,580 | 95% | 11,230 | 90% | 832 | 80% | 538 | 88% | 4,544 | 95% | 512 | 82% | 1,823 | 93% | 100,116 | 11,124 |
| New York | 52,683 | 93% | 5,546 | 94% | 3,827 | 97% | 27,226 | 92% | 2,195 | 89% | 1,642 | 94% | 11,004 | 97% | 1,243 | 84% | 3,980 | 95% | 481,032 | 53,448 |
| NY Presbyterian | 2,566 | 97% | 257 | 97% | 133 | 100% | 1,323 | 96% | 76 | 95% | 201 | 95% | 530 | 100% | 47 | 88% | 185 | 95% | 532 | 390 |
| NYU langone | 1,585 | 97% | 155 | 95% | 79 | 96% | 830 | 98% | 48 | 99% | 125 | 96% | 319 | 98% | 29 | 90% | 111 | 93% | 372 | 211 |
| Long Island jewish | 1,500 | 97% | 152 | 98% | 77 | 100% | 773 | 96% | 44 | 94% | 118 | 95% | 310 | 100% | 26 | 85% | 109 | 95% | 297 | 209 |
| Montefiore | 1,522 | 100% | 153 | 100% | 76 | 100% | 795 | 100% | 46 | 100% | 116 | 95% | 306 | 100% | 30 | 97% | 110 | 96% | 476 | 204 |
| Buffalo general | 788 | 74% | 73 | 68% | 40 | 74% | 376 | 68% | 31 | 72% | 64 | 75% | 188 | 88% | 15 | 70% | 52 | 64% | 157 | 110 |
| Upstate university | 551 | 75% | 76 | 69% | 32 | 74% | 191 | 74% | 33 | 78% | 87 | 84% | 110 | 72% | 22 | 78% | 59 | 64% | 118 | 93 |
| Saratoga | 132 | 77% | 15 | 68% | 18 | 97% | 45 | 98% | 12 | 99% | 11 | 90% | 23 | 98% | 8 | 95% | 22 | 63% | 63 | 31 |
| White plains | 213 | 76% | 20 | 97% | 23 | 100% | 110 | 98% | 14 | 97% | 12 | 93% | 24 | 99% | 10 | 95% | 34 | 61% | 52 | 42 |

FIG. 28

Infectious: Covid-19  — 2908

Patient Load — 2910  
In test 24  PUI 7  CV19+6  Vents 10

| Unit | Loc | Patients under INV Intest NEG(PUI) | | CV19+ | Vents |
|---|---|---|---|---|---|
| | | Intest | NEG(PUI) | | |
| 10 EAST | Med Surg | 9 | 2 | (1) 4 | 4 |
| 9 EAST | Med Surg | 4 | 1 | - | 1 |
| 9 WEST | Med Surg | 6 | 2 | - | 1 |
| CV19 OBS | Med Surg | 3 | 1 | (2) | 4 |
| ED | ED | 2 | 1 | - | - |

2912

Patient activity (new tests ordered, new CV19 POS) — 2914

Tests ☐ Ordered ☐ Projected | New CV19+ patients ☒ Confirmed ☐ Pr...

(bar chart 2/28 – 3/11, Today marker)

2916

Status of cc & CV targeted beds   Avail: CC0  CC W CV 3  CC W CV 7 — 2902 2904 2906 2918

| Unit | In use(CV) | Avail(CV) | Crit not met | Vents | Bed blocked |
|---|---|---|---|---|---|
| MICU | 11(1) | 1(1) | 2 | 8 | |
| CVICU | 7(2) | 1(1) | 3 | 2 | 2 |
| PCU | 15(3) | 1(1) | 1 | 4 | |
| 8200 | (18) | (6) | 4 | - | |
| 7N-NP | (4) | (1) | 2 | 1 | |

EVS for CC+CV targeted beds   Avail: CC1  CCWCV1  CV2 — 2924

| Priority | EVS | Bed status | Next patient | Locations |
|---|---|---|---|---|
| Stat | △ | H✓ 7N-11 | C.WIL 925041995 | 7NSI-15 |
| Stat | △ | H✓ MICU-10 | O.ADA 743709031 | ED |
| | ⚇ | PCU2-13 [2] | | |
| | 📇 | H✓ CVICU5-3 | J.LEE 622716296 | Transf |

Infectious: Covid-19     Lakeside ⟩ ⓘ ⚙

Patient Load — 3000

| Unit | Loc | In test 24 | PUI 7 | CV19+6 | | |
|---|---|---|---|---|---|---|
| | | Patients under INV Intest NEG(PUI) | | CV19+ | Location | |
| 10 EAST | Med Surg | 9 | | 2 ⓘ 4 | 10E-7, 10E-13, 10E-... | |
| 9 EAST | Med Surg | 4 | | 1 | CV19 POS 4 | |
| 9 WEST | Med Surg | 6 | | 2 | 10 East | |
| CV19 OBS | Med Surg | 3 | | 1 | Patient Bed | |
| ED | ED | 2 | | 1 | C.DAN 674251 10E-7 | |
| | | | | | B.SAP 669979 10E-13 | |
| | | | | | A.DAY 666222 📧 10E-19 | 3008 |
| | | | | | R.MAY 667203 10E-21 | |

3002  3004

Status of CC&CV targeted beds     Avail: CC0  CC W CV 3  CV7

| Unit | In use(CV) | Avail(CV) | Crit not met | Blocked beds |
|---|---|---|---|---|
| MICU | 11(1) | 1(1) | MIC-3, MIC-7 | |
| U | 7(2) | 1(1) | | |
| U | 15(3) | 1(1) | PCU-5, PCU-8, PCU-9, PCU-10... | |
| 00 | (18) | (6) | | 2 |
| -NP | (4) | (1) | | |
| 1d | | | | |

Daily patient count — 3006

Tests ☐ Ordered     New CV19+ patients ☒ Confirmed
      ☒ Projected                     ☐ Projected
                                      Today

[Bar chart: 2/28, 3/1, 3/3, 3/5, 3/7, 3/9, 3/11 — y-axis 0, 5, 10, 15, 20, 25]

EVS for CC+CV targeted beds     Avail: CC1  CC W CV 1  CV2

| Priority | EVS | Bed status | Next patient | Locations |
|---|---|---|---|---|
| Stat | 🔺 | (H✓) 7N-11 | C.WIL 925041995 | 7NSI-15 |
| Stat | 🔺 | (H✓) MICU-10 | O.ADA 743709031 | ED |
| | 🛋 | PCU2-13 [2] | | |
| | 🛋 | CVICU5-3 | J.LEE 622716296 | Transf |

FIG. 30

Infectious: Covid-19 — Facility edition

Current patients: Test 11    NEG 5    CV19 9      Avail: CC 11    NP 11

Patient Load

| Unit | Loc | In test | NEG(PUI) | CV19+ | Location |
|---|---|---|---|---|---|
| ESCCU1 | ICU | 1 | 0 | 2 | CCU1-2, CCU1-1 |
| ESMED1 | Medicine | 1 | 4 | 1 | MED1-14 |
| ESMED5 | Medicine | 3 | 0 | 2 | MED5-2, MED5-5 |
| ESMED6 | Medicine | 2 | 0 | 1 | MED6-18 |
| ESMICU1 | ICU | 4 | 1 | 3 | MICU1-8, MICU1-9 |

Critical care + NP beds

| Unit | Census | Avail | Criteria not met | Beds blocked |
|---|---|---|---|---|
| ESMED5 | 28(4) | 1 | | 0 |
| ESMED6 | 20(6) | 1(1) | | 1 |
| ESMED7 | 42(3) | 0 | | 1 |
| ESMICU1 | 23(17) | 1(1) | MICU1-1, MICU1-4 | 0 |
| ESNCCU1 | 6(3) | 1(1) | 02B1-01 | 0 |
| ESPCU1 | 13(7) | 2(2) | 02C1-01 | 0 |
| | | | 1 \| 2 \| 3 | |

Daily patient count

Legend: ☐ Test ordered    ☒ CV19

4/1 — ○ Test ordered 42    ○ CV19 positive 10

Bar chart dates: 3/19, 3/21, 3/23, 3/25, 3/27, 3/29, 3/31 (y-axis 0–50)

EVS for CC + NP     To clean: NP 3

| EVS | Bed status | Next patient | Location |
|---|---|---|---|
| | (H) CCU1-5 | M.SMI 12121212 | ED |
| ✂ | MED6-21 | [2] | |
| ✂ | MED4-38 | [2] | |
| ✂✂ | SICU1-8 | [3] | |
| ✂✂ | MED4-36 | [2] | |
| | MED6-20 | 1 \| 2 | |

| National capacity | National by state | MSA ● State | | | | | | | | | | | Search by hospital name, address 🔍 ⓘ ⚙ | |
|---|---|---|---|---|---|---|---|---|---|---|---|---|---|---|
| | All beds | Adult | | | | PEDS | | | Vents | | Covid | |
| Census\|Unocc\|Ca... | | ICU | IMC | Acute | OBS | ICU | IMC/Acute | OBS | In use | | PUI | CV19+ |
| Total | 94,273 82% | 94,273 82% | 57,114 85% | 432,254 86% | 34,067 81% | 16,853 81% | 16,208 83% | 19,837 79% | 57,974 81% | | 1,114,944 | 124,217 |
| Northeast | 15,569 90% | 15,569 90% | 10,566 93% | 75,936 89% | 5,352 76% | 3,427 90% | 29,763 91% | 3,442 81% | 10,585 90% | | 666,738 | 74,082 |
| D1: New England › | 3,411 82% | 3,411 82% | 2,428 87% | 17,664 84% | 894 51% | 365 76% | 6,366 76% | 785 75% | 1,952 76% | | 59,904 | 6,656 |
| D2: Mid Atlantic › | 12,158 92% | 12,158 92% | 8,138 95% | 58,272 91% | 4,448 73% | 3,062 92% | 23,397 95% | 2,657 83% | 8,633 94% | | 606,834 | 67,426 |
| Midwest | 172,275 82% | 19,375 80% | 12,084 83% | 91,643 84% | 7,432 81% | 3,453 82% | 33,883 81% | 4,403 80% | 12,562 86% | | 125,529 | 13,948 |
| D3: East N.Central › | 115,464 83% | 13,720 82% | 8,158 84% | 60,765 84% | 5,064 84% | 2,339 81% | 22,428 81% | 2,990 83% | 9,017 87% | | 106,533 | 11,837 |
| D4: West N. Central › | 56,810 81% | 5,654 76% | 3,926 79% | 30,878 83% | 2,369 77% | 1,115 83% | 11,455 81% | 1,413 76% | 3,545 83% | | 18,996 | 2,111 |
| South | 349,335 82% | 40,110 79% | 24,558 83% | 185,903 84% | 14,881 81% | 7,153 79% | 68,185 81% | 8,546 77% | 21,615 71% | | 184,203 | 20,467 |
| D5: South Atlantic › | 155,932 86% | 17,833 83% | 10,992 87% | 83,370 88% | 6,557 83% | 2,958 83% | 30,399 83% | 3,822 80% | 10,238 76% | | 95,391 | 10,599 |
| D6: East S. Central › | 99,660 80% | 11,366 77% | 7,037 82% | 53,313 83% | 4,257 79% | 2,131 77% | 19,211 78% | 2,344 73% | 6,268 73% | | 29,421 | 3,269 |
| D7: West S. Central › | 93,744 80% | 10,910 76% | 6,529 80% | 49,221 81% | 4,066 80% | 2,064 75% | 18,574 79% | 2,380 78% | 5,110 62% | | 59,391 | 6,599 |
| West | 148,942 85% | 19,220 85% | 9,906 83% | 78,772 88% | 6,402 86% | 2,819 76% | 28,377 82% | 3,446 77% | 11,540 79% | | 138,474 | 15,386 |
| D8: Mountain › | 45,841 81% | 5,816 81% | 3,140 81% | 23,800 82% | 1,848 76% | 962 75% | 9,148 82% | 1,128 76% | 3,339 76% | | 43,038 | 4,782 |
| D9: Pacific › | 103,101 87% | 13,404 87% | 6,766 84% | 54,972 91% | 4,554 90% | 1,858 76% | 19,229 83% | 2,318 76% | 8,202 81% | | 95,436 | 10,604 |

FIG. 37

| | | | Adult | | | | PEDS | | | Vents | Covid | |
|---|---|---|---|---|---|---|---|---|---|---|---|---|
| Census\|Unocc\|Ca... | All beds | ICU | IMC | Acute | OBS | ICU | IMC/Acute | OBS | In use | PUI | CV19+ |
| Total | 814,273 84% | 94,273 82% | 57,114 85% | 432,254 86% | 34,067 81% | 16,853 81% | 16,208 83% | 19,837 79% | 57,974 81% | 1,114,944 | 124,217 |
| Northeast | 144,055 89% | 15,569 90% | 10,566 93% | 75,936 89% | 5,352 76% | 3,427 90% | 29,763 91% | 3,442 81% | 10,585 90% | 666,738 | 74,082 |
| D1: New England | 31,912 81% | 3,411 82% | 2,428 87% | 17,664 84% | 894 51% | 365 76% | 6,366 79% | 785 75% | 1,952 76% | 59,904 | 6,656 |
| D2: Mid Atlantic | 112,142 92% | 12,158 92% | 8,138 95% | 58,272 91% | 4,448 83% | 3,062 92% | 23,397 95% | 2,657 83% | 8,633 94% | 606,834 | 67,426 |
| New Jersey | 21,830 90% | 2,595 88% | 1,580 95% | 11,230 90% | 832 80% | 538 88% | 4,544 95% | 512 82% | 1,823 93% | 100,116 | 11,124 |
| New York | 52,683 93% | 5,546 94% | 3,827 97% | 27,226 92% | 2,195 89% | 1,642 94% | 11,004 97% | 1,243 84% | 3,980 95% | 481,032 | 53,448 |
| Pennsylvania | 37,630 81% | 4,017 92% | 2,730 93% | 19,816 90% | 1,431 78% | 883 92% | 7,849 93% | 903 82% | 185 95% | 532 | 390 |
| Midwest | 172,275 82% | 19,375 80% | 12,084 83% | 91,643 84% | 7,432 81% | 3,453 82% | 33,883 81% | 4,403 80% | 12,562 86% | 125,529 | 13,948 |
| D3: East N. Central | 115,464 83% | 13,720 82% | 8,158 84% | 60,765 84% | 5,064 84% | 2,339 81% | 22,428 81% | 2,990 83% | 9,017 87% | 106,533 | 11,837 |
| D4: West N. Central | 56,810 81% | 5,654 76% | 3,926 79% | 30,878 83% | 2,369 77% | 1,115 83% | 11,455 81% | 1,413 76% | 3,545 83% | 18,996 | 2,111 |
| South | 349,335 82% | 40,110 79% | 24,558 83% | 185,903 84% | 14,881 81% | 7,153 79% | 68,185 81% | 8,546 77% | 21,615 71% | 184,203 | 20,467 |
| D5: South Atlantic | 155,932 86% | 17,833 83% | 10,992 87% | 83,370 88% | 6,557 83% | 2,958 83% | 30,399 83% | 3,822 80% | 10,238 76% | 95,391 | 10,599 |
| D6: East S. Central | 99,660 80% | 11,366 77% | 7,037 82% | 53,313 83% | 4,257 79% | 2,131 77% | 19,211 78% | 2,344 73% | 6,268 73% | 29,421 | 3,269 |
| D7: West S. Central | 93,744 80% | 10,910 76% | 6,529 80% | 49,221 81% | 4,066 80% | 2,064 75% | 18,574 79% | 2,380 78% | 5,110 62% | 59,391 | 6,599 |

FIG. 38

| | | | Adult | | | | PEDS | | | Vents | Covid | |
|---|---|---|---|---|---|---|---|---|---|---|---|---|
| Census\|Unocc\|Ca... | All beds | ICU | IMC | Acute | OBS | ICU | IMC/Acute | OBS | In use | | PUI | CV19+ |
| Total | 814,606 84% | 94,273 82% | 57,114 85% | 432,254 86% | 34,067 81% | 16,853 81% | 16,208 83% | 19,837 79% | 57,974 81% | | 1,114,944 | 124,217 |
| Northeast | 144,055 89% | 15,569 90% | 10,566 93% | 75,936 89% | 5,352 76% | 3,427 90% | 29,763 91% | 3,442 81% | 10,585 90% | | 666,738 | 74,082 |
| D1: New England > | 31,912 81% | 3,411 82% | 2,428 87% | 17,664 84% | 894 51% | 365 76% | 6,366 92% | 785 95% | 1,952 76% | | 59,904 | 6,656 |
| D2: Mid Atlantic ∨ | 112,142 92% | 12,158 92% | 8,138 95% | 58,272 91% | 4,448 83% | 3,062 92% | 23,397 95% | 2,657 83% | 8,633 94% | | 606,834 | 67,426 |
| New jersey > | 21,830 90% | 2,595 88% | 1,580 95% | 11,230 90% | 832 80% | 538 88% | 4,544 95% | 512 82% | 1,823 93% | | 100,116 | 11,124 |
| New York ∨ | 52,683 93% | 5,546 94% | 3,827 97% | 27,226 92% | 2,195 89% | 1,642 94% | 11,004 97% | 1,243 84% | 3,980 95% | | 481,032 | 53,448 |
| NY Presbyterian | 2,566 97% | 257 97% | 133 100% | 1,323 96% | 76 95% | 201 95% | 530 100% | 47 88% | 185 95% | | 532 | 390 |
| NYU langone | 1,585 97% | 155 95% | 79 96% | 830 98% | 48 99% | 125 96% | 319 98% | 29 90% | 111 93% | | 372 | 211 |
| Long island jewish | 1,500 97% | 152 98% | 77 100% | 773 96% | 44 94% | 118 95% | 310 100% | 26 85% | 109 95% | | 297 | 209 |
| Montefiore | 1,522 100% | 153 100% | 76 100% | 795 100% | 46 100% | 116 95% | 306 100% | 30 97% | 110 96% | | 476 | 204 |
| Mount sinai NY | 1,121 93% | 109 92% | 55 78% | 586 86% | 33 78% | 88 84% | 228 89% | 22 100% | 78 81% | | 257 | 152 |
| Buffalo general | 788 74% | 73 68% | 40 74% | 376 68% | 31 97% | 64 75% | 188 88% | 15 70% | 52 97% | | 157 | 110 |
| North shore LIJ | 1,008 97% | 98 94% | 50 97% | 530 98% | 31 99% | 75 90% | 204 98% | 20 95% | 70 95% | | 128 | 142 |
| NYC belleview | 891 98% | 88 97% | 64 100% | 465 98% | 27 97% | 68 93% | 181 99% | 17 95% | 64 91% | | 176 | 134 |

FIG. 39

| Census | Unocc | Ca... | All beds | Adult | | | | PEDS | | | Vents | Covid | |
|---|---|---|---|---|---|---|---|---|---|---|---|---|---|
| | | | | ICU | IMC | Acute | OBS | ICU | IMC/Acute | OBS | In use | PUI | CV19+ |
| Total | | > | 814,606 84% | 94,273 82% | 57,114 85% | 432,254 86% | 34,067 81% | 16,853 81% | 16,208 83% | 19,837 79% | 57,974 81% | 1,114,944 | 124,217 |
| Northeast | | | 144,055 89% | 15,569 90% | 10,566 93% | 75,936 89% | 5,352 76% | 3,427 90% | 29,763 91% | 3,442 81% | 10,585 90% | 666,738 | 74,082 |
| D1: New England | | > | 31,912 81% | 3,411 82% | 2,428 87% | 17,664 84% | 894 51% | 365 76% | 6,366 92% | 785 95% | 1,952 76% | 59,904 | 6,656 |
| D2: Mid Atlantic | | > | 112,142 92% | 12,158 92% | 8,138 95% | 58,272 91% | 4,448 83% | 3,062 92% | 23,397 95% | 2,657 83% | 8,633 94% | 606,834 | 67,426 |
| New jersey | | > | 21,830 90% | 2,595 88% | 1,580 95% | 11,230 90% | 832 80% | 538 88% | 4,544 95% | 512 82% | 1,823 93% | 100,116 | 11,124 |
| New York | | > | 52,683 93% | 5,546 94% | 3,827 97% | 27,226 92% | 2,195 89% | 1,642 94% | 11,004 97% | 1,243 84% | 3,980 95% | 481,032 | 53,448 |
| NY Presbyterian | | | 2,566 97% | 257 97% | 133 100% | 1,323 96% | 76 95% | 201 95% | 530 100% | 47 88% | 185 95% | 532 | 390 |
| NYU langone | | | 1,585 97% | 155 95% | 79 96% | 830 98% | 48 99% | 125 96% | 319 98% | 29 90% | 111 93% | 372 | 211 |
| Long island jewish | | | 1,500 97% | 152 98% | 77 100% | 773 96% | 44 94% | 118 95% | 310 100% | 26 85% | 109 95% | 297 | 209 |
| Montefiore | | | 1,522 100% | 153 100% | 76 100% | 795 100% | 46 100% | 116 95% | 306 100% | 30 97% | 110 96% | 476 | 204 |
| Mount sinai NY | | | 1,121 93% | 109 92% | 55 78% | 586 86% | 33 78% | 88 84% | 228 89% | 22 100% | 78 81% | 257 | 152 |
| Buffalo general | | | 788 74% | 73 68% | 40 74% | 376 68% | 31 97% | 64 75% | 188 88% | 15 70% | 52 97% | 157 | 110 |
| North shore LIJ | | | 1,008 97% | 98 94% | 50 97% | 530 98% | 31 99% | 75 90% | 204 98% | 20 95% | 70 95% | 128 | 142 |
| NYC belleview | | | 891 98% | 88 97% | 64 100% | 465 98% | 27 97% | 68 93% | 181 99% | 17 95% | 64 91% | 176 | 134 |

FIG. 40

| National capacity | All beds | | | Adult | | | | PEDS | |
|---|---|---|---|---|---|---|---|---|---|
| Census Unocc Ca... | | ICU | IMC | Acute | OBS | ICU | IMC/Acute |
| Total > | 814,606 84% | 94,273 82% | 57,114 85% | 432,254 86% | 34,067 81% | 16,853 81% | 16,208 83% |
| ◆ Northeast | 144,055 89% | 15,569 90% | 10,566 93% | 75,936 89% | 5,352 76% | 3,427 90% | 29,763 91% |
| D1: New England > | 31,912 81% | 3,411 82% | 2,428 87% | 17,664 84% | 894 51% | 365 76% | 6,366 92% |
| ◆ D2: Mid Atlantic ∨ | 112,142 92% | 12,158 92% | 8,138 95% | 58,272 91% | 4,448 83% | 3,062 92% | 23,397 95% |
| ◆ New jersey > | 21,830 90% | 2,595 88% | 1,580 95% | 11,230 90% | 832 80% | 538 88% | 4,544 95% |
| ◆ New York ∨ | 52,683 93% | 5,546 94% | 3,827 97% | 27,226 92% | 2,195 89% | 1,642 94% | 11,004 97% |
| ∨ NY Presbyterian | 2,566 97% | 257 97% | 133 100% | 1,323 96% | 76 95% | 201 95% | 530 100% |
| ◆ NYU langone | 1,585 97% | 155 95% | 79 96% | 830 98% | 48 99% | 125 96% | 319 98% |
| ◆ Long island jewish | 1,500 97% | 152 98% | 77 100% | 773 96% | 44 94% | 118 95% | 310 100% |
| ◆ Montefiore | 1,522 100% | 153 100% | 76 100% | 795 100% | 46 100% | 116 95% | 306 100% |
| ◆ Mount sinai NY | 1,121 97% | 109 94% | 55 78% | 586 86% | 33 78% | 88 84% | 228 89% |
| ○ Buffalo general | 788 74% | 73 68% | 40 74% | 376 68% | 31 97% | 64 75% | 188 88% |
| ◆ North shore LIJ | 1,008 97% | 98 94% | 50 97% | 530 98% | 31 99% | 75 90% | 204 98% |
| NYC belleview | 891 98% | 88 97% | 64 100% | 465 98% | 27 97% | 68 93% | 181 99% |

USA · National by state · MSA ● State

⚙ Settings    ✕

Expanded sections - read only, adjust on tile

| Region | Division | State | Facility |
|---|---|---|---|
| N | D2 | NY | NY |
| S | D9 | WA | WA |

Geographical grouping [State ▾]

Count displayed [Census ▾]

Sorting Clear all

Field · Sort by · Ascending / desce...
All · [All beds count ▾] · [Descending ▾]

Filters · [AND | OR] · - Remove filter

Alert level ▾    Select all / select none
Options
☑ ● Critical
☑ △ Warning
☑ No alert
☑ ○ Beds available (+ Add filter)

(Save settings) (Reset) (Cancel) (Apply)

FIG. 41

| | | | Adult | | | | PEDS | |
|---|---|---|---|---|---|---|---|---|
| | All beds | ICU | IMC | Acute | OBS | ICU | IMC/Acute |
| Census Unocc Ca... | | | | | | | | |
| Total ⌄ | 814,606 84% | 94,273 82% | 57,114 85% | 432,254 86% | 34,067 81% | 16,853 81% | 16,208 83% |
| ⚠ Northeast | 144,055 89% | 15,569 90% | 10,566 93% | 75,936 89% | 5,352 76% | 3,427 90% | 29,763 91% |
| D1: New England ⌄ | 31,912 81% | 3,411 82% | 2,428 87% | 17,664 84% | 894 51% | 365 76% | 6,366 92% |
| ⚠ D2: Mid Atlantic ⌄ | 112,142 92% | 12,158 92% | 8,138 95% | 58,272 91% | 4,448 83% | 3,062 92% | 23,397 95% |
| ⚠ New Jersey ⌄ | 21,830 90% | 2,595 88% | 1,580 95% | 11,230 90% | 832 80% | 538 88% | 4,544 95% |
| ⚠ New York ⌄ | 52,683 93% | 5,546 94% | 3,827 97% | 27,226 92% | 2,195 89% | 1,642 94% | 11,004 97% |
| ⚠ NY Presbyterian | 2,566 97% | 257 97% | 133 100% | 1,323 96% | 76 95% | 201 95% | 530 100% |
| ⚠ NYU langone | 1,585 97% | 155 95% | 79 96% | 830 98% | 48 99% | 125 96% | 319 98% |
| ⚠ Long island jewish | 1,500 97% | 152 98% | 77 100% | 773 96% | 44 94% | 118 95% | 310 100% |
| ⚠ Montefiore | 1,522 100% | 153 100% | 76 100% | 795 100% | 46 100% | 116 95% | 306 100% |
| ⚠ Mount sinai NY | 1,121 97% | 109 94% | 55 78% | 586 86% | 33 78% | 88 84% | 228 89% |
| ○ Buffalo general | 788 74% | 73 68% | 40 74% | 376 68% | 31 97% | 64 75% | 188 88% |
| ⚠ North shore LIJ | 1,008 97% | 98 94% | 50 97% | 530 98% | 31 99% | 75 90% | 204 98% |
| NYC belleview | 891 98% | 88 97% | 64 100% | 465 98% | 27 97% | 68 93% | 181 99% |

⚙ Settings ✕

Expanded sections - read only, adjust on tile

| Region | Division | State |
|---|---|---|
| N | D2 | NY |
| S | D9 | WA |

Geographical grouping [State ▾]

Count displayed [Census ▾]

Sorting Clear all

Field | Sort by | Ascending / desce...
All | All beds count ▾ | Descending ▾

Filters [AND][OR] − Remove filter

Alert level ▾    Select all / select none

Options
☑ ⬤ Critical
☐ ⚠ Warning
☐ No alert
☑ ○ Beds available (+ Add filter)

(Save settings) (Reset)   (Cancel) (Apply)

FIG. 42

| | All beds | Adult | | | | PEDS | | | | Vents | | Covid | |
|---|---|---|---|---|---|---|---|---|---|---|---|---|---|
| USA [Census|Unocc|Ca...] | | ICU | IMC | Acute | OBS | ICU | IMC/Acute | OBS | | In use | | PUI | CV19+ |
| Total | 814,606 84% | 94,273 82% | 57,114 85% | 432,254 86% | 34,067 81% | 16,853 81% | 16,208 83% | 19,837 79% | | 57,974 81% | | 1,114,944 | 124,217 |
| ⚠ Northeast | Filter applied | | | | | 3,427 90% | 29,763 91% | 3,442 81% | | 10,585 90% | | 666,738 | 74,082 |
| D1: New Engla | Alert level[critical, bed available]<br>Displaying: 4569 of 7582 facilities | | | | | 365 76% | 6,366 79% | 785 95% | | 1,952 76% | | 59,904 | 6,656 |
| 🔔 D2: Mid Atla | | | | | Clear filter | 3,062 92% | 23,397 95% | 2,657 83% | | 8,633 94% | | 606,834 | 67,426 |
| 🔔 New jersey | 21,830 90% | 2,595 88% | 1,580 95% | 11,230 90% | 832 80% | 538 88% | 4,544 95% | 512 82% | | 1,823 93% | | 100,116 | 11,124 |
| 🔔 New York 183/277 ⌄ | 52,683 93% | 5,546 94% | 3,827 97% | 27,226 92% | 2,195 89% | 1,642 94% | 11,004 97% | 1,243 84% | | 3,980 95% | | 481,032 | 53,448 |
| 🔔 NY Presbyterian | 2,566 97% | 257 97% | 133 100% | 1,323 96% | 76 95% | 201 95% | 530 100% | 47 88% | | 185 95% | | 532 | 390 |
| 🔔 NYU langone | 1,585 97% | 155 95% | 79 96% | 830 98% | 48 99% | 125 96% | 319 98% | 29 90% | | 111 93% | | 372 | 211 |
| 🔔 Long island jewish | 1,500 97% | 152 98% | 77 100% | 773 96% | 44 94% | 118 95% | 310 100% | 26 85% | | 109 95% | | 297 | 209 |
| 🔔 Montefiore | 1,522 100% | 153 100% | 76 100% | 795 100% | 46 100% | 116 95% | 306 100% | 30 97% | | 110 96% | | 476 | 204 |
| ○ Buffalo general | 788 74% | 73 68% | 40 74% | 376 68% | 31 72% | 64 75% | 188 88% | 15 70% | | 52 64% | | 157 | 110 |
| ○ Upstate university | 551 75% | 76 69% | 32 74% | 191 74% | 33 78% | 87 84% | 110 72% | 22 78% | | 59 64% | | 118 | 93 |
| ○ Saratoga | 132 77% | 15 68% | 18 97% | 45 98% | 12 99% | 11 90% | 23 98% | 8 95% | | 22 63% | | 63 | 31 |
| ○ White plains | 213 76% | 20 97% | 23 100% | 110 98% | 14 97% | 12 93% | 24 99% | 10 95% | | 34 61% | | 52 | 42 |

FIG. 44

SYSTEMS AND METHODS FOR RESOURCE AVAILABILITY MANAGEMENT

RELATED APPLICATIONS

This application claims priority to U.S. Provisional Application No. 63/008,593, filed Apr. 10, 2020, the entire contents of which are hereby incorporated by reference for all purposes.

FIELD

Embodiments of the subject matter disclosed herein relate to resource management across hospital networks, specifically with respect to the use of computerized tools for displaying available resources between units, facilities, regions, etc., for allocation purposes in the context of unexpected scarcity.

BACKGROUND

Acute care of patients in a hospital or other medical facility may include the use of resources such as medical devices, intensive care unit (ICU) beds, and the like. Hospitals may maintain sufficient resources to care for an expected number of patients that may peak based on seasonal flu transmission or other anticipated events that cause temporary surges in hospital admissions. However, hospital resources may be stretched thin or even become unavailable if an unexpected number of patients are admitted to the hospital, particularly if multiple patients are admitted for the same condition and thus demand the same hospital resources.

BRIEF DESCRIPTION

In one embodiment, a method includes receiving first data from a first medical facility, the first data received via a first data streaming process and in a first format; receiving second data from a second medical facility, the second data received via a second data streaming process and in a second format; processing the first data and the second data to generate one or more resource availability graphical user interfaces (GUIs); and outputting the one or more resource availability GUIs for display on a display device.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below:

FIG. 11B is an example table that may be accessed in order to determine a patient disease status for a patient that has tested positive at least one time for the disease.

FIG. 11C is an example table that may be accessed in order to determine a patient disease status for a patient that has not tested positive for the disease.

FIG. 17 shows an example view of the GUI of FIG. 15 that displays resource availability within a hospital network at a regional level.

FIG. 18 shows an example view of the GUI of FIG. 15 that displays resource availability within a hospital network at a regional level, where additional data is displayed via a pop-up display panel.

FIG. 19 shows an example view of the GUI of FIG. 15 that displays resource availability within a hospital network at a facility level.

FIG. 21 shows an example view of the GUI of FIG. 15 that displays resource availability within a hospital network at a unit level within a facility.

FIGS. 22-25 show an example GUI that displays resource availability within a hospital network at different geographical scopes.

FIGS. 26-27 show example views of the GUI of FIG. 22 that display resource availability within a hospital network, where filtering and sorting options may be selected via a settings panel.

FIG. 28 shows an example view of the GUI of FIG. 22 that displays resource availability within a hospital network, where the display of resources has been ordered based on resource availability.

FIG. 29 shows an example GUI that displays resource utilization within a hospital via customized, modular layouts.

FIGS. 30-32 show example views of the GUI of FIG. 29 that display resource utilization within a hospital, where additional data is displayed via a pop-up display panel.

FIGS. 34-35 show example views of the GUI of FIG. 29 that display resource utilization within a hospital, where customization options may be selected via a settings panel.

FIGS. 37-44 show example views of a national capacity GUI according to another embodiment of the disclosure.

DETAILED DESCRIPTION

Figure 1:
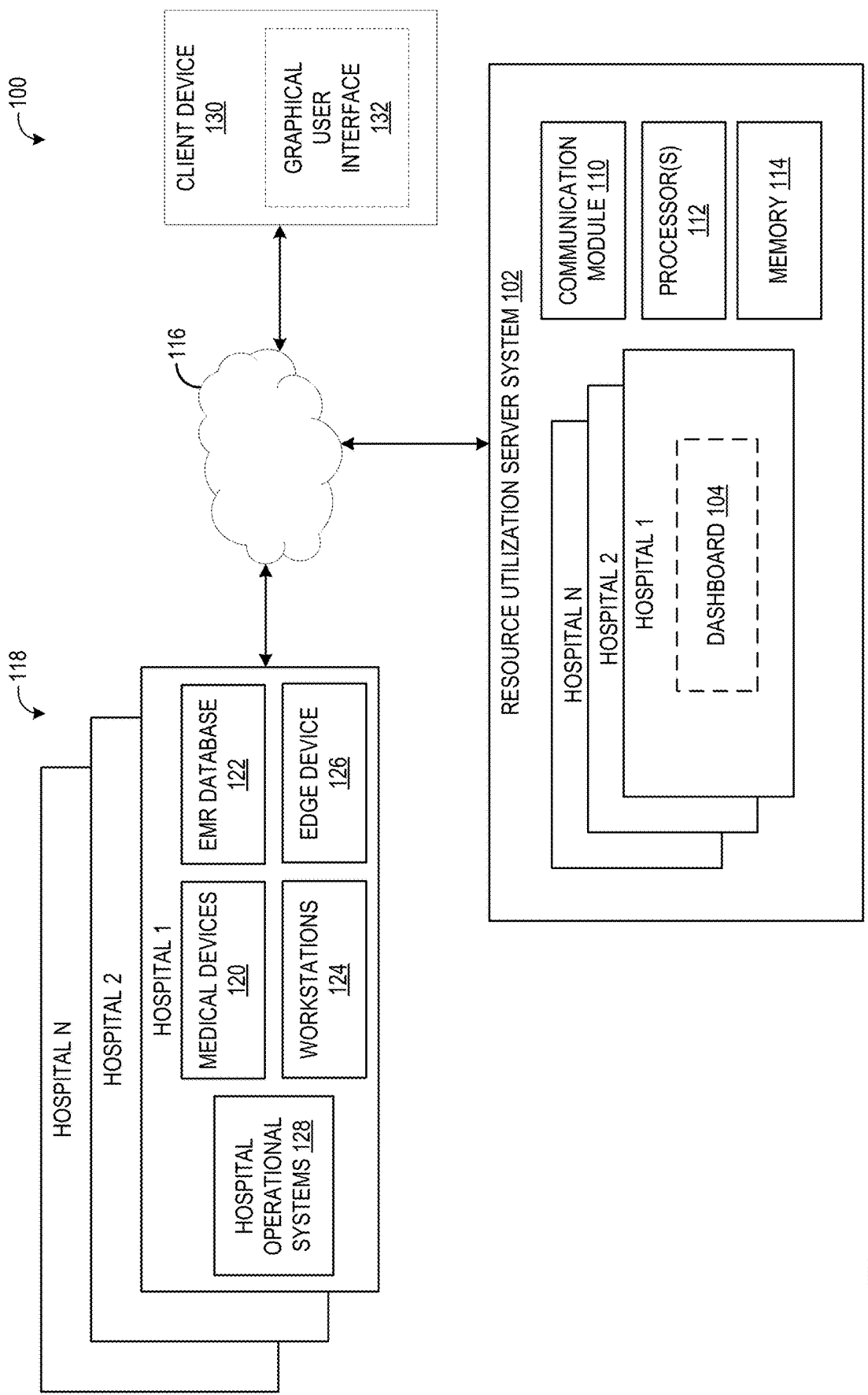
FIG. 1 schematically shows an example collaborative resource utilization system.

Healthcare facilities may be equipped to handle an expected amount of patients, with additional resources available in reserve to provide surge capacity for unanticipated events where more than an expected amount of patients demand care. However, certain situations such as infectious disease outbreaks may strain healthcare systems, often demanding more resources than facilities are equipped to provide, even accounting for resources that may be in reserve. Thus, medical facilities across cities, states, regions, and even entire countries and beyond may collect and share resource availability data to enable healthcare authorities such as hospital administrators, government agencies, and the like to make decisions about sharing/allocating available resources, ordering new equipment, hiring additional healthcare workers, etc. However, collecting resource availability data may be time-consuming and demand personnel time, which may strain healthcare systems. For example, many medical facilities may have no centralized system in place to track how many critical medical resources, such as ventilators, are currently in use, scheduled to be in use, undergoing maintenance, etc., and thus people may manually determine ventilator usage by visually inspecting each room of each ward/unit of the medical facility, which is time-consuming and prone to error. Further, maintaining up-to-date resource availability data may be challenging when relying on standard methods to collect the resource availability data. Thus, when decisions are made about how to allocate resources across multiple medical facilities, when to request additional resources, etc., the decisions may be made based on incomplete or outdated information, which may result in a lack of resources at some facilities while other facilities may have an abundance of resources, which may ultimately compromise patient care.

Thus, according to embodiments disclosed herein, current resource availability data may be collected from a plurality of medical facilities and aggregated automatically, in real-time or near real-time. The aggregated data may be visualized via one or more graphical user interfaces that may indicate critical resource availability (e.g., bed availability, ventilator availability) as well as infectious disease information (e.g., number of positive cases, number of patients under investigation) by unit, hospital, hospital network, state, region, and/or nationwide. The resource availability data and infection disease information may be updated automatically as resource availability changes and/or as disease test results are made available. In doing so, healthcare authorities may be apprised of resource availability information for multiple medical facilities at once, while also being apprised of outbreak progression, which may enable the healthcare authorities to make informed decisions about resource allocation based on up-to-date information, via one or more graphical user interfaces that may present a limited set of information (e.g., critical resource availability, locality/region-based disease status) to the users/healthcare authorities. In this way, the users' interaction with the available data may be made more efficient, as users are not forced to sift through multiple separate data feeds, data files, etc., to identify and then aggregate the needed information.

FIG. 1 schematically shows an example collaborative resource utilization system 100 that may be implemented across multiple medical facilities such as hospitals. Collaborative resource utilization system 100 may include a resource utilization server system 102. Server system 102 may include resources (e.g., memory 114, processor(s) 112) that may be allocated to store and execute one or more resource dashboards. For example, as shown in FIG. 1, a dashboard 104 is stored on server system 102 for a first hospital (hospital 1); a plurality of additional dashboards may be stored on server system 102, each corresponding to a respective hospital (hospital 2 up to hospital N).

As will be explained in more detail below, each dashboard may indicate resource utilization and availability for each hospital. For example, each dashboard may track, for a corresponding hospital, the total number of hospital beds, total occupied hospital beds, total and occupied hospital beds by bed type (e.g., ICU, progressive care unit, observational care, negative pressure, etc.), and total and utilized medical devices, such as ventilators. Further, data from one or more hospital-specific dashboards may be combined to generate a hospital network dashboard, a regional hospital dashboard, a national hospital dashboard, etc., in order to track/indicate resource utilization across multiple hospitals, regions, and even nationwide. When requested, the dashboards may be output for display on a display device as one or more graphical user interfaces, as described below. As used herein, a dashboard may include data on resource utilization for a unit, a hospital, a hospital network, hospitals within a certain region, and/or hospitals nationwide. The dashboard may include data that may be rendered as one or more of the graphical user interfaces that will be described in more detail below. The dashboards may not have any specific visual appearance and may include the data aggregated from one or more hospitals that is updated as new data is received.

The server system 102 may be communicatively coupled to a plurality of hospitals 118 via a network 116, from a first hospital (hospital 1), a second hospital (hospital 2), and on up to an Nth hospital (hospital N). Each hospital may be configured to send resource utilization information to the server system 102. The resource utilization information may include the information that is tracked via the dashboards described above, such as hospital bed utilization and medical device utilization.

In order to collect and send the resource utilization information to the server system 102, each hospital may include various systems and devices to track, in real-time, patient admission, patient bed assignment, medical device deployment, patient condition information (e.g., diagnosed patient conditions, suspected patient conditions, patient lab results, etc.), and so forth, and send the tracked information to the server system 102. FIG. 1 shows an example of hospital systems and devices for the first hospital that may be used to collect hospital resource utilization information, send the collected hospital resource utilization information to the server system 102, and/or view one or more dashboards generated by server system 102. It should be appreciated that the hospital systems and devices described herein are exemplary, and that other systems and/or devices may be used to collect and send the hospital resource utilization information without departing from the scope of this disclosure. Further, while hospitals are described herein, other medical facilities may send resource utilization information to the server system 102, such as outpatient clinics, local or regional health authorities, other government agencies, etc.

Hospital 1 may include a hospital operational systems 128. The hospital operational systems 128 may store and/or control a variety of hospital-, care provider-, and patient-related information, including but not limited to patient admission information (including date of admission and location of the patient within the medical facility), medical device information (e.g., total number of each type of medical device, current status of each medical device, etc.), patient care protocols and workflows, and care provider information including which care providers are monitoring/treating which patients. Further, the hospital operational systems 128 may be communicatively coupled to a plurality of medical devices 120, an electronic medical records (EMR) database 122 (described in more detail below), and one or more workstations 124.

The medical devices 120 may include medical devices configured to monitor and/or provide medical treatment to respective patients, such as ventilators, anesthesia machines, infusion pumps, pulse oximeters, heart rate monitors, blood glucose monitors, ECGs, etc., as well as microphones, cameras, and other devices. The medical devices 120 may send output to the hospital operational systems 128, EMR database 122, and/or one or more care provider devices. Further, in some examples, hospital operational systems 128 and/or EMR database 122 may receive diagnostic imaging information obtained from one or more imaging modalities, such as ultrasound, CAT, MRI, X-ray, etc. Based on the information output from the medical devices 120, the current utilization of each medical device may be tracked by the hospital operational systems 128 and/or EMR database 122. In some examples, data from one or more medical devices may be sent directly to server system 102.

The hospital operational systems 128 may track hospital bed usage. For example, when a patient is admitted, the hospital operational systems 128 may associate the patient with an identifier (e.g., an identification code) and track patient status, patient ward/unit assignment, patient bed assignment, and so forth. The hospital operational systems 128 may also track diagnosed and/or suspected patient condition(s). For example, hospital operational systems 128 may receive lab results from a laboratory service and update diagnosed patient condition(s) in response to the received lab results and/or information provided by the care provider(s) of each patient. In some examples, EMR database 122 may additionally or alternatively track diagnosed and/or suspected patient conditions based on information provided by providers, lab results, and/or other information.

EMR database 122 may be an external database or EMR database 122 may be a local database (e.g., housed on a device of the hospital). EMR database 122 may be a database stored in a mass storage device configured to communicate with secure channels (e.g., hypertext transfer protocol secure (HTTPS) and transport layer security (TLS)), and store data in encrypted form. Further, the EMR mass storage device is configured to control access to patient electronic medical records such that only authorized healthcare providers may edit and access the electronic medical records. An EMR for a patient may include patient demographic information, family medical history, past medical history, lifestyle information, preexisting medical conditions, current medications, allergies, surgical history, past medical screenings and procedures, past hospitalizations and visits, etc.

Hospital 1 further includes one or more workstations 124. Each workstation may include a processor, memory, communication module, user input device, display (e.g., screen or monitor), and/or other subsystems and may be in the form of a desktop computing device, a laptop computing device, a tablet, a smart phone, or other device. The workstations may be located locally at the hospital (such as part of hospital administration) and/or remotely from the hospital (such as a user's mobile device).

The hospital operational system 128, medical devices 120, EMR database 122, and workstations 124 may communicate with each other via a hospital network, which may be a suitable wired and/or wireless network. Communication between the systems/devices of hospital 1 and server system 102 may be provided by a suitable device, herein an edge device 126. Edge device 126 may exemplarily be an edge processing device, cloud processing device, or internet gateway. The edge device 126 may facilitate a secure communications link between the systems/devices communicating on the hospital network with the servers, processors, and computer readable media implementing the server system 102.

Server system 102 includes a communication module 110, memory 114, and processor(s) 112 to generate and store the dashboards described herein. Communication module 110 facilitates transmission of electronic data within and/or among one or more systems. Communication via communication module 110 can be implemented using one or more protocols. In some examples, communication via communication module 110 occurs according to one or more standards (e.g., Digital Imaging and Communications in Medicine (DICOM), Health Level Seven (HL7), ANSI X12N, etc.). Communication module 110 can be a wired interface (e.g., a data bus, a Universal Serial Bus (USB) connection, etc.) and/or a wireless interface (e.g., radio frequency, infrared, near field communication (NFC), etc.). For example, communication module 110 may communicate via wired local area network (LAN), wireless LAN, wide area network (WAN), etc. using any past, present, or future communication protocol (e.g., BLUETOOTH™, USB 2.0, USB 3.0, etc.).

Memory 114 includes one or more data storage structures, such as optical memory devices, magnetic memory devices, or solid-state memory devices, for storing programs and routines executed by processor(s) 112 to carry out various functionalities disclosed herein. Memory 114 may include any desired type of volatile and/or non-volatile memory such as, for example, static random access memory (SRAM), dynamic random access memory (DRAM), flash memory, read-only memory (ROM), etc. Processor(s) 112 may be any suitable processor, processing unit, or microprocessor, for example. Processor(s) 112 may be a multiprocessor system, and, thus, may include one or more additional processors that are identical or similar to each other and that are communicatively coupled via an interconnection bus.

As used herein, the terms "sensor," "system," "unit," or "module" may include a hardware and/or software system that operates to perform one or more functions. For example, a sensor, module, unit, or system may include a computer processor, controller, or other logic-based device that performs operations based on instructions stored on a tangible and non-transitory computer readable storage medium, such as a computer memory. Alternatively, a sensor, module, unit, or system may include a hard-wired device that performs operations based on hard-wired logic of the device. Various modules or units shown in the attached figures may represent the hardware that operates based on software or hard-wired instructions, the software that directs hardware to perform the operations, or a combination thereof.

"Systems," "units," "sensors," or "modules" may include or represent hardware and associated instructions (e.g., software stored on a tangible and non-transitory computer readable storage medium, such as a computer hard drive, ROM, RAM, or the like) that perform one or more operations described herein. The hardware may include electronic circuits that include and/or are connected to one or more logic-based devices, such as microprocessors, processors, controllers, or the like. These devices may be off-the-shelf devices that are appropriately programmed or instructed to perform operations described herein from the instructions described above. Additionally or alternatively, one or more of these devices may be hard-wired with logic circuits to perform these operations.

One or more of the devices described herein may be implemented over a cloud or other computer network. For example, server system 102 is shown in FIG. 1 as constituting a single entity, but it is to be understood that server system 102 may be distributed across multiple devices, such as across multiple servers.

Collaborative resource utilization system 100 may likewise include a client device 130, including a display on which a user may view data from the collaborative resource utilization system. For example, data from dashboard 104 may be displayed on client device 130 as a graphical user interface 132, allowing a user to view resources available at a given hospital N. Further, data from other dashboards, such as data aggregated from a plurality of hospitals in a hospital network, may be displayed on client device 130, within a graphical user interface, which may allow users to visualize and navigate between data stored in different dashboards. Graphical user interface 132 may also allow a user to further interact with the data included on a dashboard, as shown in FIGS. 15-36.

Client device 130 may include user input devices, memory, processors, and communication modules/interfaces similar to communication module 110, memory 114, and processor(s) 112 described above, and thus the description of communication module 110, memory 114, and processor(s) 112 likewise applies to the other devices described herein. The user input devices may include keyboards, mice, touch screens, microphones, or other suitable devices.

As an example, the client device may store one or more graphical user interface templates in memory that include placeholders for relevant information stored on server system 102. For example, client device 130 may include graphical user interface 132, comprising a template for a resource dashboard that a user of the client device may configure with placeholders for desired patient information. When the graphical user interface is displayed on the client device, the relevant information may be retrieved from server system 102 (e.g., from a dashboard) and inserted in the placeholders. In other examples, server system 102 may render selected dashboards into the graphical user interfaces described herein, and may send the graphical user interfaces for display on a display devices (e.g., of client device 130) when requested.

As will be explained in more detail below, each hospital or other medical facility may be configured to send data to server system 102 so that resource availability across hospital units, hospitals, hospital networks, regions, and/or nations may be tracked and the resource availability may be visualized through one or more resource availability graphical user interfaces, as described below. The resource availability may be updated in real-time or near real-time as data is received from each hospital. As used herein, real-time may include the data being sent as soon as the data is collected, immediately and without an intentional delay. In this way, as soon as a hospital has resource availability information available (e.g., a patient is admitted to a particular bed at the hospital), that resource availability information is sent to the server system. As used herein, near real-time may refer to the data being sent periodically from the hospital to the server system to allow for data aggregation, data filtering, and/or other data processing actions. However, the near-real time transmission of the data may still be rapid relative to when the data was made available, such as data being transmitted within 1-5 minutes of being made available (e.g., rather than as soon as the data is available).

Figure 2:
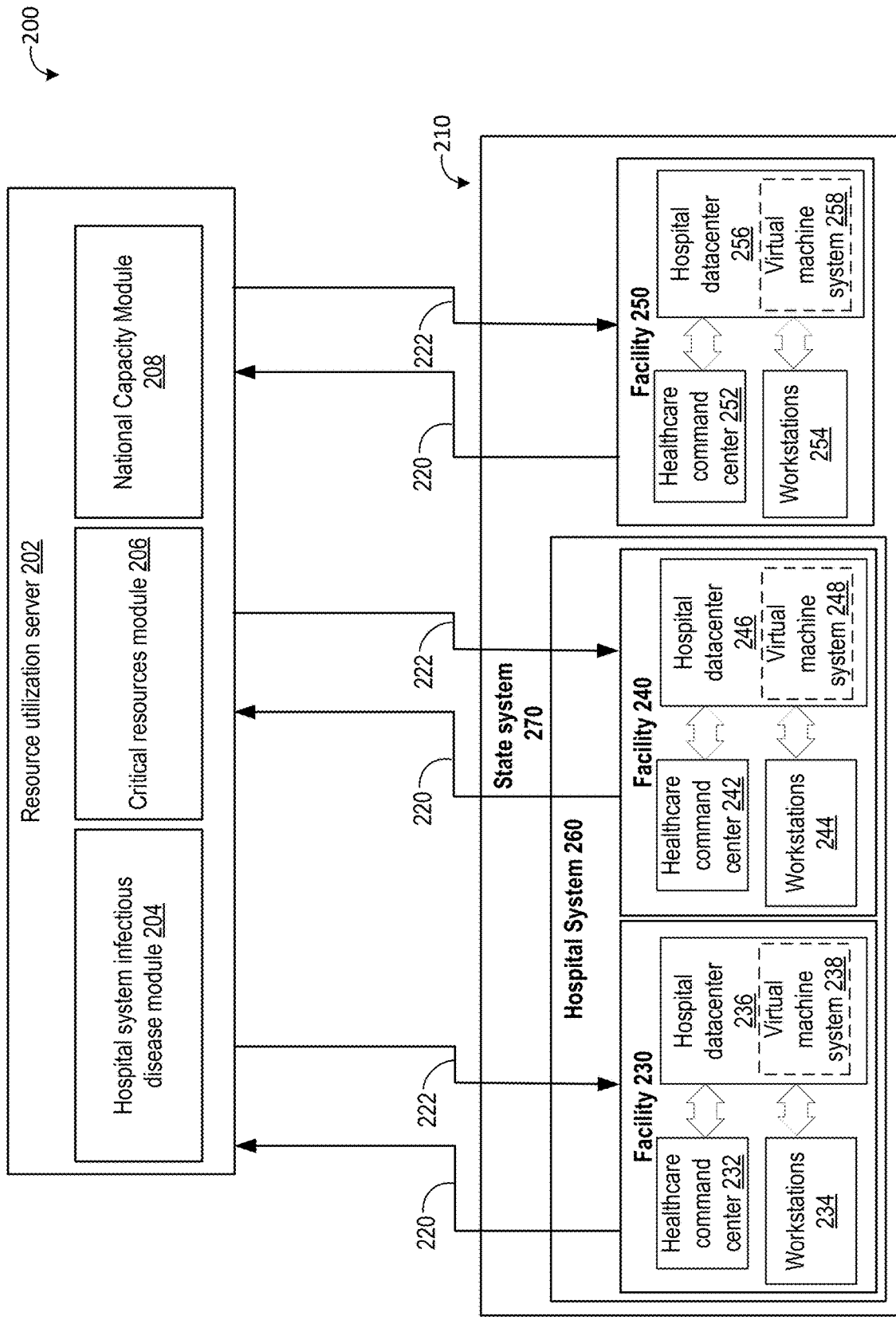
FIG. 2 schematically shows another example collaborative resource utilization system.

FIG. 2 shows another example collaborative resource utilization system 200 that may be implemented across various healthcare facilities (e.g., hospitals) and hospital systems within various geographical hierarchical areas. The collaborative resource utilization system 200 includes a resource utilization server 202 including a plurality of modules for receiving a plurality of data feeds from plurality of facilities, evaluating resource utilization in real-time or near real-time at each of the facilities, and generating a plurality of graphical user interface tiles that may be configured based on one or more of user query, data feed received from the facility and facility type. The resource utilization server 202 may be similar to resource utilization server system 102, and thus may include similar components in addition to the modules described here at FIG. 2, including communication module 110, processor 112, and non-transitory memory 114.

The collaborative resource utilization system 200 is shown including a state system 270 comprising a hospital system 260 and a facility 250 within a state. It will be appreciated that the state system 270 may include a plurality of hospital systems and/or plurality of facilities, depending on the population, area, location, etc. While the present example is illustrated with respect to resource utilization for a state, it will be appreciated that the collaborative resource utilization system 200 may be implemented for a region including a plurality of states, a nation including a plurality of regions, and also, internationally across a plurality of nations.

The hospital system 260 is shown including a facility 230 and a facility 240, although it should be appreciated that the hospital system may include fewer or more facilities.

Each of the facilities 230, 240, and 250 may include respective healthcare command centers 232, 242, and 252 for coordinating patient care and resources within the respective facility and/or across the respective hospital system. Each of the facilities 230, 240, and 250 further include respective data processing centers 236, 246, and 256 for performing various data-related operations, including collecting, storing, processing, distributing and/or allowing access to large amounts of data. While the present example shows each facility including a data center, other configurations, such as the data center being situated outside the facility, are also possible. In some example, two or more facilities within a hospital system may share a data center. Further, data centers 236, 246, and 256 may be configured as on-premise data centers, cloud-based data centers, or combination thereof. Each of the facilities 230, 240, and 250 further include workstations 234, 244, and 254. Each facility may include a plurality of workstations. The workstations may be command center workstations, medical device workstations, or any other type of workstation used to access and/or update one or more of patient information and hospital resource information, including critical resource information.

In one embodiment, as shown herein at FIG. 2, the hospital systems and facilities within the state system may form a part of a data-sharing hospital network system 210. As such, hospital data centers 236, 246, and 256 may be provisioned to include respective virtual machine systems 238, 248, and 258 for obtaining a plurality of data from one or more of respective hospital data centers, command centers, and workstations, processing the received data, and transmitting the data to the resource utilization server 202. Example data feeds from the virtual machine systems 238, 248, and 258 to the resource utilization server 202 are indicated at 220. While the present example shows each facility configured with a virtual machine system, it will be appreciated that the virtual machine system may configured based on the location and type of the data centers of the respective facilities and hospital systems. The data feeds 220 from the facilities 230, 240, and 250, via the respective virtual machine systems 238, 248, and 258, to the resource utilization server 202 may include one or more of flat file data feeds and HL7 data feeds, as described further below.

Further, the resource utilization server 202 may deliver one or more resource utilization dashboards, such as dashboard 104, to requesting workstations including display devices (e.g., command center workstations, medical device workstation, etc.) within the facilities and/or to any requesting client device, such as client devices described at FIG. 1. The communication of one or more resource utilization dashboards from the resource utilization server is indicated by 222. As indicated above, when requested, the dashboards may be output for display on a respective display device of the workstation via a graphical user interface (GUI). The one or more resource utilization dashboards may include a hospital system infectious disease dashboard, a critical resources dashboard, and a national capacity dashboard. The corresponding graphical user interfaces, including hospital system infectious disease user interfaces are shown and described at FIGS. 29 to 34, critical resources user interfaces are shown and described at FIGS. 16 to 21, and national capacity user interfaces are shown and described at FIGS. 22 to 28 and 36-44.

The virtual machine systems 238, 248, and 258 may include plurality of virtual machines including one or more processing units and non-transitory memory. Further, the virtual machine systems may allow access to hospital data to authorized personnel via a secured connection, such as VPN. While the present example at FIG. 2 describes data transfer to the resource utilization server 202 via virtual machines system provisioned within hospital data centers, another embodiment of a collaborative resource utilization system without implementing the virtual machines is shown at FIG. 3.

Figure 3:
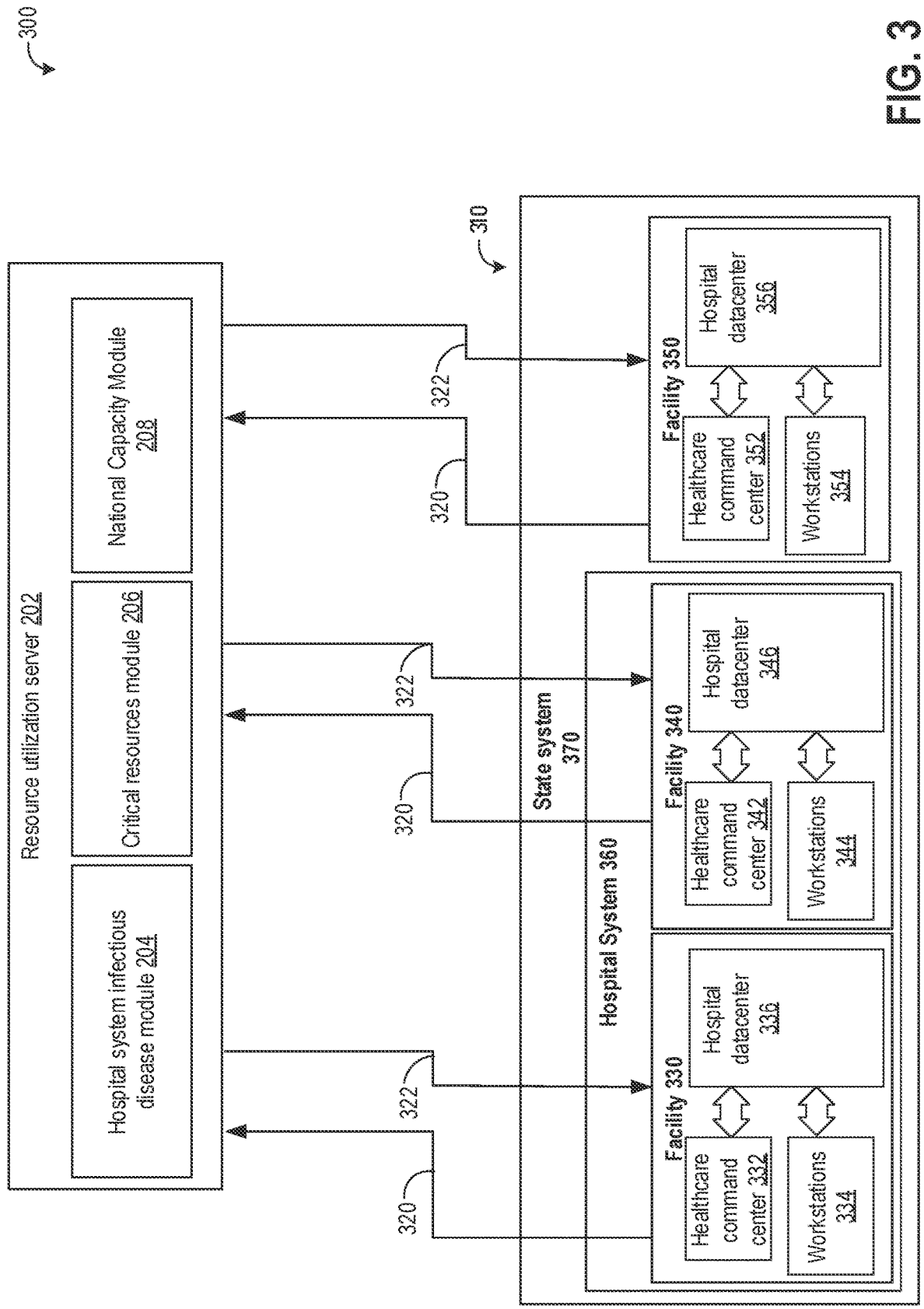
FIG. 3 schematically shows another example collaborative resource utilization system.

Turning to FIG. 3, another exemplary resource utilization system 300 is shown for a non-data sharing hospital network system 310. Hospital network system 310 includes facilities 330 and 340, which form part of a hospital system 360. Network system 310 further includes facility 350, and facilities 330, 340, and 350 form part of a state system 370.

Similar to facilities discussed at FIG. 2, each of the facilities 330, 340, and 350 include respective command centers 332, 342, and 352, respective data centers 336, 346, and 356, and respective workstations 334, 344, and 354. The resource utilization server 202 may receive plurality of data from each of the facilities 330, 340, and 350, via one or more of workstations, command centers, client devices, and data centers. Data feeds 320 from the facilities 330, 340, and 350 may be flat file data fields that do not include fully-identified patient data. Details of providing flat file data fields to the resource utilization server for generating resource utilization dashboards will be further described below.

Responsive to receiving data feeds from the respective facilities, the resource utilization server 202 may generate and update the one or more resource utilization dashboards, and communicate the one or more dashboards to the requesting workstation and/or client devices (including command center workstation, medical device workstation, and data center).

Figure 4:
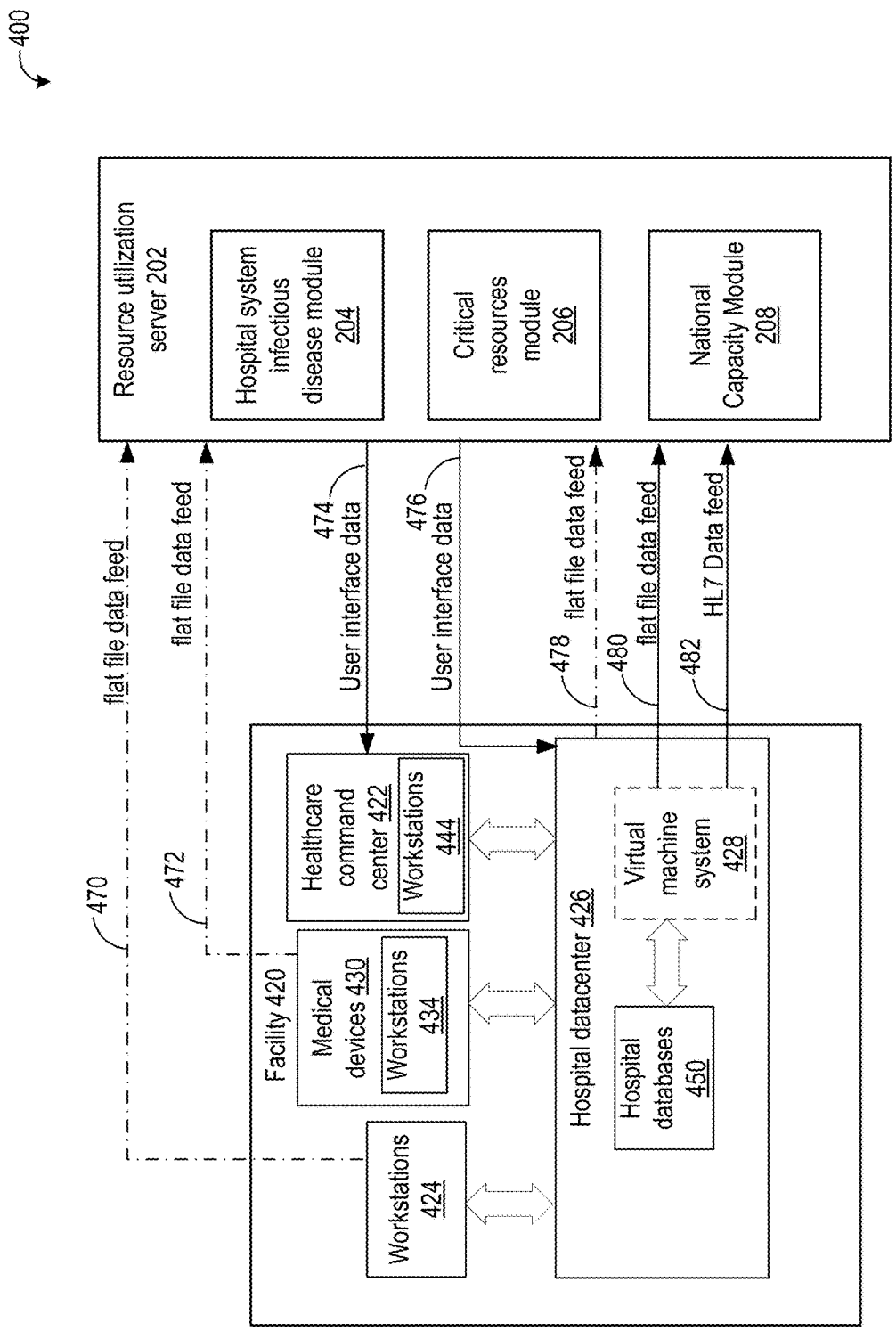
FIG. 4 schematically shows one or more data feed types generated from a facility for determining resource utilization.

Next, FIG. 4 shows a schematic illustration of an example resource utilization system 400 showing resource utilization data transmission between a facility 420 and resource utilization server 202. Facility 420 is a healthcare facility, such as a hospital, and is similar to facilities discussed at FIGS. 2 and 3, and thus may include components similar to those described at FIGS. 2 and 3. Briefly, facility 420 includes a hospital data center 426 comprising one or more hospital databases 450. Further, facility 420 may include a plurality of units, each unit including a plurality of rooms (not shown). Further, each room may include one or more beds (not shown). Facility 420 may further include workstations 424, which may be EMR workstations, workstations 434 communicatively coupled to medical devices 430, and workstations 444 in the healthcare command center 422. Other type of workstations within the facility that are utilized for one or more of patient health management, and resource utilization (including critical resource utilization) are also within the scope of the disclosure.

Further, the hospital data center 426 may be provisioned with a virtual machine system 428 including a plurality of server systems for accessing and transmitting data feeds from one or more of the hospital databases 450 and workstations 424, 434, and 444.

In one embodiment, one or more of patient data, such as infectious disease data, hospital resources utilization data, such as critical resources utilization data, and hospital resource inventory data, such as critical resource inventory data, are transmitted to the resource utilization server 202 via one or more of HL7 data feed 482 and flat file data feed 480, via virtual machine system 428, provisioned within the hospital data center 426. For example, EMR data may be transmitted via HL7 data feeds. HL7 data may be one or more of fully-identified data and filtered data (without patient identification information). Flat file data feed 480 may include specified fields and corresponding data extracted from EMR, critical resources, and infectious disease data pertaining to patients and resources within the facility 420. Exemplary flat file fields are shown at FIG. 9. Further, details of generating and transmitting flat files are further described below at FIGS. 6A, 7A, and 8A.

While the above exemplary embodiment describes flat file data transmitted via the virtual machine system, in another embodiment flat file data may be transmitted without utilizing the virtual machine system 428. Transmission of flat file data feeds are shown as dot dash dot lines. For example, flat file data feed 478 may be generated and transmitted by the hospital data center 426, via one or more datacenter processors. In another example, one or more workstations, including workstations 424 and 434, may process and transmit flat file data 470 and 472, to the resource utilization server 202. The flat file transmission may be via a suitable file transfer protocol, such as secure file transfer protocol (SFTP).

The resource utilization server 202 may receive a plurality of data feeds from the facility, via one or more of virtual machine system 428, data center 426, and plurality of workstations 424, 434, and 444. The resource utilization server 202 may process the data and generate user interface data, which may be transmitted to one or more of hospital data center 426 and healthcare command center 422, as indicated by 474 and 476. The processing of the plurality of data feeds may be performed by one or more of a hospital system infectious disease module, a critical resources module, and a national capacity module, and may be performed automatically and/or based on client request. The user interface data may then be rendered via a graphical user interface on a display portion of a client device, which may be one or more of workstations 424, 434, and 444, or any appropriate client display device.

Figure 5:
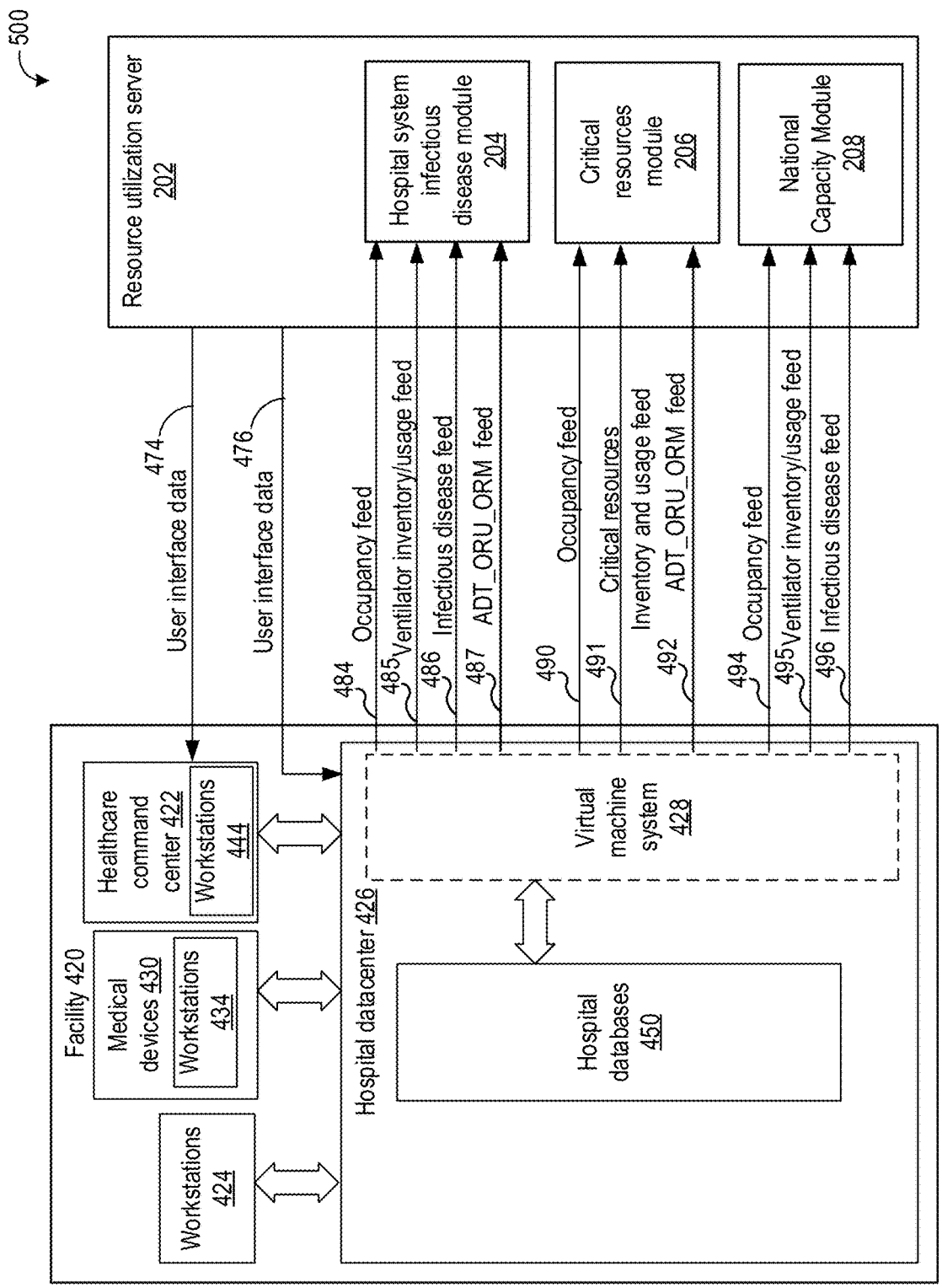
FIG. 5 schematically shows a plurality of data feeds generated from a facility for determining resource utilization.

FIG. 5 is a schematic illustration 500 of a plurality of data feeds transmitted via virtual machine system 428 for the resource utilization system 400 (shown at FIG. 4). As discussed at FIG. 4, the plurality of data feeds to resource utilization server 202 may include HL7 data feed 482 from Electronic Medical Record (EMR) systems for the facility 420, and flat file data feed 480.

In particular, the hospital system infectious disease module 204 may receive an occupancy data feed 484, a ventilator inventory and usage data feed 485, an infectious disease data feed 486, and an ADT_ORU_ORM data feed 487. In one example, the occupancy data feed 484 may include a bed master template flat file data feed including bed inventory data for the facility 420, and a bed block flat file data feed including bed usage data for the facility 420. The ventilator inventory and usage data feed may 485 may include a ventilator inventory flat file data feed and a ventilator usage flat file data feed, wherein the ventilator usage flat file data feed may be generated based on ventilator usage data obtained by method 1000 described at FIG. 10. The infectious disease data feed 486 may include patient under investigation (PUI) data feed and infected patient data feed, wherein the PUI data and the infected patient data may be obtained based on method 1100 described at FIG. 11.

The ADT_ORU_ORM data feed 487 is the HL7 data feed, and may include admissions, discharge, and transfer (ADT) data feed, order entry message (ORM) data feed (including infectious disease lab orders, ventilator application orders, and discontinuation orders), and observation result (ORU) data feed (including infectious disease test results, ventilator usage data, such as start time, stop time, type, identifier). In one example, the ADT_ORU_ORM data feed 487 is a fully-identified patient data feed, including patient information (e.g., patient name) and patient demographic information. In another example, ADT_ORU_ORM data feed 487 is a data feed without fully-identified patient data, wherein the fully identified patient data is not provided to the server. In this case, patient's personal information, and demographic information may not be provided. Further, in one embodiment, the fully-identified data feed and the data feed without fully-identified information may be filtered to extract specific data for one or more of critical resources and infectious disease, by the hospital datacenter processor for example, and the extracted data may be provided to the resource utilization server 202 via the virtual machine system. In this way, by generating specific data feeds for one or more of critical resources and infectious diseases, processing of the data feeds is expedited, and user interface data may be generated and updated in real-time or near real-time.

The infectious disease module 204 may process the received data feeds 484, 485, 486, and 487, and generate infectious disease user interface data. The infectious disease user interface data may be rendered in an infectious disease graphical user interface (GUI) at one or more workstations and client devices associated with the facility. Exemplary infectious disease GUIs are illustrated and described at FIGS. 29-34. Briefly, the generated infectious disease user interface data may include, for each facility and/or for the hospital system including one or more facilities, patient load data, status data of critical care (CC) and cardiovascular (CV) targeted bed occupancy at the CC and CV units, patient test and observation activity with regards to infectious disease, various environmental services (EVS) data for the CC and CV beds, ventilator usage with respect to individual patients, and bed occupancy with respect to infectious disease patients. In this way, the infectious disease module and the infectious disease GUI may provide critical resources utilization (including critical units, ventilators) and patient information during endemic, epidemic, and pandemic situations affecting public health at a system level and/or facility level, in real-time or near real-time, so as to expedite decision making and increase efficiency of utilization of resources, enable real-time and near-real time need assessment, and organize mobilization of critical resources.

Further, FIGS. 29-34 is illustrated for COVID-19 infectious disease. It will be appreciated that the infectious disease module and the infectious disease GUI may be implemented for any infectious and/or communicable disease or any disease or situation (e.g., radioactive waste exposure, toxic gas exposure) causing public health concern, and for corresponding relevant critical care resource utilization.

The critical resources module 206 may receive an occupancy data feed 490, a critical resources inventory and usage data feed 491, and an ADT_ORU_ORM data feed 492. The occupancy data feed 490 may include a bed master template flat file data feed including bed inventory data for the facility 420, and a bed block flat file data feed including bed usage data for the facility 420. The critical resources inventory and usage data feed 491 may include one or more critical resource inventory flat file data feed and corresponding one or more critical resource usage flat file data feed. In one example, the critical resource may include a ventilator, and accordingly, the ventilator usage flat file data feed may be generated based on ventilator usage data obtained by method 1000 described at FIG. 10. In some examples, therefore, the critical resources inventory and usage data feed 491 may include the ventilator inventory and usage data feed 495, which is described below. The ADT_ORU_ORM data feed 492 is the HL7 data feed, and is similar to the ADT_ORU_ORM data feed 487 as discussed above, with the exception that the ORM data feed may not include lab orders and the ORU data feed may not include infectious disease results. In still other examples, the ADT_ORU_ORM data feed 492 may only include the ADT data feed (e.g., including admissions, discharge, and transfer) and may not include the ORM or ORU feeds. Further, the ADT_ORU_ORM data feed may be a filtered data feed that may include fully identified data or data without fully identified patient information as discussed above. Other embodiments where the ADT_ORU_ORM data feed to the resource utilization server (that is, to any of the modules 204, 206, and 208) is not filtered to extract specific resource utilization and/or infectious disease information are also within the scope of the disclosure.

The critical resources module 206 may process the received data feeds 490, 491, and 492, and generate critical resources user interface data. For example, the critical resource user interface data may include critical resource usage data for critical care units including ICU, PCU, MT/MS units, OBS units, negative pressure units, and ventilators for the facility. The critical resources user interface data may be rendered in critical resources graphical user interface (GUI) at one or more workstations and client devices associated with the facility. Exemplary critical resources GUIs are illustrated and described at FIGS. 22-28.

Further, the national capacity module 208 may receive an occupancy data feed 494, a ventilator inventory and usage data feed 495, and an infectious disease data feed 496. As discussed above, the occupancy data feed 494 may include the bed master template flat file data feed including bed inventory data for the facility 420, and the bed block flat file data feed including bed usage data for the facility 420. The ventilator inventory and usage data feed 495 may include the ventilator inventory flat file data feed and the ventilator usage flat file data feed, wherein the ventilator usage flat file data feed may be generated based on ventilator usage data obtained by method 1000 described at FIG. 10. Additionally, as explained above, the ventilator inventory and usage data feed 495 may be sent to/used by the critical resources module 206. The infectious disease data feed 496 may include the patient under investigation (PUI) data feed and the infected patient data, wherein the PUI data and the infected patient data may be obtained based on method 1100 described at FIG. 11A.

The national capacity module 208 may process the received data feeds 494, 495, and 496, and generate national capacity user interface data. The national capacity user interface data may be rendered in a national capacity graphical user interface (GUI) at one or more workstations and client devices associated with the facility. Exemplary national capacity GUIs are illustrated and described at FIGS. 15-21 and 37-44.

In one example, the infectious disease module 204, the critical resources module 206, and the national capacity module 208 may utilize only flat file data feeds and/or filtered HL7 data feeds to generate corresponding user interface data for the infectious disease GUI, the critical resources GUI, and the national capacity GUI. In this way, real time data or near real-time data may be transmitted, and processed to provide near real-time updates regarding critical resources and infectious disease progression.

While a single facility is shown here, it will be noted that the infectious disease module 204, the critical resources module 206, and the national capacity module 208 may receive data from plurality of facilities at various demographic hierarchical levels (e.g., hospital system, state, regional, and national). In one embodiment, when a number of facilities increase above a threshold and/or a processing time increases above a threshold, the modules 204, 206, and 208 may utilize only flat file feeds and/or filtered HL7 data feeds to generate user interface data for the respective GUIs.

It is to be appreciated that the resource utilization server 202 may receive some data via HL7 and other data via flat file, but within the same module (e.g., within the critical resources module 206), the method of receiving a specific data element is consistent across hospitals (e.g., for a given data element such as bed inventory data, that data element is received in HL7 or flat file from all hospitals, not HL7 from one hospital and flat file from another hospital for the same data element). Across modules, however, it can vary whether a data element is received via HL7 or flat file.

In some embodiments, a resource utilization server, such as the resource utilization server 202 discussed at FIGS. 2-5, and the resource utilization server system 102 discussed at FIG. 1, may be implemented by a virtual machine system comprising a plurality of virtual machines, wherein the virtual machine system is provisioned within a datacenter of a healthcare facility. Each of the plurality of the virtual machines may be configured as computing systems including one or more processors and memory.

Figure 6A:
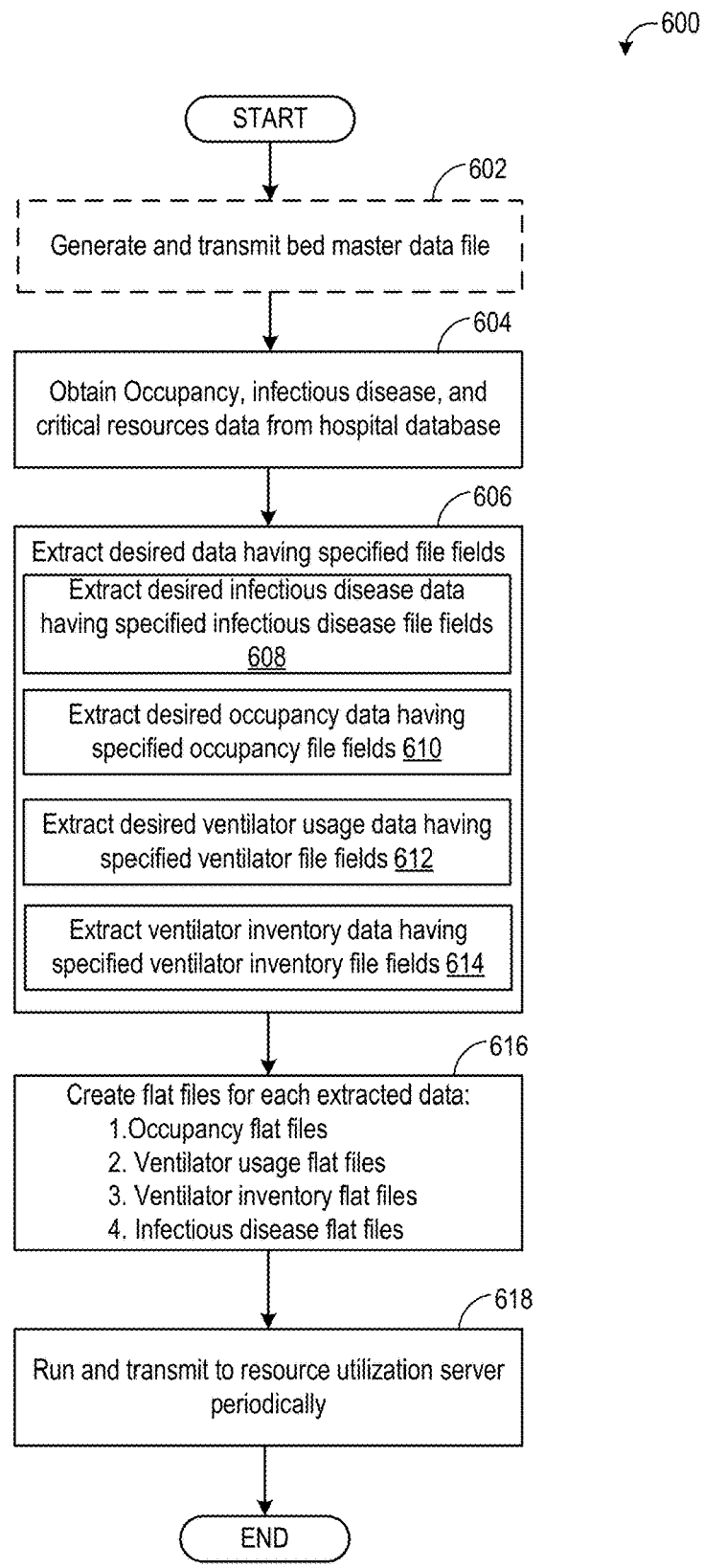
FIG. 6A is a flowchart illustrating an example method for generating data feeds utilized by a collaborative resource utilization system to generate a national capacity graphical user interface (GUI), according to a first embodiment.

FIG. 6A is a flow chart illustrating a high-level method 600 for generating one or more data feeds for a national capacity module, such as national capacity module 208 at FIG. 2-5, of the resource utilization server 202, according to one embodiment of the present disclosure. In particular, the method 600 may be utilized to generate flat file data feeds for the national capacity module. For example, for facilities that are not part of a data-sharing network, the method 600 may be implemented to generate flat file feeds with specified feeds (example fields are shown at FIG. 9) and do not include fully identified patient information, and transmit the generated flat file data to the national capacity module of the resource utilization server.

The method 600 and other methods 650, 700, 750, and 800 described herein may be executed by a processor, such as a processor at a hospital data center 426, a processor for a workstation, such as workstations 432, 434, and 444 at FIGS. 4 and 5, an edge device within or coupled to hospital network, or any appropriate combination thereof. While the present method 600 and other methods 650, 700, 750, and 800 herein are described primarily with respect to FIGS. 4 and 5, it will be appreciated that the method 600 and the other methods may be implemented by other systems and components without departing from the scope of the present disclosure.

Method 600 begins at 602. At 602, a bed master data file may be generated and transmitted to a resource utilization server, such as resource utilization server 202. The bed master data file may include bed data for the facility and may include specified fields, including system name, hospital identification (ID), Unit ID, Unit display name, Unit type, Room ID, Room display name, Bed ID, Bed display name, Service (e.g., cardiac), Level of care group (e.g., adult ICU), Vent capable, Negative pressure, Private, and Active. In one example, the bed master data for the specified fields may be extracted from a bed inventory database for the facility. The bed master data may be updated over a greater period or based on user request. For example, during public health situations, it may be necessary to convert one or more units to critical care units to handle patient load, and thus may need to be updated over a greater period (e.g., weeks, months) based on the on-going public health situation and overall patient load for the facility.

Next, At 604, occupancy data, infectious disease data and critical resources data, including ventilator data, may be obtained from one or more hospital databases.

At 606, the method 600 may extract desired data based on specified file fields. Extracting desired data includes, at 608, extracting desired infectious disease data based on specified infectious disease file fields; at 610, extracting desired occupancy data based on specified occupancy file fields; at 612, extracting desired ventilator usage data based on specified ventilator file fields; and at 614, extracting ventilator inventory data based on specified ventilator inventory file fields.

The desired infectious disease file fields may include a time stamp field, a system field, a facility field, a unit field, a bed field, and a flag field for infectious disease status. The flag field may include an indication of patient infectious disease state, such as PUI or infectious disease positive. The PUI data and the infectious disease positive data may be obtained based on infectious disease data obtained by method 1100. For example, the health care/hospital database processor may execute method 1100 described with respect to FIG. 11A to determine a number of PUI and a number of infectious disease positive patients at the facility, and store the processed data within the database. The desired infectious disease data may thus be extracted from the processed data. In this way, for facilities that are not part of a data-sharing network, the facilities may not share patient personal information, but only the desired infectious disease data (that may be helpful in critical resource planning, monitoring public health and disease progression) may be extracted and sent to the resource utilization server for further data aggregation, processing and rendering user interfaces.

The desired occupancy data may include Timestamp of record field, System field, Facility field, Unit field, Room field, Bed field, isOccupied field, isBlocked field, and isNegativePressure field. The data values for each of the above fields may be extracted from one or more of the hospital database(s) and EMR.

The desired ventilator data fields may include System Name, Facility Name, Category (e.g., invasive or non-invasive), serial number, model and operational status. In one example, the healthcare/hospital database processor may execute method 1000 of FIG. 10 to determine the ventilator operational status data based on EMR data. The desired ventilator status data for the operational status may be extracted from the processed data. In another example, the desired ventilator data fields may further include vent start time and vent stop time, and one or more other input fields corresponding to data that may be required for the resource utilization server to execute method 1000. The ventilator data for resource utilization server processing which may be obtained from EMR data without any additional personal patient information.

The desired ventilator inventory data fields may include System Name, Facility Name, Category (e.g., invasive or non-invasive), serial number, model, which may be extracted, for example, from a hospital ventilator inventory database.

Example desired occupancy flat file fields, desired infectious disease flat file fields, and example ventilator inventory flat file fields are shown at FIGS. 9 at 920, 940, and 960 respectively. Upon extracting data corresponding to the desired fields, at 616, occupancy flat files, ventilator usage flat files, ventilator inventory flat files, and infectious disease flat files may be generated. The flat files may be provided in a comma separated value format, for example.

Next, the generated flat files may be transmitted to the resource utilization server periodically for generating national capacity user interface data. In one example, the flat files may be transmitted via SFTP. The time period for periodic transmission may be such that the data feeds are transmitted in near-real time. In one example, the data feeds may be transmitted at every three minutes. In another example, the time period may be less than 3 minutes or more than 3 minutes, but less than one hour (60 minutes), so that the interface data is updated constantly. For example, the time period may be every 30 seconds. Further, it may be noted that one or more fields, specifically, the System, Facility, Unit, Room, and Bed fields in each of the occupancy, ventilator, and infectious disease flat files correlate with the System, Facility, Unit, Room, and Bed fields in the bed master template. That is, for a given bed, the data in the generated flat file fields should be same as those provided in the bed master template.

Figure 6B:
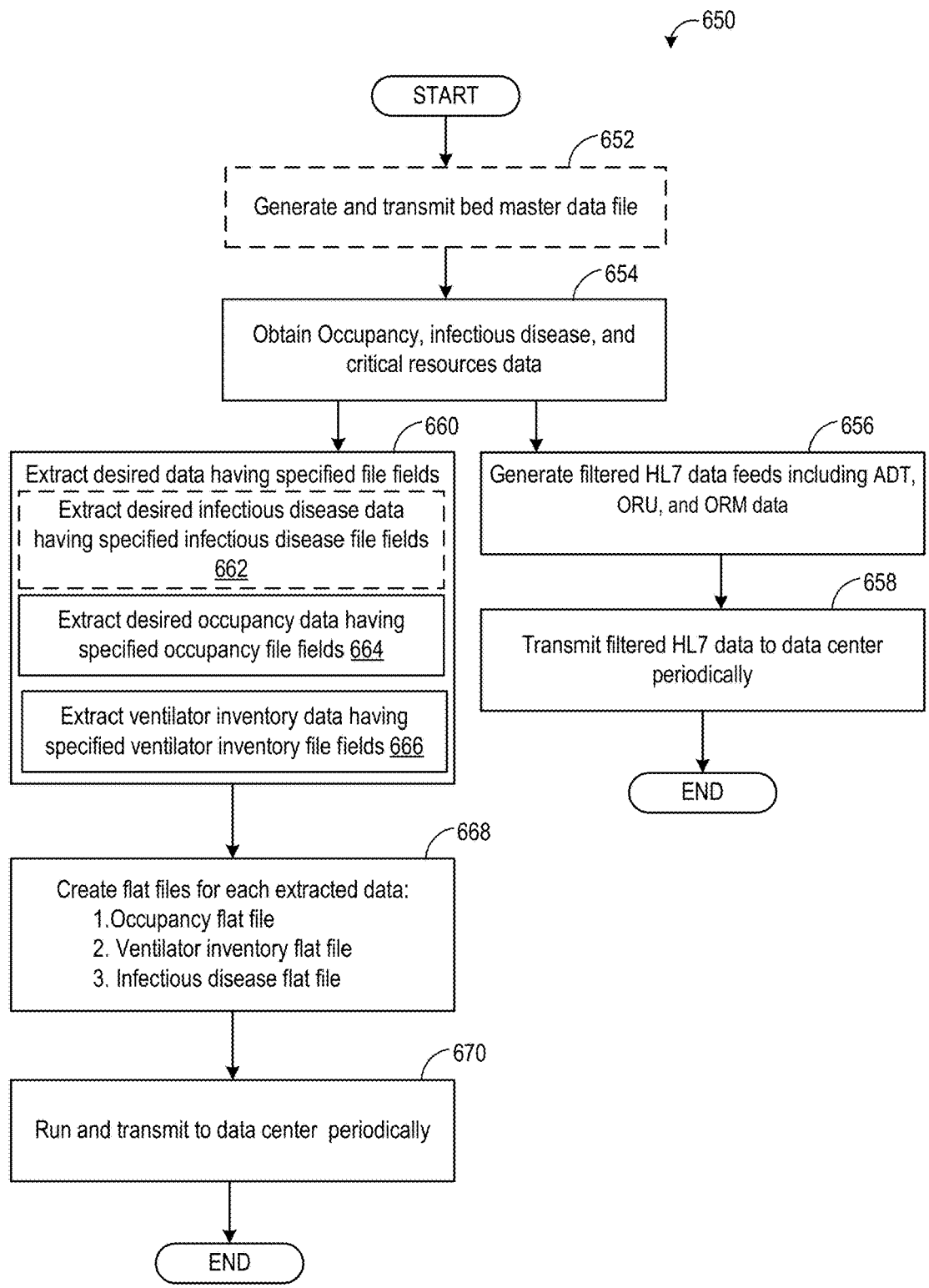
FIG. 6B is a flowchart illustrating an example method for generating data feeds utilized by a collaborative resource utilization system to generate a national capacity GUI, according to a second embodiment.

FIG. 6B is a flow chart illustrating a high-level method 650 for generating one or more data feeds for a national capacity module, such as national capacity module 208 of FIGS. 2-5, according to a second embodiment. Specifically, method 650 describes generating HL7 data feeds and flat file data feeds. For example, facilities that are part of data-sharing network may transmit HL7 data feeds from EMR in addition to flat file data feeds. In this embodiment, the method 650 is implemented for generation of filtered HL7 data feeds in addition to flat file data feeds.

The method begins at 652. Steps 652 and 654 are similar to steps 604 and 604 at FIG. 6A, and will not be described herein for brevity.

Next, at 660, the method 650 includes extracting desired data based on specified file fields 660. Extracting desired data includes, at 662, extracting desired infectious disease data based on specified infectious disease file fields; at 664, extracting desired occupancy data based on specified occupancy file fields; and at 666, extracting ventilator inventory data based on specified ventilator inventory file fields. Steps 662, 664, and 666 are similar to steps 608, 610, and 614 at FIG. 6A.

Next, similar to step 616 of FIG. 6A, at 668, method 650 includes generating flat files for each extracted data. Specifically, step 668 includes generating occupancy flat file, ventilator inventory flat file, and infectious disease flat file.

Next, at 670, the generated flat files may be transmitted periodically to the hospital data center, for example, to a virtual machine system provisioned within the data center. The virtual machine system may subsequently transmit the data to the resource utilization server.

Returning to step 654, upon obtaining occupancy, infectious disease, and critical resource data, method 650 may proceed to 656 in parallel. At 656, the method 650 includes generating filtered HL7 data feeds including one or more of filtered ADT, filtered ORU, and filtered ORM data. Filtered HL7 data feeds may include or may not include fully-identified patient data. The unfiltered HL7 data feeds may be obtained from EMR data, which may be obtained from a hospital EMR database at the hospital data center, and/or from EMR workstation processing and storage systems having non-transitory memory, and one or more filters may be applied to obtain filtered ADT, ORM, and ORU data.

In some embodiments, filtered ADT data may include admissions, discharge and transfer data without personal patient information and demographic information. In one example, the filtered ADT data feed may be utilized by the national capacity module to calculate an admission rate, discharge rate, and transfer rate over a desired period of time for critical care units. Filtered ORM data feed for national capacity module may include ORM lab order data relating to infectious disease testing, and ORM critical resources data, including ventilation application orders and discontinuation orders. Similar to filtered ADT data, filtered ORM data may not include patient personal information and patient demographic information. Further, filtered ORU data feed, without patient personal information and demographic information, may include ORU lab data feed and ORU ventilator flow data feed. The ORU lab data feed may include test results observed from infectious disease testing orders, and ventilator operational data, including ventilator start time, ventilator stop time, ventilator identifier and ventilator type.

In other embodiments, fully-identified HL7 data feeds may be generated. However, even for fully-identified HL7 data feeds, one or more filters may be applied to extract specific critical resource utilization data and infectious disease data. For example, a fully-identified HL7 data feed may include filtered ventilation utilization data, and thus ventilator start time, ventilator stop time, ventilator type, and ventilator identity may be extracted, and other ventilation information may not be included so as to increase processing speed by the resource utilization server. For example, filtered ADT data may include filtered admissions, discharge and transfer data with fully-identified patient information, such as personal patient information and demographic information. Filtered ORM data feed for national capacity module may include filtered ORM lab order data relating to infectious disease testing, and filtered ORM critical resources data, including ventilation application orders and discontinuation orders. Similar to filtered ADT data discussed in this embodiment, filtered ORM data may include patient personal information and patient demographic information. Similarly, filtered ORU data feed may include patient personal information and demographic information.

Upon generating filtered ADT, ORU, and ORM data, method 650 includes, at 658, transmitting the generated filtered data via the virtual machine system to the resource utilization server. The method 650 then ends.

In this way, by providing specific data to the resource utilization server, processing at the server to generate user interface data is greatly improved, thereby providing real-time or near-real time data updates via the GUIs described herein.

FIG. 6A describes generating flat file data feeds, and FIG. 6B describes generating flat file data feeds and filtered HL7 data feeds. In a third embodiment, fully-identified and unfiltered HL7 data feeds including patient personal and demographic information may be transmitted to the resource utilization server. In some examples, the national capacity module may utilize only the flat file data feeds (e.g., the occupancy flat file, ventilator inventory flat file, and infectious disease flat file).

Figure 7A:
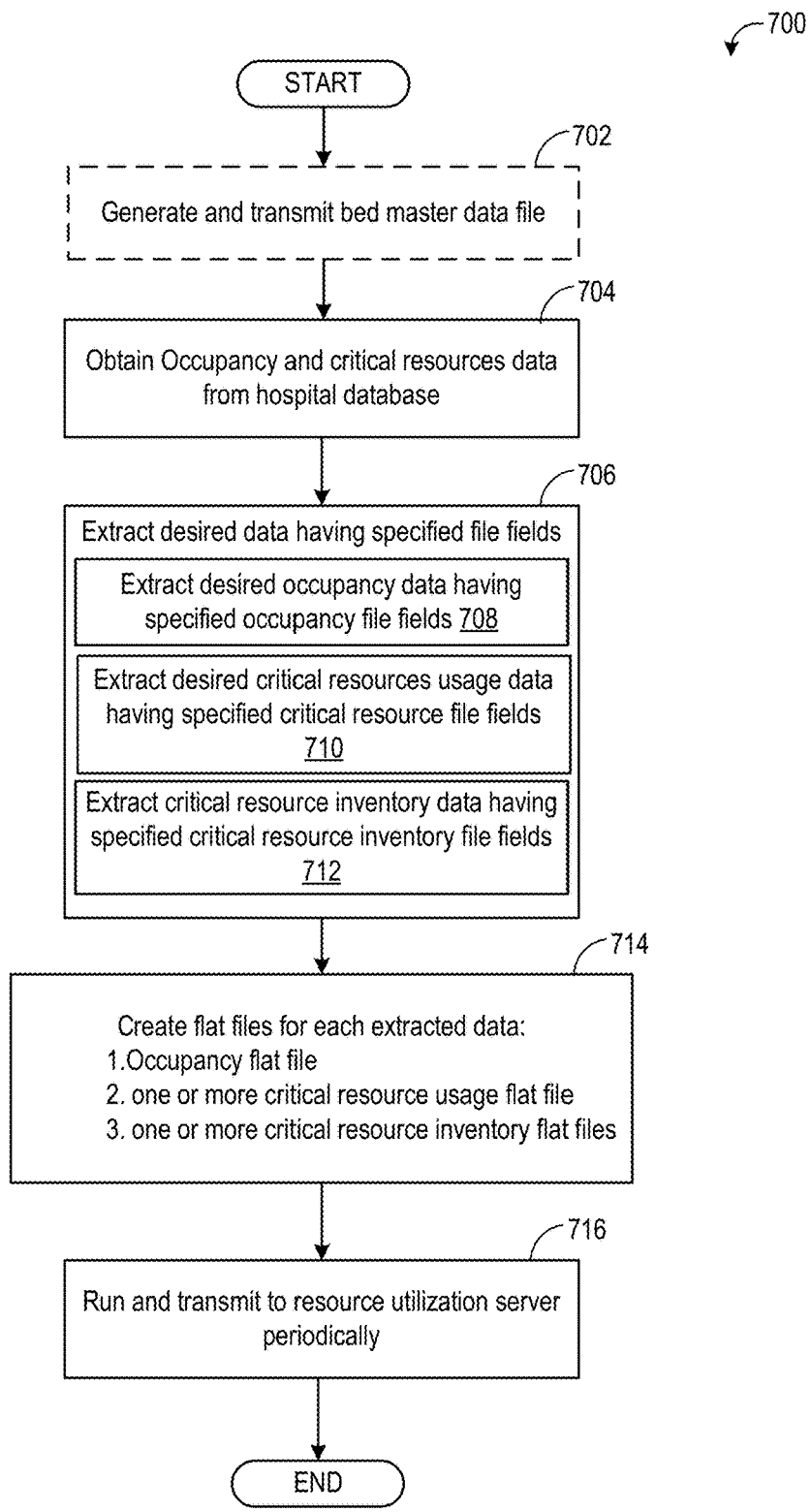
FIG. 7A is a flowchart illustrating an example method for generating data feeds utilized by a collaborative resource utilization system to generate a critical resource GUI, according to a first embodiment.
Figure 7B:
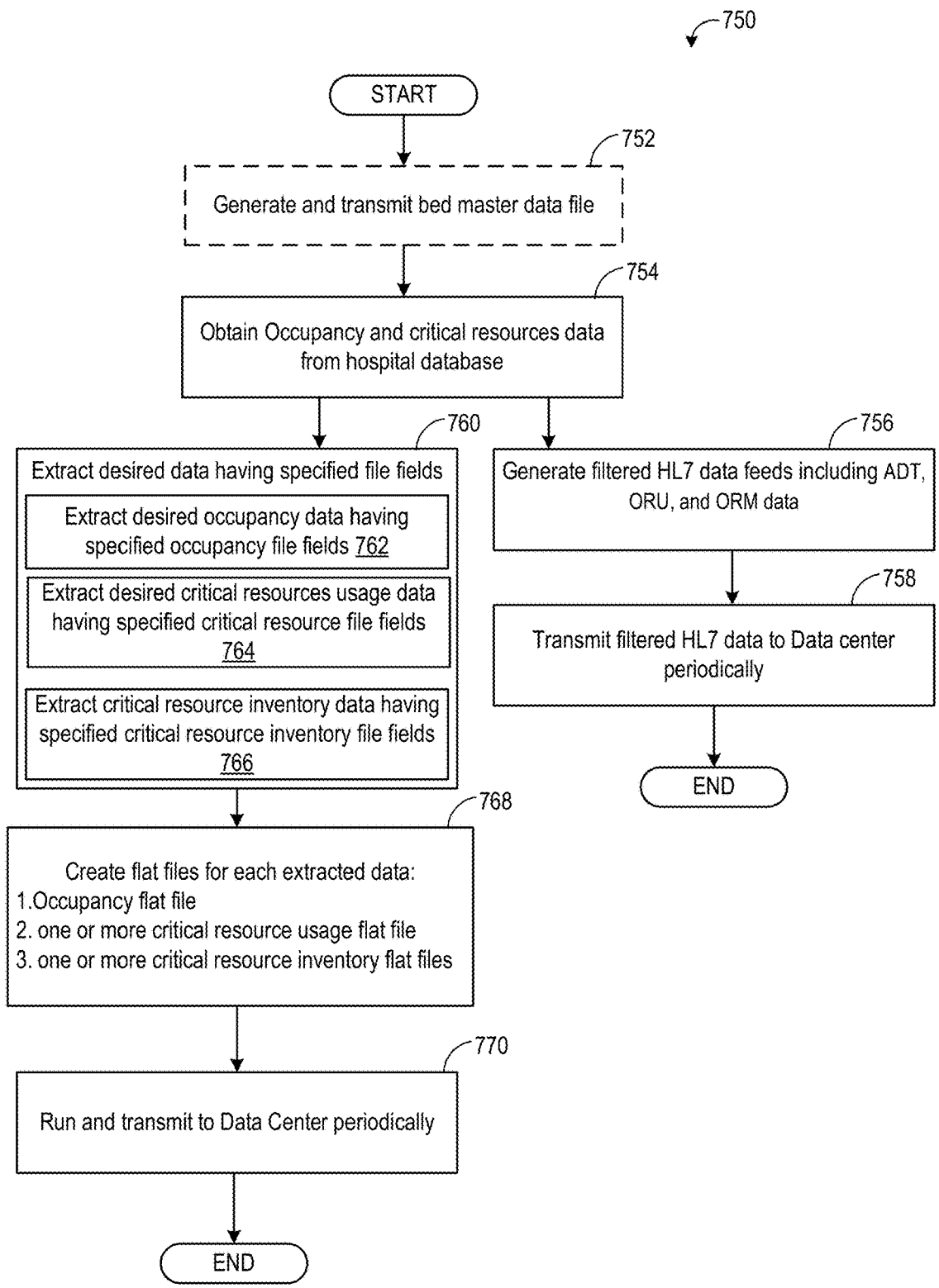
FIG. 7B is a flowchart illustrating an example method for generating data feeds utilized by a collaborative resource utilization system to generate a critical resource GUI, according to a second embodiment.
Figure 8:
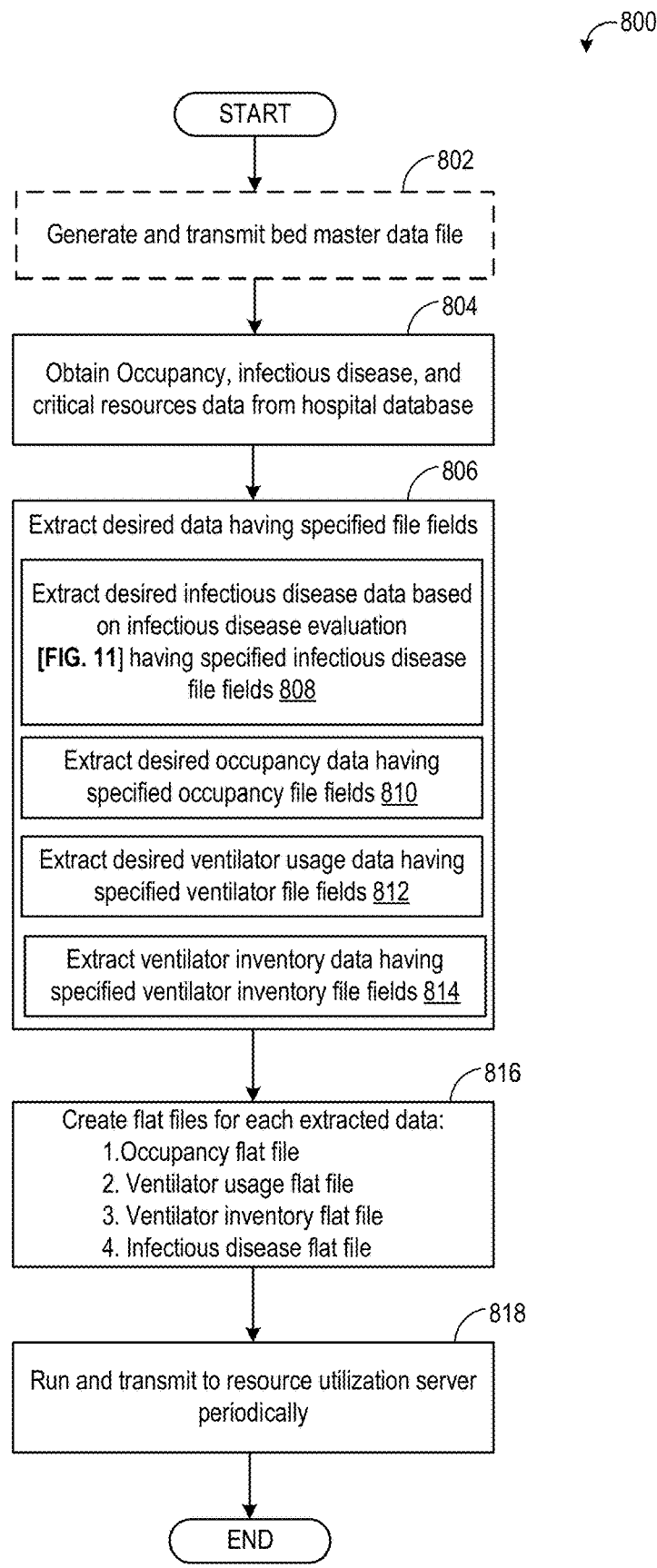
FIG. 8 is a flowchart illustrating an example method for generating data feeds utilized by a collaborative resource utilization system to generate an infectious disease GUI, according to a first embodiment.
Figure 9:
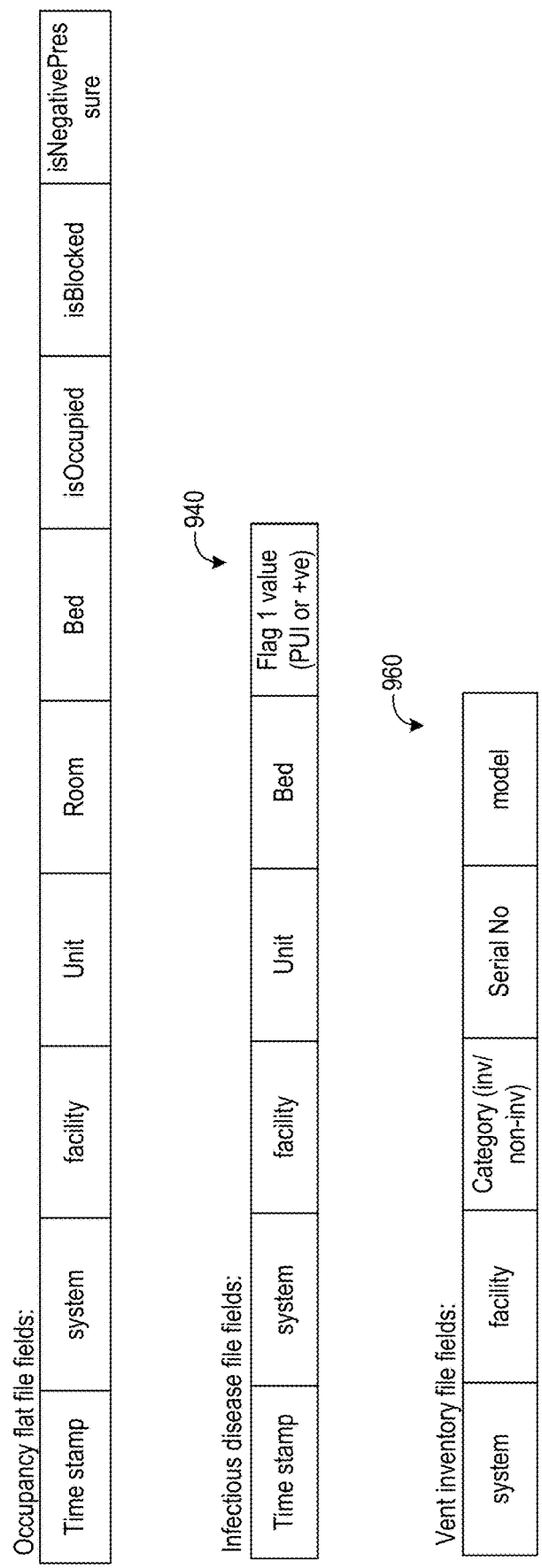
FIG. 9 is a schematic showing example flat file feeds for data feeds provided to a resource utilization server of a collaborative resource utilization system.

While FIGS. 6A and 6B describe generating data feeds for national capacity module for generating user interface data for the national capacity GUI, FIGS. 7A and 7B describe a first embodiment and a second embodiment respectively for generating data feeds for a critical resource module of the resource utilization server; and FIG. 8 describes a first embodiment for generating flat file data feeds for an infectious disease module of the resource utilization server.

Specifically, FIG. 7A describes generating flat file data feeds. Steps 702, 704, 708, and 716 are similar to steps 602, 604, 610, and 618. With regard to step 710 and 712, critical resources utilization and critical resources inventory data based on corresponding specified flat file feeds may be obtained. If the critical resource is ventilators, steps 710 and 712 are similar to 612 and 614. It will be appreciated that other critical resources data, may be similarly processed.

Further, with respect to step 708, the desired occupancy data may include additional indication with respect to critical care units. For example, the desired bed occupancy data may include indications of ICU, MCU, negative pressure units, etc.

Upon extracting desired flat file data, at 714, the method 700 may generate occupancy flat files, one or more critical resource flat files, and one or more critical resource inventory flat files.

Turning now to FIG. 7B, a second embodiment for generating flat file and HL7 data feeds for critical resource module is shown. Steps 752, 754, 760 (including steps 762, 764, and 766), 768, and 770 are similar to steps 702, 704, 706, 714, and 716. Additionally, the filtered HL7 data generation is performed at step 756. At 756, the method 750 includes generating filtered ADT, ORM, and ORU data, and at 758, transmitting the filtered HL7 data to the data center periodically. Generation of filtered HL7 data is similar to filtered data feed for national capacity module at step 656 at FIG. 6B, except that for the critical resource module, ORM and ORU infectious disease lab testing and results are not included.

Further, as discussed with respect to FIG. 6B, the second embodiment at FIG. 7B may not include fully identified patient data. Further, a third embodiment for generating data feeds for critical resources may include fully identified filtered HL7 data in addition to flat file data described at FIG. 7B.

Next at FIG. 8, an example method 800 for generating flat file data for the infectious disease module, according to a first embodiment, is shown. Steps 802, 804, 810, 812, 814, 816, and 818 are similar to steps 602, 604, 610, 612, 614, 616, and 618 at FIG. 6A. With regard to step 808 of step 806, the desired infectious disease data may be extracted based on one or more additional infectious disease flat file fields. The one or more additional infectious disease flat file fields may include infectious disease data generated based on infectious disease evaluation discussed at FIGS. 11A-11C. For example, the facility/hospital data processor may acquire one or more previous and current EMR data corresponding to infectious disease tests and results, process it based on method 1100 described at FIG. 11, and output infectious disease status of the patient. In one example, the additional data fields may include information as to whether the patient was tested positive at least once or has never tested positive. The additional data fields may include data fields that correspond to patient data that may be utilized to determine patient load and patient activity by the infectious disease module which may be rendered in the infectious disease interface as shown at FIGS. 29-32 and 34. The additional data fields may include an infectious disease bed maintenance data field (e.g., EVS applied), under which an infectious disease bed maintenance status (e.g., True or False) may be provided.

A second embodiment for the generation of flat file feeds and filtered HL7 data feeds (without fully identified patient information) for infectious resource module is similar to the generation of flat file feeds and HL7 data feeds for national capacity module discussed at FIG. 6B.

Further, a third embodiment for generating data feeds for infectious disease resources may include fully identified unfiltered HL7 data in addition to flat file data described at FIG. 8.

Figure 10:
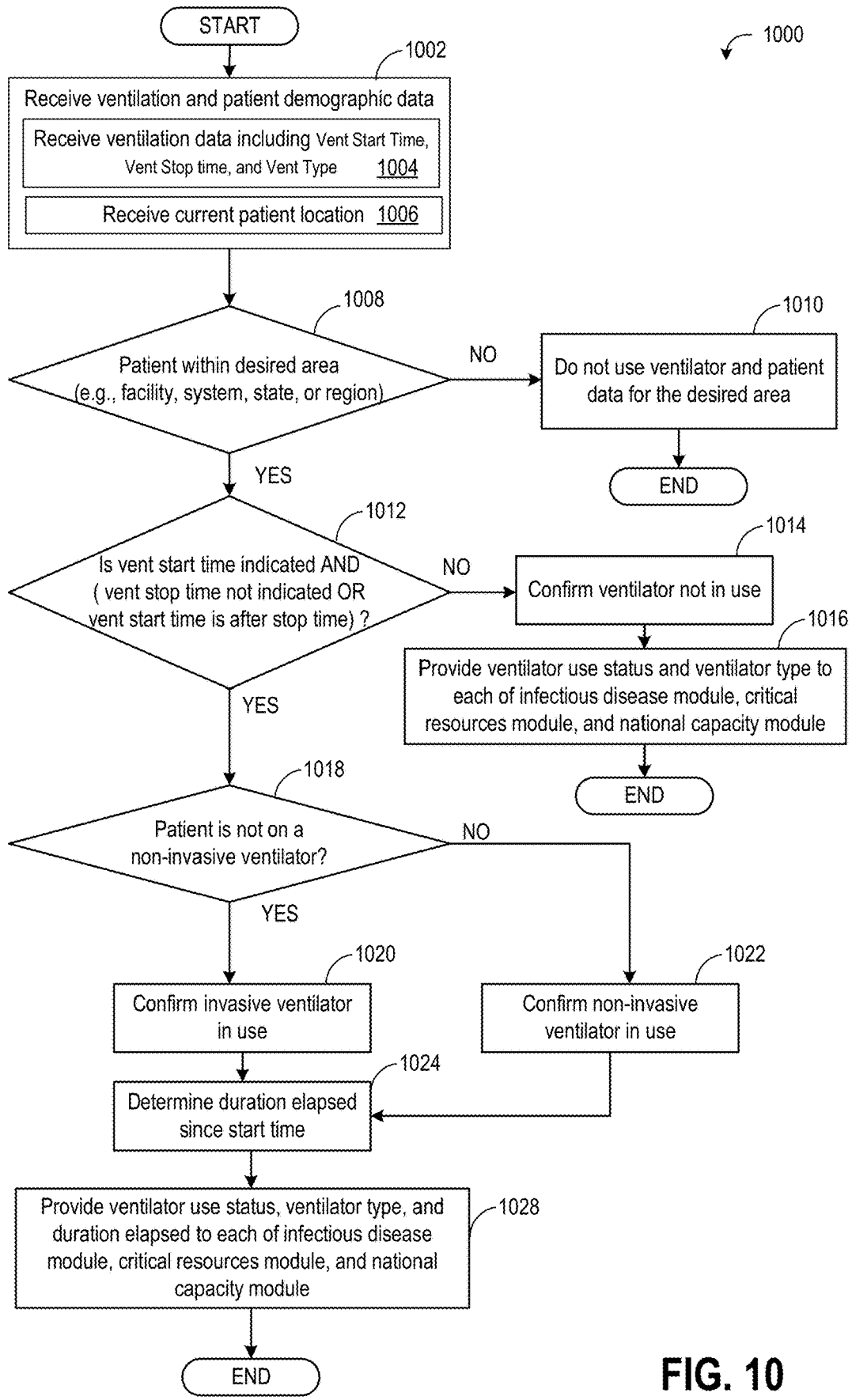
FIG. 10 is a flowchart illustrating an example method for determining a status of a ventilator.

Turning next to FIG. 10, it shows a flowchart illustrating a method 1000 for tracking ventilator usage across one or more hospitals or medical facilities. Method 1000 may be carried out according to instructions stored in memory of a computing device in communication with the one or more hospitals or medical facilities, such as resource utilization server 202. Method 1000 is described herein as being executed to detect ventilation status for a single ventilator in order to update a ventilator count for a desired geographical area. It is to be understood that method 1000 may be executed for each ventilator of a plurality of ventilators that are connected to/configured to send data to the resource utilization server.

At 1002, ventilation and patient demographic data are received. The received ventilation and patient demographic data may include a vent start time, a vent stop time, and a ventilator type (e.g., invasive or non-invasive), as indicated at 1004. The received ventilator and patient demographic data may include current patient location for a patient connected to the ventilator, as indicated at 1006. The ventilation and patient demographic data may be received via a ventilator inventory/usage data feed from a hospital datacenter, as described above with respect to FIG. 5, or other suitable data feed as described herein.

At 1008, method 1000 includes determining if the patient is within a desired area (such as a desired facility, a desired system, a desired state, or a desired region) based on the received current patient location. The desired area may be determined based on the intended destination/usage of the ventilator count. For example, if the ventilator count is for a specific hospital (e.g., to be displayed as part of a hospital-specific GUI), the desired area may be that hospital. If the ventilator count is for a specific geographical regions, such as all hospitals in a specific state, the desired area may be the specific geographical region. The desired area may be selected by a user or determined automatically by the resource utilization server based on which ventilator count the server is currently determining/updating.

If the patient is not located within the desired area, for example if the patient is located in a first hospital and the desired area is a second hospital, method 1000 may proceed to 1010 to not use the ventilator and patient data for the desired area. Method 1000 may then return. It is to be understood that the received ventilator and patient data is not discarded, but instead may be used to update the ventilator count for an area in which the patient is located. If the patient is located within the desired area, method 1000 proceeds to 1012 to determine if a vent start time has been indicated and either a vent stop time has not been indicated or a vent start time has been indicated after a vent start time. When a vent start time is indicated, an operator has commanded the ventilator to start operating (whether now or in the future), which indicates the ventilator is in use or will currently be in use. If no stop time has been indicated, it signals that long-term use of the ventilator is planned, rather than a quick usage of the ventilator for maintenance or other reasons. Thus, a combination of a start time and no stop time indicates the ventilator is in use. A vent start time being indicated after a vent stop indicates the ventilator has been restarted after being stopped, which also indicates that the ventilator is in use.

If a vent start time has not been indicated (regardless of any indications of a vent stop time), or if a vent start time has been indicated but a vent stop time has also been indicated or a vent start time after a vent stop time has not been indicated, method 1000 proceeds to 1014 to confirm that the ventilator is not in use. At 1016, the ventilator use status (e.g., not in use) and ventilator type are provided to each of an infectious disease module, a critical resources module, and a national capacity module. The ventilator use status may be used to adjust a ventilator use count/ventilator occupancy rate. For example, the ventilator use count may include a count of all ventilators in the desired area that are in use and the ventilator occupancy rate may include a proportion off all ventilators in the desired area that are in use. If the ventilator being assessed via method 1000 was previously in use (and thus counted as occupied/in use in the ventilator count/occupancy rate), the determination of 1014 that the ventilator is not in use may be applied to remove the ventilator from the ventilator count/occupancy rate. Method 1000 may then return.

Returning to 1012, if it is determined that a vent start time is indicated and either a) a vent stop is not indicated or b) a vent start time is indicated after a vent stop time, method 1000 proceeds to 1018 to determine whether the patient is on a non-invasive ventilator. If the patient is on a non-invasive ventilator (e.g., NO to the question of is the patient not on a non-invasive ventilator), method 1000 proceeds to 1022 to confirm that a non-invasive ventilator is in use, and then method 1000 proceeds to 1024 (explained below). If the patient is not on a non-invasive ventilator, (e.g., YES to the question of is the patient not on a non-invasive ventilator), method 1000 proceeds to 1020 to confirm an invasive ventilator is in use. At 1024, a duration of time that has elapsed since the indicated vent start time is determined. At 1028, the ventilator use status (e.g., in use), ventilator type (e.g., invasive or non-invasive), and duration since start time are provided to each of an infectious disease module, a critical resources module, and a national capacity module. The ventilator use status may be used to adjust a ventilator use count/ventilator occupancy rate, as described above. For example, if the ventilator being assessed via method 1000 was previously not in use (and thus counted as unoccupied/not in use in the ventilator count/occupancy rate), the determination of 1020 or 1022 that the ventilator is in use may be applied to add the ventilator to the ventilator count/occupancy rate. Method 1000 may then return.

Figure 11A:
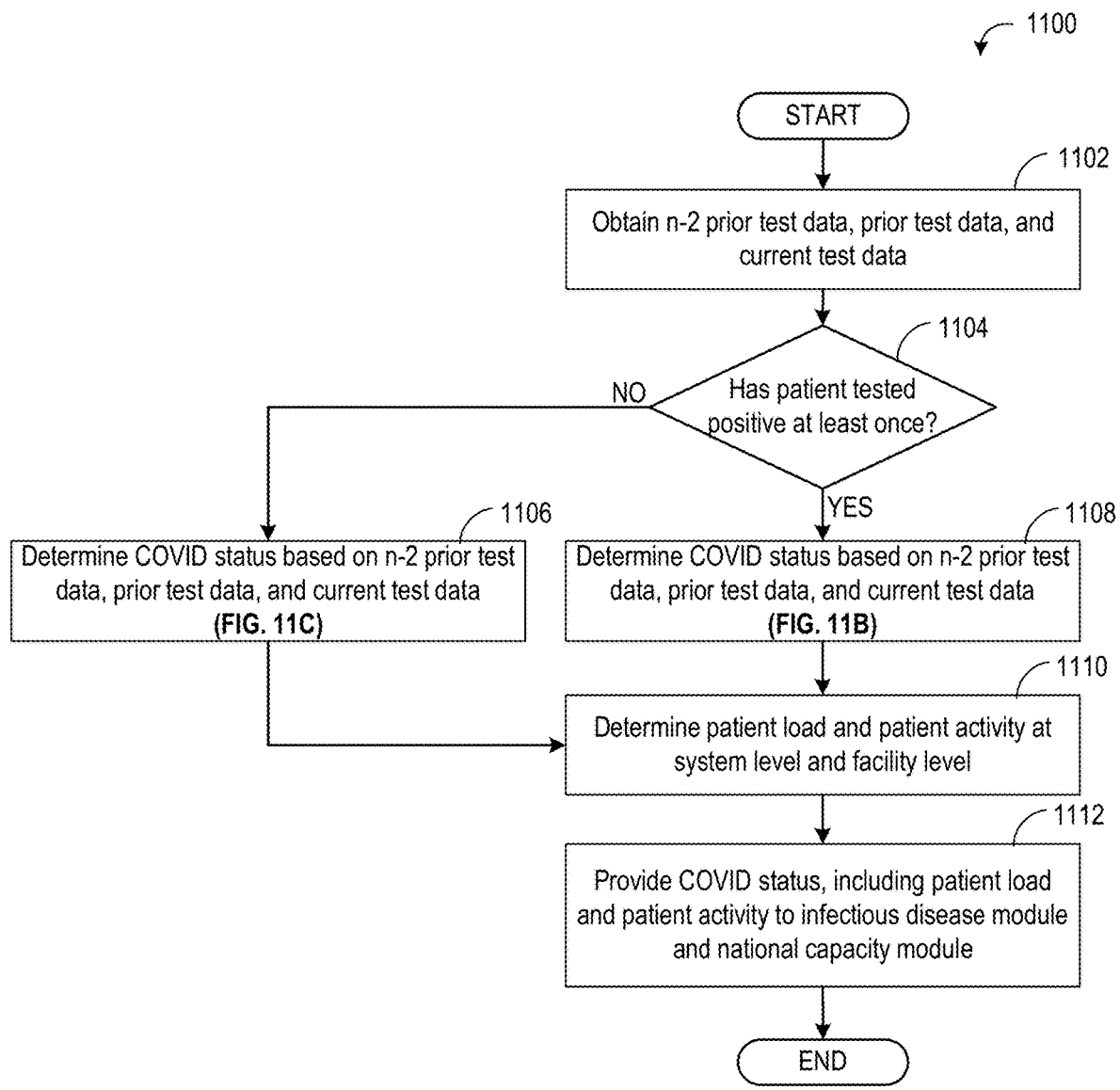
FIG. 11A is a flowchart illustrating an example method for determining a patient disease status.

FIG. 11A is a flowchart illustrating a method 1100 for determining a patient disease status. Method 1100 may be carried out according to instructions stored in memory of a computing device in communication with the one or more hospitals or medical facilities, such as resource utilization server 202. Method 1100 is described herein as being executed to determine a patient status for COVID-19, but it is to be understood that method 1100 may be executed to determine a patient status for other diseases, particularly emerging infectious diseases.

At 1102, disease test data for the patient are obtained. The test data may include test results (e.g., positive, negative, or inconclusive) for the disease (e.g., COVID-19). The test data may include data/results for a current/most-recently performed test. When available, the test data may include data/results for one or more prior tests (e.g., the prior test data and/or n−2 test data). The test data may be received via an infectious disease feed from a hospital datacenter, as explained above with respect to FIG. 5, from an HL7 data feed, and/or from a flat field data feed, as explained above with respect to FIG. 4. Each time test data for the patient is send via the data feed(s) described herein, the test data may be stored in memory on the server and obtained when indicated to determine the patient disease status.

At 1104, method 1100 includes determining if the patient has tested positive for the disease at least once, based on the obtained test data. If the patient has not tested positive at least once (e.g., all available test data for that patient includes only negative and/or inconclusive results), method 1100 proceeds to 1106 to determine COVID status based the n−2 prior test data, the prior test data, and/or the current test data, according to set of rules/logic for patients who have not tested positive. The set of rules/logic is illustrated in FIG. 11C and explained in more detail below. Briefly, due to virus incubation periods, potential testing issues, and other issues, a lack of a positive test result does not necessarily indicate a patient is negative for COVID, particularly because the system described herein may be receiving test results for patients who are hospitalized and/or otherwise suspected to have COVID. While the set of rules/logic for patients who have not tested positive for COVID include all possible testing scenarios, the rules/logic may be briefly summarized as: if the patient has a negative test result for a current test without a prior positive test result, indicating that the patient is negative for COVID responsive to a first threshold amount of time having elapsed since the current test was performed, otherwise indicating the patient is under investigation; and if the patient has an inconclusive test result for a current test without a prior positive test result, indicating the patient is under investigation until a negative test result is received or until the first threshold amount of time has elapsed since the current test was performed while the patient is asymptomatic, and then indicating the patient is negative. Method 1100 then proceeds to 1110, which will be explained in more detail below.

If it is determined at 1104 that the patient has tested positive for COVID at least once, method 1100 proceeds to 1108 to determine the patient COVID status based on the n−2 prior test data, the prior test data, and/or the current test data, according to a set of rules/logic for patients who have tested positive. The set of rules/logic is illustrated in FIG. 11B and explained in more detail below. Briefly, due to virus incubation periods, potential testing issues, disparities between symptom presentation and virus clearing timing, and other issues, the timing of when a patient positive for COVID is no longer positive may be difficult to discern via standard mechanisms (e.g., symptoms, time since symptom presentation, etc.). While the set of rules/logic for patients who have tested positive for COVID include all possible testing scenarios, the rules/logic may be briefly summarized as: if the patient has at least one prior positive test result, indicating the patient is positive for the disease until: a) a second threshold amount of time has elapsed since a first negative test result following the prior positive test result; or b) two negative test results are received following the prior positive test result, the two negative tests carried out with at least a third threshold amount of time between the tests. The thresholds described herein may be based on CDC guidelines and/or may be set by a user, and may be updated as guidelines change due to evolving understanding of the coronavirus and COVID.

At 1110, once a patient disease status for COVID is determined, a patient disease load and a patient disease activity may be determined at a system level and at a facility level. The patient disease load may include the total number of patients at the facility (or system-wide) that are positive, the number of patients that are currently under investigation, and the number of patients that are negative. The patient disease activity may include the number of patients that have tested positive each day, a change in positive patients over a specified duration, a number of patients that have recovered (e.g., previously tested positive and now considered negative), a projected number of positive patients and/or a projected number of tests that will be performed in the future, and so forth. In some examples, the number of patients that are positive may be cumulative, so that patients who have recovered are still included. In other examples, the number of patients that are positive may include only those patients considered to have active COVID positive status. Likewise, the number of patients that are negative may only include patients who are negative and have never tested positive. In other examples, the number of patients that are negative may include patients that were previously positive but are now considered to be negative.

At 1112, the COVID status, including patient load and patient activity is provided to the infectious disease module and the national capacity module, which may use the status, patient load, and/or patient activity to populate dashboards that will be visualized as one or more of the GUIs described herein. Method 1100 then returns.

FIG. 11B shows an example table 1120 illustrating a set of rules/logic that may be applied to determine the COVID status for a patient that has tested positive at least one time for COVID. The table 1120 includes a first set of columns 1122 where n−2 test results may be mapped, a second set of columns 1124 where prior test results may be mapped, a third set of columns 1126 where the current test results may be mapped, and a fourth column 1128 showing the disease status designated for the test results shown in the corresponding row. For the first set of columns 1122, a first column is for results for a test performed more than a second threshold amount of time (herein, Y so that the column is named >Y ago) and a second column is for results for a test performed less than the second threshold amount of time (<Y ago). For the second set of columns 1124, a first column is for results for a test performed more than the second threshold amount of time (>Y ago), a second column is for results for a test performed less than the second threshold amount of time (<Y ago), and a third column is for determining if a third threshold amount of time (Z) has elapsed between when the prior test was conducted and when the current test was conducted. For the third set of columns 1126, a first column is for results for a test performed more than the second threshold amount of time (>Y ago) and a second column is for results for a test performed less than the second threshold amount of time (<Y ago).

The thresholds (Y and Z) may be configured by a user and/or may be based on current CDC guidelines. As shown in FIG. 11B, the second threshold (Y) may be 5 days and the third threshold (Z) may be 24 hours. The second threshold may further include the patient being asymptomatic during the indicated amount of time.

The table 1120 may be stored in memory of the resource utilization server 202 and may be applied to determine the current COVID status of a patient who has had at least one positive test. As appreciated by table 1120, if the patient tests positive for COVID in the current test, the patient is considered positive regardless of past test results. However, if the patient tests negative in the current test or if the current test results are inconclusive, the prior test result and/or n−2 test result may be analyzed to determine current patient status. The designations in the fourth column 1128 may include positive (CV19+), under investigation (PUI-NEG*), and negative (dropped from tile). The dropped from tile designation may indicate that the patient is no longer being tracked on a hospital or larger system-wide COVID patient tracker, but that patient may still be counted in a cumulative disease-positive count.

As an example, a patient that tested positive in an n−2 prior test, negative in a prior test, and negative in the current test would be considered under investigation if the prior test was performed less than five days ago and the two negative tests were carried out less than 24 hours apart. However, if the prior test was carried out more than five days ago, the patient would be considered negative regardless of the timing between the two negative tests. In short, a patient would need a negative test followed by 5 asymptomatic days without testing positive again to be considered negative, or two negative tests in a row with at least 24 hours between the two tests to be considered negative.

FIG. 11C shows an example table 1140 illustrating a set of rules/logic that may be applied to determine the COVID status for a patient that has not tested positive at least one time for COVID. The table 1140 includes a first set of columns 1142 where n−2 test results may be mapped, a second set of columns 1144 where prior test results may be mapped, a third set of columns 1146 where the current test results may be mapped, and a fourth column 1148 showing the disease status designated for the test results shown in the corresponding row. For the first set of columns 1142, a first column is for results for a test performed more than a first threshold amount of time (herein, X so that the column is named >X ago) and a second column is for results for a test performed less than the first threshold amount of time (<X ago). For the second set of columns 1144, a first column is for results for a test performed more than the first threshold amount of time (>X ago) and a second column is for results for a test performed less than the first threshold amount of time (<X ago). For the third set of columns 1146, a first column is for results for a test performed more than the first threshold amount of time (>X ago) and a second column is for results for a test performed less than the first threshold amount of time (<X ago).

The threshold (X) may be configured by a user and/or may be based on current CDC guidelines. As shown in FIG. 11C, the first threshold (X) may be 14 days, which may be based on a longest possible (known) incubation period for the coronavirus.

The table 1140 may be stored in memory of the resource utilization server 202 and may be applied to determine the current COVID status of a patient who has not had a positive test. As appreciated by table 1140, a negative test result is not an automatic indicator that the patient is negative for COVID, as the coronavirus may be at a low viral load and undetectable by the test. Thus, a patient is only considered negative if the patient has had a negative or inconclusive test that was performed at least the first threshold amount of time ago. Otherwise, the patient is considered under investigation (though presumptively negative, as indicated by the PUI-NEG status).

Figure 12:
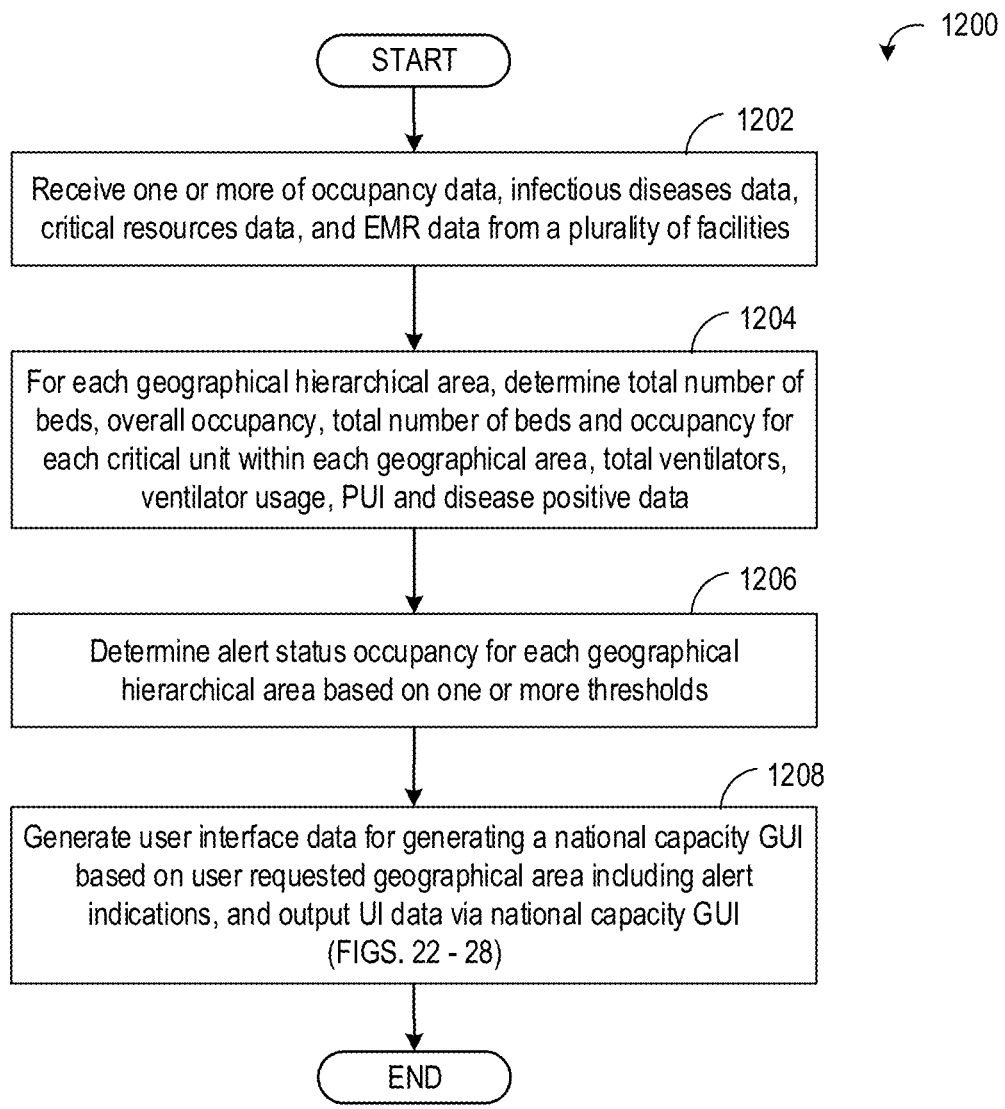
FIG. 12 is a flowchart illustrating an example method for generating user interface data for a national capacity GUI.

Next, FIG. 12 shows a flowchart illustrating a high-level method 1200 for generating user interface data for a national capacity graphical user interface (GUI) showing hospital occupancy and critical resource capacities across a network of hospitals at various geographical hierarchical levels, including a national, regional, state, and hospital system (within the state) level. The national capacity GUI is described with respect to FIGS. 22-28 and 37-44. Method 1200 may be carried out according to instructions stored in memory of a computing device in communication with the one or more hospitals or medical facilities, such as national capacity module 208 of resource utilization server 202, the resource utilization server 202, an edge device connected to the resource utilization server, or any appropriate combination thereof.

At 1202, method 1200 includes receiving a plurality of data feeds from each of a plurality of facilities across various geographical hierarchical areas (e.g., national, regional, and state). The facilities are healthcare facilities that can provide in-patient care and have critical care capabilities or can be modified to include critical care capabilities, such as hospitals. Example facilities are shown and described at FIGS. 1-5. In the present disclosure, the terms facilities and hospitals are used interchangeably. The plurality of data feeds may include one or more of HL7 data feeds and flat file data feeds, as discussed with respect to FIGS. 2-5 and FIGS. 6A, 6B, 7A, 7B, and 8. The plurality of data feeds may include one or more of occupancy data, infectious diseases data, critical resources data, and EMR data. Details of generating the plurality of data feeds are described at FIGS. 6A, 6B, 7A, 7B, and 8.

At 1204, the method 1200 includes determining each geographical hierarchical area, total number of beds, overall occupancy, total number of beds and occupancy for each critical unit within each geographical area, total ventilators, ventilator usage, PUI and disease positive data. In particular, the received data feeds may be processed to generate user interface data for populating and updating the national capacity user interface in real-time or near real-time.

Next, at 1206, the method 1200 includes determining alert status for bed occupancy and critical resource usage (e.g., ventilator usage) for each geographical hierarchical area based on one or more thresholds. An example alert structure based on various thresholds for occupancy and ventilator usage is shown below at Table 1.

TABLE 1

| Alert | Condition 1 | Condition 2 | Condition 3 |
|---|---|---|---|
| Red | ICU OCC > 92 | Total OCC >94 | Vent Utilization =>86 |
| Amber | ICU OCC =>85 and 92<= | Total OCC =>88-94<= | Vent utilization =>75 |
| No Alert | ICU OCC = 70-84 | Total OCC =>78-87<= | Vent utilization =>65 and <75 |
| Green | ICU OCC <70 | Total OCC <78 | Vent Utilization <65 |

Table 1 above shows first set of thresholds and threshold ranges for providing red, amber, no alert, or green alert with respect to ICU occupancy under condition 1; second set of thresholds and threshold ranges for providing red, amber, no alert, or green alert total occupancy under condition 2; and a third set of thresholds and threshold ranges for providing red, amber, no alert, or green alert with respect to ventilation usage. It will be appreciated that the threshold may be configurable by an administrative user, and applied to all users. Further, the threshold ranges may vary based on the type of unit and the type of public health situation.

Next, at 1208, the method 1200 includes aggregating user interface data for updating and populating a national capacity graphical user interface. The national capacity graphical user interface may be an aggregated tile showing total bed occupancy, critical care unit occupancy for adults and pediatric patients (e.g., ICU, IMC, ACUTE, OBS), critical resource usage (e.g., overall ventilator usage), and infectious disease status for various geographical hierarchical areas selectable by the user. The aggregated national capacity tile (that is, the national capacity GUI) may be displayed at a display unit of a client device, such as a workstation at a hospital command center. Additionally, when selected, one or more alert statuses may be displayed. The alert status may enable a user to see, at a glance, hospitals that are under the most stress (red) and hospitals with the most available capacity to help (green). While alert views may be adjusted by individual users at the workstation based on the desired display configuration, the thresholds for indicating various alerts described above may be changed only by authorized users.

Upon generating the user interface data, the method 1200 includes outputting the generated UI data via the national capacity GUI. In one example, the computing device may transmit user interface data that may then be used by a template stored at a workstation interface to populate the various tiles, sub-tiles, and fields within the aggregated tile of the national capacity GUI. In another example, the aggregated tile may be generated at the resource utilization server with the populated updated real-time data (or near real-time data) and transmitted to the requesting workstation for display. In some examples, an appropriate combination of the above approaches for populating and displaying the GUI may be used.

Figure 13:
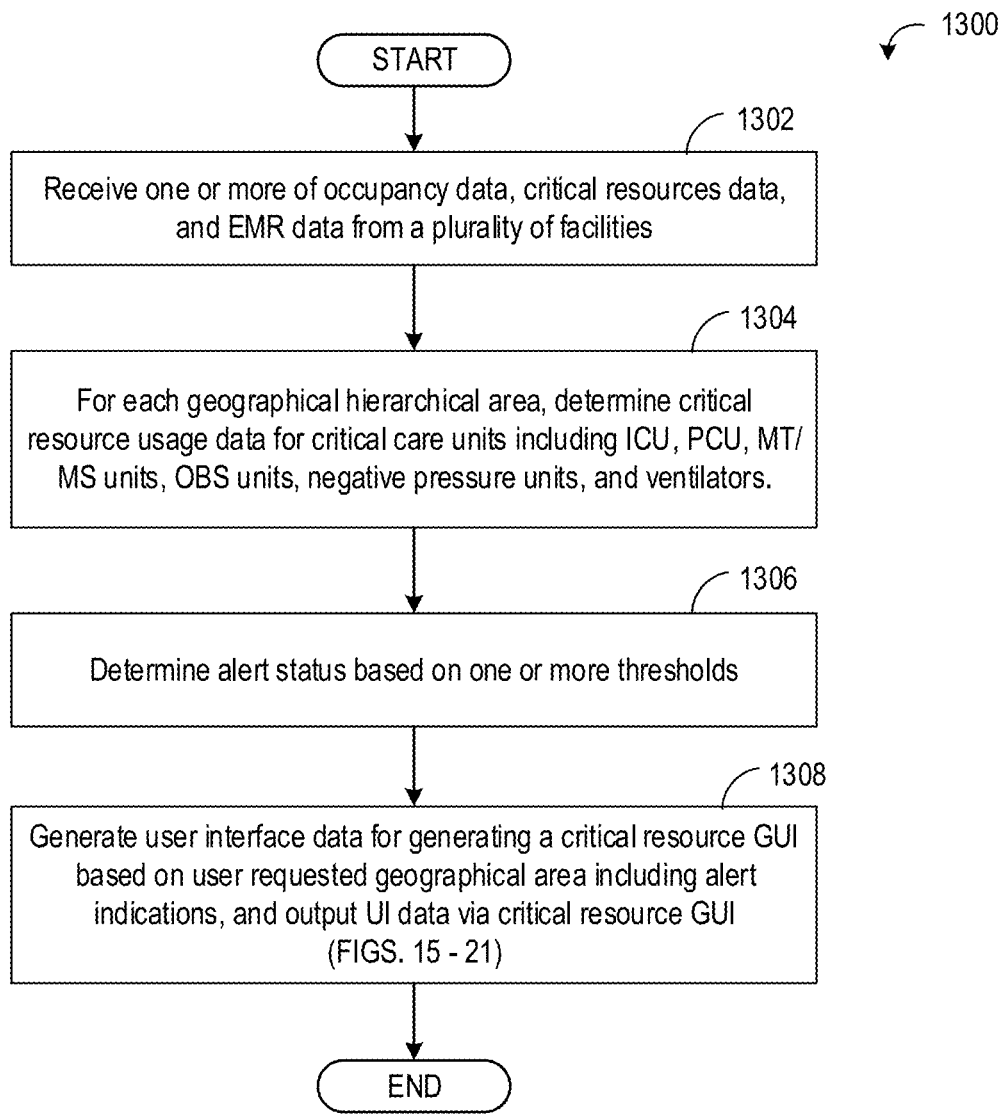
FIG. 13 is a flowchart illustrating an example method for generating user interface data for a critical resource GUI.

Turning next to FIG. 13, it shows a flowchart illustrating a high-level method 1300 for generating user interface data for a critical resources graphical user interface (GUI) showing critical resource utilization across a network of hospitals at various geographical hierarchical levels, including a national, regional, state, and hospital system (within the state) level. The critical resources GUI is described with respect to FIGS. 15-21. Method 1300 may be carried out according to instructions stored in memory of a computing device in communication with the one or more hospitals or medical facilities, such as critical resources module 206 of resource utilization server 202, the resource utilization server 202, an edge device connected to the resource utilization server, or any appropriate combination thereof.

At 1302, method 1300 includes receiving a plurality of data feeds, including occupancy data, critical resources data, and EMR data from each of a plurality of facilities across various geographical hierarchical areas (e.g., national, regional, and state). Step 1302 is similar to 1202.

Next, at 1304, the method 1300 includes for each geographical hierarchical area, determining critical resource usage data for critical care units including ICU, PCU, MT/MS units, OBS units, negative pressure units, and ventilators.

Next, at 1306, the method 1300 includes determining alert status for the various critical care unit occupancy and critical resource usage (e.g., ventilator usage) for each geographical hierarchical area based on one or more thresholds. Example thresholds for total bed occupancy, ICU occupancy, and ventilator usage are shown and discussed with respect to table 1.

Next, at 1308, the method 1300 includes generating user interface data for generating a critical resource GUI based on user requested geographical area including alert indications. For example, generating user interface data includes aggregating user interface data for updating and populating a critical resource graphical user interface. The critical resource graphical user interface may be a critical resource aggregated tile showing critical care unit occupancy (e.g., ICU, PCU, MT/MS, OBS, negative pressure units), critical resource usage (e.g., overall ventilator usage), and infectious disease status for various geographical hierarchical areas selectable by the user. Example critical resource GUI is shown with respect to FIGS. 15-21. Upon generating the user interface data, the method 1300 includes outputting the generated UI data via the critical resource GUI. Outputting the generated UI data may be performed as discussed above with respect to FIG. 12.

Figure 14:
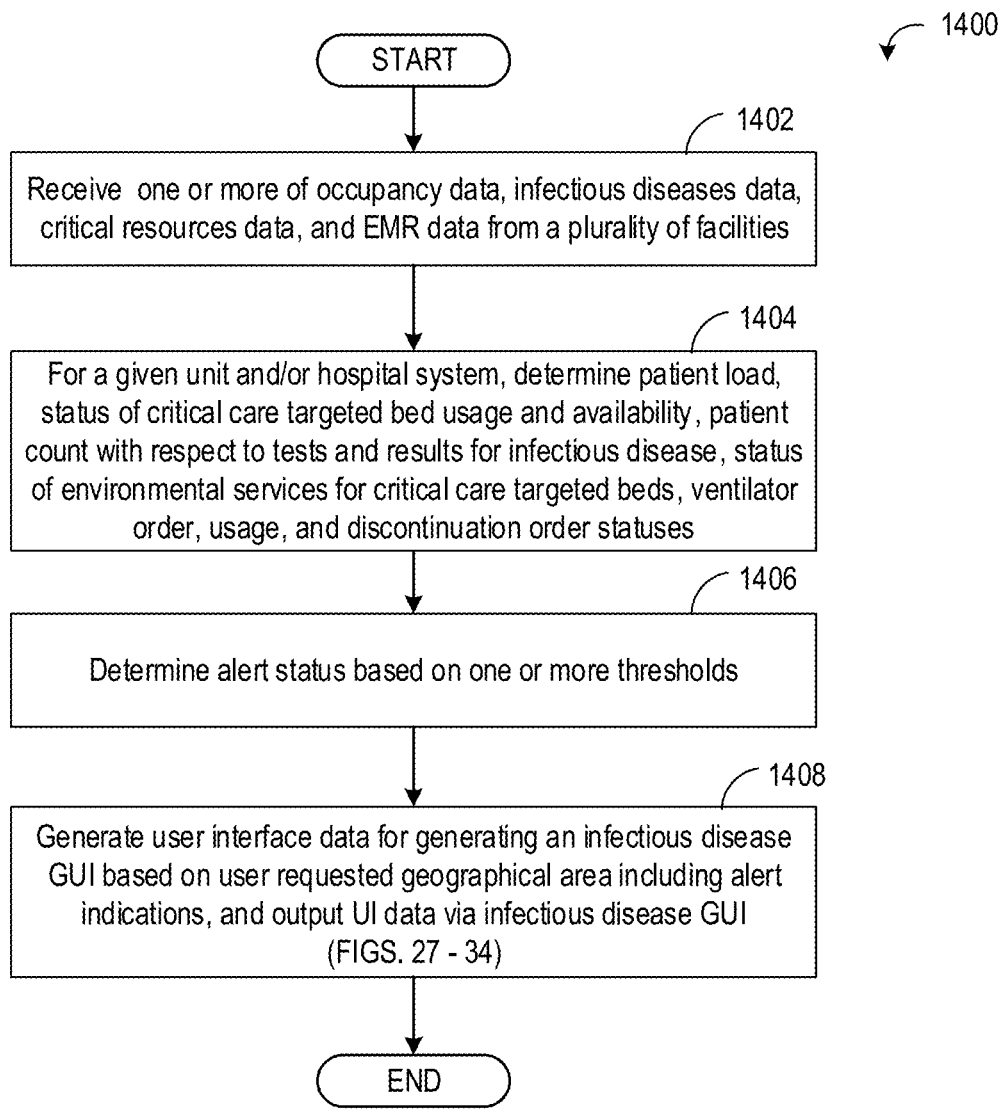
FIG. 14 is a flowchart illustrating an example method for generating user interface data for an infectious disease GUI.

Next, FIG. 14 shows a flowchart illustrating a high-level method 1400 for generating user interface data for an infectious disease graphical user interface (GUI) showing occupancy rates of resources within a single hospital or a system of hospitals and infectious disease data. The infectious disease GUI is described with respected to FIGS. 29-34. Method 1400 may be carried out according to instructions stored in memory of a computing device in communication with the one or more hospitals or medical facilities, such as infectious disease module 204 of resource utilization server 202, the resource utilization server 202, an edge device connected to the resource utilization server, or any appropriate combination thereof. In some embodiments, method 1400 may be executed by a computing device in a hospital data network, such as hospital data center processing units. For example, one or more processing units in a hospital data center may be configured to include a cluster of virtual machines that may receive plurality of data feeds from the hospital datacenter and/or workstations, process the received data feeds, generate user interface data for the infectious disease graphical user interface, and output the data via the user interface.

At 1402, method 1400 includes receiving a plurality of data feeds, including one or more of occupancy data, critical resources data, and EMR data from each of a plurality of facilities across a hospital system including one or more facilities. Step 1402 is similar to steps 1202 and 1302 discussed above.

Next, at 1404, the method 1400 includes for a given unit and/or hospital system, determining patient load, status of critical care targeted bed usage and availability, patient count with respect to tests and results for infectious disease, status of environmental services for critical care targeted beds, ventilator order, usage, and discontinuation order statuses.

Next, at 1406, the method 1400 includes determining alert status for the various critical care unit occupancy and critical resource usage (e.g., ventilator usage) for each unit within a facility and/or hospital system based on one or more thresholds. Example thresholds for total bed occupancy, ICU occupancy, and ventilator usage are shown and discussed with respect to table 1.

Next, at 1408, the method 1400 includes generating user interface data for generating an infectious disease GUI based on user requested facility and/or hospital system. For example, generating user interface data includes aggregating user interface data for updating and populating an infectious disease graphical user interface. The infectious disease graphical user interface may be an infectious disease aggregated tile showing critical care unit occupancy (e.g., ICU, PCU, MT/MS, OBS, negative pressure units), critical resource usage (e.g., overall ventilator usage), and infectious disease status for the facility and/or hospital system selectable by the user. Example infectious disease GUI is shown and described below with respect to FIGS. 29-34.

Moving on, FIGS. 15-44 show various GUIs that may be displayed on a display device such as a display of client device 130 in order to interact with a resource utilization system such as resource utilization server system 102 of FIG. 1, resource utilization server 202, or the like. GUIs 1500, 2200, and/or 2900 may be displayed in response to a user request to display the GUI. For example, a user may launch one or more GUIs by selecting suitable application icons displayed on the display. When the GUIs 1500, 2200, and/or 2900 launch, the user may be authenticated via a suitable authentication method, such as via a password, facial recognition, fingerprint recognition, etc.

GUIs 1500, 2200, and/or 2900 may be used to display how critical resources such as beds, ventilators, and so forth are distributed throughout a network of hospitals, including an indication of which hospitals may be in short supply of critical resources and which hospitals may have available resources. Thus, an operator such as a healthcare administrator or health authority may use GUIs 1500, 2200, and/or 2900 to view critical resources within a hospital network in order to allocate resources in an optimal manner to achieve the best possible patient outcomes across a healthcare delivery system. GUIs 1500, 2200, and/or 2900 may be used to display one or more dashboards with hospital-specific information, such as dashboard 104 of collaborative resource utilization system 100, or may be used to display one or more dashboards with data aggregated over hospitals within a given city, county, state, region, country, etc.

Figure 15:
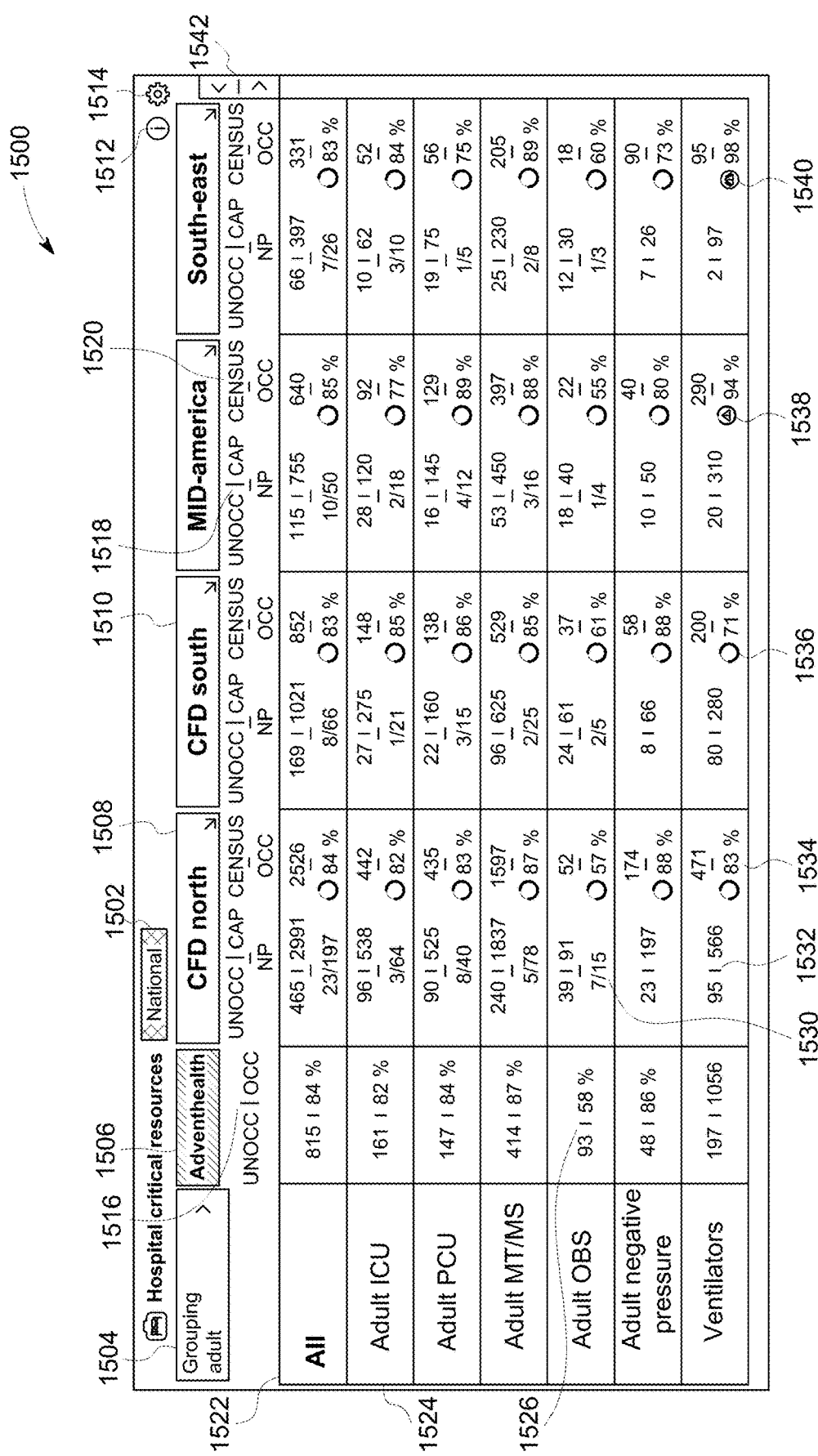
FIG. 15 shows an example GUI that displays resource availability within a hospital network at a national level.
Figure 16:
FIG. 16 shows an example view of the GUI of FIG. 15 for filtering hospital resources by type.

FIG. 15 shows an example GUI 1500 that displays hospital critical resource data at various geographical scopes and broken down by resource type. GUI 1500 may include a control element such as drop-down menu 1504 to filter the data displayed in GUI 1500 by resource or by resource group, e.g. beds, ventilators, critical resources, etc., as shown in FIG. 16. Additionally, GUI 1500 may include display elements such as information icon 1512 and settings icon 1514, which when selected may trigger display of display panels with additional information or selectable options for further filtering the display. In some embodiments, selecting information icon 1512 or settings icon 1514 may trigger a display panel that slides in from one side, partially obscuring GUI 1500. Selecting information icon 1512 or settings icon 1514 may also trigger a display panel that pops up as a separate window, or any other type of display panel.

GUI 1500 may be configured to initially display certain types of hospital resources at a certain scope. For example, GUI 1500 may show critical hospital resources across a network of hospitals at a national level, as indicated by scope indicator 1502. As shown in GUI 1500, an initial national view may display aggregated data from different regions of the country, such as CFD North, CFD South, mid-America, Southeast, etc. The different regions from which data has been aggregated may be displayed across the top of GUI 1500 as a series of tabs such as region tab 1508, each of which may be selected in order to view resource data for the corresponding region. An indication that the tabs may be selectable may be displayed on each tab, such as down arrow 1510, where selecting the tab may trigger the display of data at the level of scope indicated by the tab. For example, selecting tab 1508 (e.g., CFD North) may display a new dashboard showing data specific to the region CFD North, as shown in FIG. 4.

A dashboard reference tile 1506 may also be included, which indicates the scope of the information currently displayed within GUI 1500. For example, dashboard reference tile 1506 may indicate that the data displayed within GUI 1500 pertains to an entire hospital system (e.g., Adventhealth), or it may indicate that the data displayed within GUI 1500 pertains to hospitals of the hospital system located in a specific region, such as CFD North. Dashboard reference tile 1506 may be of a different color, or may employ bold text, or a similar distinguishing feature in order to make it stand out. GUI 1500 may also include control elements such as right and left arrows 1542 that allow a user to scroll horizontally through other regions that may not be displayed in GUI 1500 due to display width limitations.

GUI 1500 may display hospital resource information as a series of tiles arranged in columns and rows within a tiled layout, where rows may indicate the type of resource or resource group to be displayed (based on the selection offered by the drop-down menu 1504) and columns may indicate categories of data, such as national, regional, etc. Further, each column may be broken into sub-columns that display different types of data, for example, a resource occupancy rate, capacity, number of units in use or available, etc. GUI 1500 may display column headers such as column header 1516, column header 1518, and column header 1520 to indicate the types of data displayed in the tiles within that column. In the illustrated example, column header 1516 shows two category headers: one for the number of unoccupied (e.g., available) resource units ("UNOCC"), and one for the corresponding occupation rate ("OCC"). For example, tile 1526 indicates that there are 93 unoccupied beds in adult observation units across the entire hospital network, for an occupancy rate of 58%. Column header 1518 shows three sub-headers: one for the number of unoccupied resources ("UNOCC"), one for the capacity of the resource in question ("CAP"), and one for the number of resources located in negative pressure units ("NP"), in this case displayed as a ratio of occupied beds to total beds. Column header 1520 shows two category headers: one for total resource count (CENSUS) and one for the occupation rate ("OCC").

In an embodiment, the occupation rate may be expressed as a percentage, as shown in occupation rate 1534, or via an icon, such as occupation icons 1536, 1538, or 1540. In the illustrated example, occupation icons 1536, 1538, 1540 graphically represent a percentage via a heavy line superimposed upon a circle, where the perimeter of the circle represents 100% and the heavy line indicates a portion of the total perimeter. Additionally, color may be used to indicate degree of availability or use. For example, occupation icon 1536 is green, indicating that ventilator utilization is below a first threshold (e.g., low occupancy); occupation icon 1538 is amber, indicating that ventilator utilization is above a first threshold but below a second threshold (e.g., medium occupancy); and occupation icon 1540 is red, indicating that ventilator utilization is above a second threshold (e.g., high occupancy). In the examples shown herein, the first threshold may be 89% and the second threshold may be 94%, such that an occupation icon may change from green, for example, to amber when the corresponding occupancy rate changes to a value in the range of 90-94% and the occupation icon may change to red when the corresponding occupancy rate changes to a value in the range of 95-100%.

For example, in FIG. 15 the user has selected a grouping "Adult" in drop-down menu 1504, indicating that the user wishes to view and compare the allocation of certain groups of resources across adult care facilities/units nationally, broken down in columns representing different regions. In an embodiment, resources and resource groups selected by the user are displayed in the first column as row headers. Row header 1522 (e.g., "All") indicates that the first row displays the number of resource units (e.g., beds) available across all resource subgroups. Row header 1524 (e.g., "Adult ICU") corresponds to the subgroup "ICU", indicating that the second row contains data on adult ICU bed occupancy. GUI 1500 may display a plurality of subgroups as additional rows, each row representing a resource such as beds in a given area (e.g., Progressive Care Unit (PCU), Observation Unit (OBS), negative pressure units, etc.), ventilators, etc. It should be appreciated that the resources or units described herein are for illustrative purposes and should not be construed as limiting.

Moving across the top of GUI 1500, the first data column (e.g., second column) displays the number of unoccupied resources and the occupancy rate for the entire hospital system (Adventhealth), while the second, third, fourth, and fifth data columns show summary data for the regions CFD North, CFD South, Mid-America, and Southeast, respectively. The summary data displayed in each tile may include the number of unoccupied resources, capacities, number of patients, total number of individuals being treated, and occupancy rate. As an example, tile 1526 shows the number of unoccupied resources (e.g., beds) in Adult OBS units across the entire national Adventhealth hospital network (in this case, 93), and the corresponding occupancy rate expressed as a percentage (in this case, 58%). Alternatively, tile 1530 in the column immediately to the right indicates that in the region CFD North there are 39 unoccupied beds, out of a total capacity of 91 beds; 7 unoccupied beds located in negative pressure rooms, out of a total of 15 beds; a total number of 52 beds are being used (total capacity of 91 minus 39 unoccupied); at a total occupancy rate of 57%, which is below a first threshold (e.g., 70%), indicating high availability. It should be appreciated that for some resources, some of the column headers may not be applicable. For example, tile 1532 indicates that in the region CFD North there are 95 unused ventilators out of a total of 566. However, ventilators are a mobile resource that can be moved to different locations, and thus no ratio is displayed for negative pressure rooms.

Moving on, FIGS. 16-21 illustrate how control elements within GUI 1500 can be used to filter or narrow the scope of the data being shown, for example by showing data for a single resource such as beds, ventilators, etc., or a single region within the country, single hospital within a region, single unit within a hospital, etc. FIG. 16 shows example view 1600 of GUI 1500, where a user has selected the drop-down menu 1504 in order to change the selection of data being displayed from its current grouping "Adult", e.g. resources used in adult units, to a different resource group. For example, a user may select the drop-down menu item 1602 indicating "All" in order to display all resource types (not just adult units). As shown in example view 1600, drop-down menu 1504 may include other hospital resources or groups of resources such as critical resources, pediatric resources (peds), resources from a given specialty, etc. For example, if a user selected "Critical Resources" in drop-down menu 1504, the left column of GUI 1500 would be populated with a list of hospital resources identified as critical. The resources identified as critical may be established in advance based on a specific resource allocation need, for example, in the case of Covid19, ventilators might be considered a critical resource. Similarly, resources not considered critical would not be displayed. In some examples, resources may be deemed critical automatically based on average occupancy rates, rate of increase of occupancy, etc., which may indicate a particular resource is in demand and thus may be considered critical.

FIG. 17 shows regional view 1700 of GUI 1500, where a user has limited the resources being displayed in GUI 1500 to the region CFD North by selecting region tab 1508 "CFD North" shown in FIG. 15. In regional view 1700, the current scope of GUI 1500 is updated in scope indicator 1502, indicating that data is being displayed at a regional rather the national level. Similarly, dashboard reference tile 1506 now indicates that data from hospitals of the hospital network located in the region CFD North is being shown, and the region tab CFD North has been replaced by hospital tab 1702 (e.g., Deland Hospital). The rest of the regional tabs for CFD South, Mid-America, and Southeast have been replaced with tabs indicating the hospitals located in the selected region CFD North. As described in FIG. 15, right and left arrows 1542 may be used to scroll right or left horizontally in order to navigate between different hospitals located in the target region of CFD North. GUI 1500 may include a control element such as back arrow 1704, which allows a user to navigate back up to a national level and widen the scope of the data being displayed.

As shown above in FIG. 15, a control element such as down arrow 1510 may be displayed on the hospital tabs at the top of GUI 1500, indicating that the scope of the data being displayed can be further limited to a hospital level. Similarly, some of the data tiles may include a down arrow 1706, to indicate that additional data may be viewed by hovering over or selecting the tile, upon which GUI 1500 may trigger an additional display panel. In an embodiment, an additional display panel may comprise a pop-up window as shown in FIG. 18.

FIG. 18 shows example regional view 1800 of GUI 1500, where a user is hovering over data point 1802, triggering a pop-up display panel 1804 with additional information relevant to data point 1802. Pop-up display panel 1804 may include a header explaining what the data point represents, for example, that data point 1802 represents the number of ventilators in use (at Waterman hospital), as well as the value of the relevant data point (e.g., 82). As shown in the illustrated example, pop-up display panel 1804 may contain information such as a list of all the patients or beds with ventilators, a serial number of each ventilator, the amount of time the ventilator has been in use, etc.

FIG. 19 shows facility view 1900 of GUI 1500, where resource utilization is displayed at a facility level as indicated by scope indicator 1502. For example, a user may have selected a tab for Lakeside Hospital in regional view 1700 of FIG. 17. Drop-down menu 1504 indicates that the facility Lakeside has been selected, and as described above, back arrow 1708 may allow a user to navigate back up to a regional level to widen the scope of the data being displayed. As in FIG. 15, facility view 1900 comprises rows of resources or resource groups such as beds in different units (e.g., intensive care, observation, pediatric, adult, etc.), with information for each resource displayed in columns such as census column 1902, occupancy rate column 1904, unoccupied resource column 1906, negative pressure resource column 1908, discharge orders column 1910, transfer orders column 1912, and blocked resource column 1914. For example, tile 1918 may indicate that there are 21 beds in negative pressure rooms in use and 2 that are unoccupied.

Each row may contain a down arrow 1916 which may be selected to further narrow the scope of information to only show resource utilization information for a given resource group. For example, down arrow 1916 may be selected to view resource availability within the adult medical trauma/medical surgery (MT/MS) unit, as shown in FIG. 21.

Figure 20:
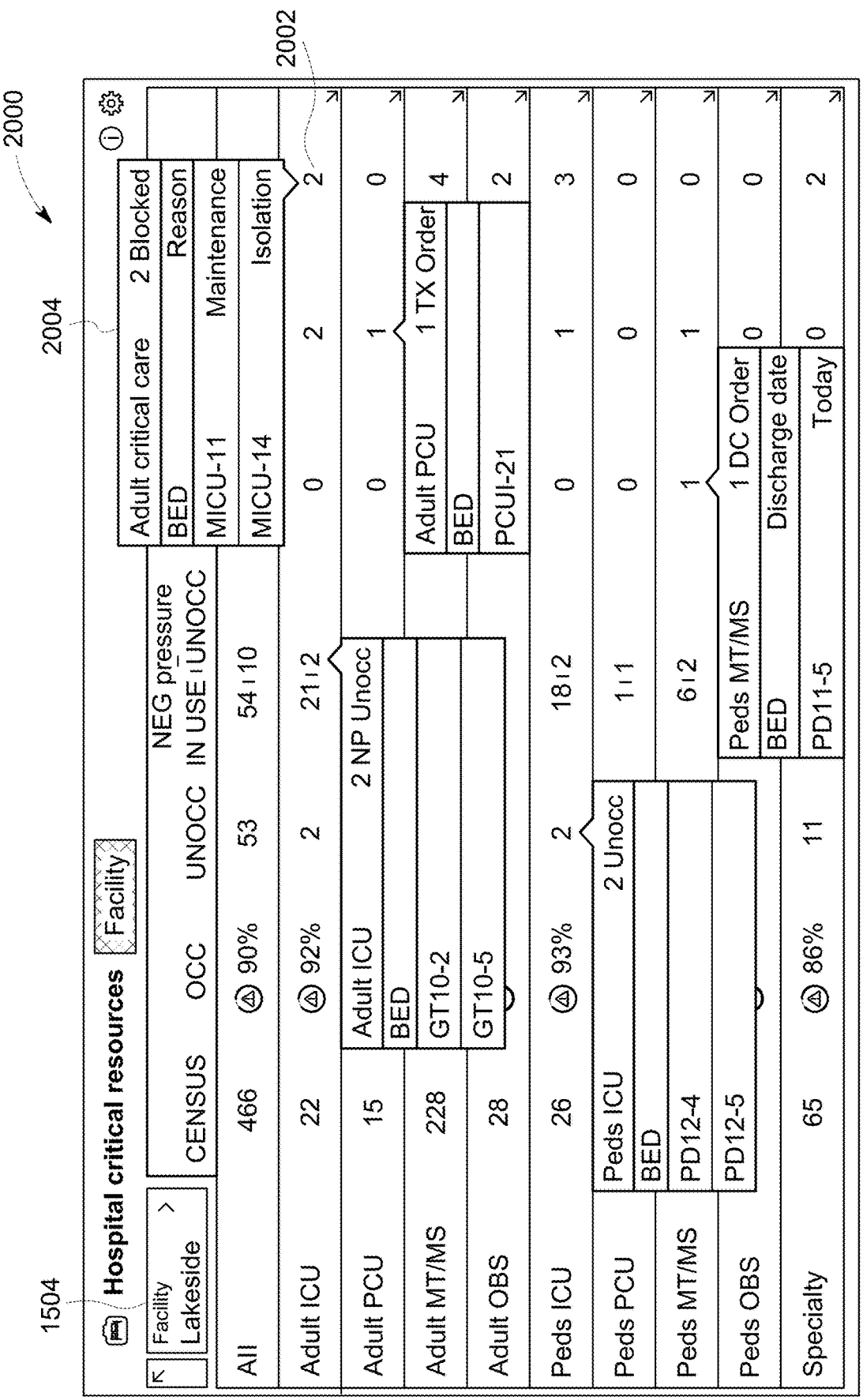
FIG. 20 shows an example view of the GUI of FIG. 15 that displays resource availability within a hospital network at a facility level, where additional data is displayed via pop-up display panels.

Moving on to FIG. 20, example facility view 2000 of GUI 1500 shows a series of pop-up display panels that may be triggered when a user hovers over or otherwise selects data points in GUI 1500. For example, for the facility Lakeside (indicated by dashboard reference tile 1506), hovering over data point 2002 may trigger pop-up display panel 2004, which displays a list of beds in adult critical care units that are blocked, as well as the reason for being blocked.

FIG. 21 shows unit view 2100 of GUI 1500, where utilization of a given resource or resource type is shown at a unit level for a hospital/medical facility (as shown by scope indicator 1502). For example, unit view 2100 may be displayed when a user selects down arrow 1916 in facility view 1900, corresponding to the row for the adult medical trauma/medical surgery unit resource.

In unit view 2100, header row 2102 displays aggregate data on resource utilization across all adult medical trauma/medical surgery units, while the rows below it show resource utilization data for individual units. For example, row 2104 shows total patient counts and patient counts for the intensive care unit (ICU) and progressive care unit (PCU), occupancy rate, number of unoccupied beds, number of beds in negative pressure rooms, both in use and unoccupied, number of discharge orders, number of transfer orders, and the number of blocked beds, all for the unit 5 North.

FIGS. 22-28 show example views of a GUI 2200 (e.g., a first embodiment of a national capacity GUI) for viewing resource utilization data across hospitals, regions, states, etc. As with GUI 1500, GUI 2200 may be used to display how critical resources such as beds, ventilators, and so forth are distributed throughout a network of hospitals, including an indication of which hospitals may be in short supply of critical resources and which hospitals may have available resources.

GUI 2200 may show hospital capacities across a network of hospitals at a national, regional, or state level, as indicated by scope indicator 2202. As shown in GUI 2200, a default or initial national view may display aggregated data from different regions of the country, such as Northeast, Midwest, South, West, etc., where the different regions are represented as rows. GUI 2200 may also include slider button 2204, which may be used to toggle between state-based data and data from metropolitan statistical areas (MSAs). Additionally, control elements such as census button 2222, unoccupied resource button 2224, and/or capacity button 2226 may be used to toggle the display of data between total bed count, available bed count, or bed capacity, respectively, for any of the regions, states, divisions, facilities, etc. displayed in GUI 2200.

The different types of resources that may be available may be displayed across the top of GUI 2200 as a series of resource tabs, such as beds tab 2208, adult units tab 2210, pediatric units tab 2212, and/or ventilator tab 2214, each of which may be selected in order to view the corresponding type of resource data. GUI 2200 may additionally include a column for resources relating to a specific disease or condition, such as COVID tab 2216. Additionally, GUI 2200 may include display elements such as information icon 2218 and settings icon 2220, which when selected may display panels with additional information or selectable options for further filtering the display. In some embodiments, selecting information icon 2218 or settings icon 2220 may trigger a display panel that slides in from one side, partially obscuring GUI 2200, as explained in greater detail below. Selecting information icon 2218 or settings icon 2220 may also trigger a display panel that pops up as a separate window, or any other type of display panel. GUI 2200 may also include a search bar 2207, where user may enter in the name of a specific region, hospital, address, etc. in order to filter the data being displayed.

A dashboard reference tile 2206 may also be included, which indicates the scope of the information currently displayed within GUI 2200. For example, dashboard reference tile 2206 may indicate that the data displayed within GUI 2200 pertains to a given country (e.g., USA). Dashboard reference tile 2206 may be of a different color, or may employ bold text, or a similar distinguishing feature in order to make it stand out.

GUI 2200 may display hospital resource information as a series of tiles arranged in columns and rows arranged in a vertical hierarchy within a tiled layout, where rows may indicate geographic areas of varying sizes such as regions, states, divisions, etc. to be displayed. For each resource tab 2208, 2210, 2212, 2214, and 2216 across the top of GUI 2200, one or more columns may indicate different categories of resources available under each tab (e.g., the resource "beds" may be divided into categories such as beds located in intensive care units (ICU), intermediate care units (IMC), acute care units, observation units, etc.) For example, in GUI 2200, row 2228 displays the total number of occupied beds and occupancy rates across the entire hospital network in data column one ("All Beds"), followed by the total number of occupied beds and occupancy rates for the adult ICU, adult IMC, adult acute care unit, and so on for the other hospital units displayed. Under the column "VENTS", tile 2236 indicates the total number of ventilators in use throughout the hospital network (57,974), and the associated usage rate (81%). Under COVID tab 2216, tile 2238 displays the total number of patients under investigation (PUI, 1,114,944) and total number of patients who have tested positive for COVID-19 (124,217).

Row 2228 includes a header tile 2240, which in the illustrated example indicates the highest level in the data hierarchy displayed in GUI 2200 (e.g., network-wide totals.) Header tile 2240 may contain down arrow 2230, indicating that row 2228 is expanded to include rows representing data at lower levels of granularity. For example, row 2232 shows the number of occupied beds in the Northeast region, as a subset of the total indicated in row 2228. Further, rows for individual divisions may be displayed below row 2232, such as division tile 2234, which shows the number of occupied beds in the division of New England, within the Northeast region. In an embodiment, down arrow 2230 may initially appear as a forward arrow indicating that row 2228 may be expanded (as shown in division tile 2234 four New England), at which point it may change to a down arrow to indicate nested information that may be collapsed by selecting the down arrow. Thus, GUI 2200 allows a user to selectively view resource availability data such as number of occupied or unoccupied beds, ventilators, etc. at various levels of scope by selectively expanding and/or collapsing rows on the dashboard.

Figure 23:
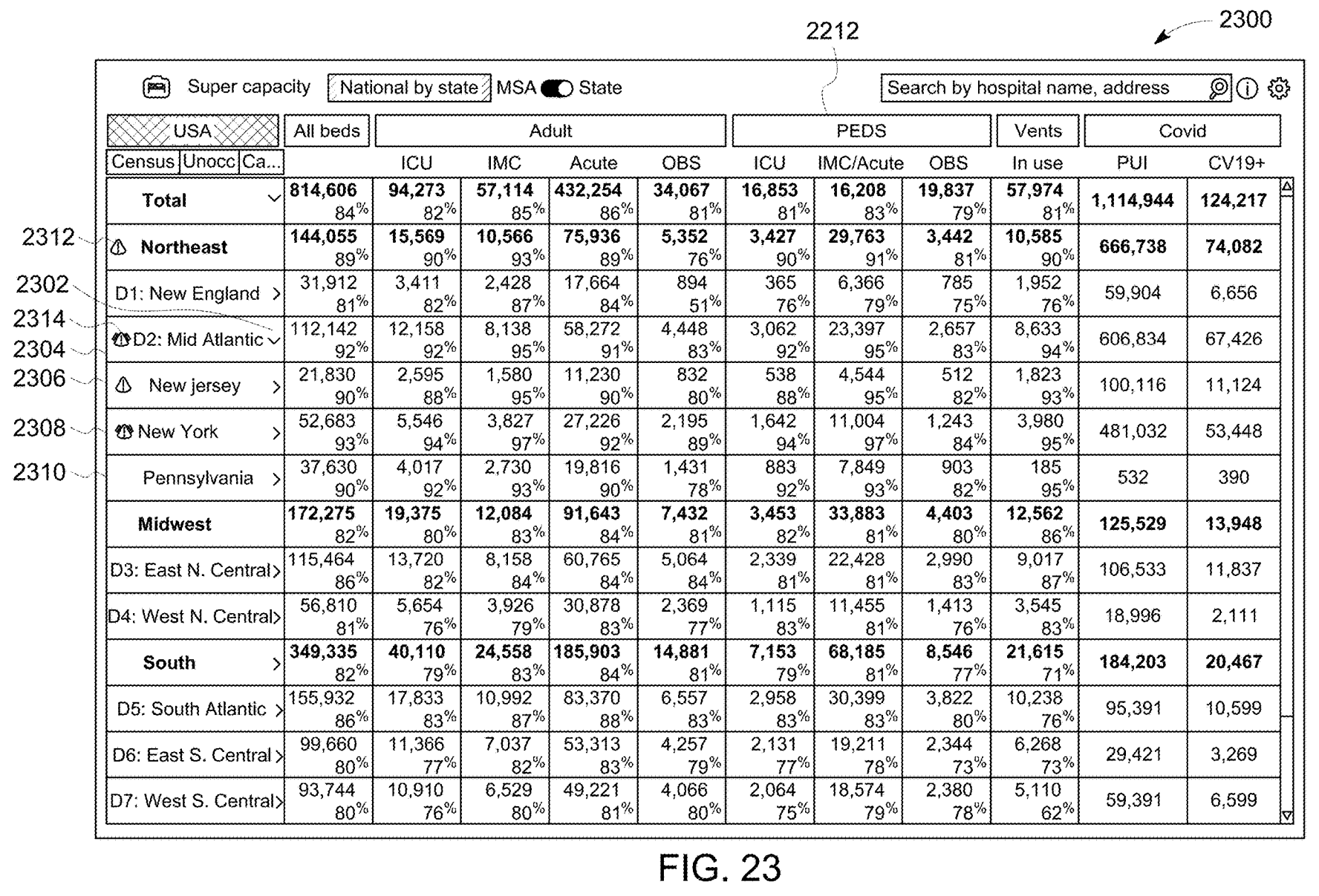
Figure 24:

Moving on, FIGS. 23, 24, and 25 show expanded views of GUI 2200, where data on available resources within the hospital network displayed in GUI 2200 are successively revealed as rows in the hierarchical display are expanded. FIG. 23 shows expanded view 2300 of GUI 2200, where row 2304 (corresponding to the Mid Atlantic division 2) has been expanded by selecting arrow 2302 (turning it from a right arrow to a down arrow) to reveal state rows 2306, 2308, and 2310 for the states of New Jersey, New York, and Pennsylvania, respectively. In an embodiment, the rows below row 2304 (e.g., Midwest, South, etc.) may be shifted down upon the expansion of row 2304 to appear below row 2310 (the state of Pennsylvania). Additionally, an alert indicator such as alert indicator 2312 may be displayed in a row, which may provide a graphical indication of the availability of resources within hospitals represented by the row.

In an embodiment, alert indicators of different colors or shapes may be used to indicate whether the occupancy or usage rate of a given resource (e.g., beds, ventilators, etc.) is below a first threshold, above a first threshold but below a second threshold, or above a second threshold. For example, amber alert indicator 2312, in the shape of a warning sign with an exclamation point, may indicate that the occupancy rate is above a first threshold of 80% but below a second threshold of 90%. Similarly, red alert indicator 2314 may indicate that the occupancy rate is above a second threshold of 90% (e.g., approaching full capacity). A green alert (not depicted in FIG. 23) may indicate an occupancy rate below a first threshold of 80%, indicating greater availability.

Similarly, FIG. 24 shows expanded view 2400 of GUI 2200, where row 2308 (corresponding to the state of New York) has been expanded by selecting arrow 2402 (turning it from a right arrow to a down arrow) to reveal rows with resource data from individual hospitals within the state of New York (e.g., NY Presbyterian, NYU Langone, Long Island Jewish, Montefiore, etc.). As described above, green alert indicator 2404 may be displayed next to the hospital Buffalo General, indicating that the occupancy rate at the hospital (74%) is below a first threshold of 80%. As shown in greater detail in FIG. 26, it should be appreciated that the thresholds may be customizable and configured by a user.

Additionally, alert indicators such as amber alert indicator 2312, red alert indicator 2314, or green alert indicator 2404 may be displayed in accordance with an algorithm or collection of one or more rules, which may be developed based on current circumstances. For example, in a situation such as a COVID-19 outbreak where beds in an intensive care unit (ICU) and ventilators are in particularly high demand, an amber or red alert indicator may be displayed next to a given hospital based on the occupancy rate of ICU beds and ventilators, while ignoring other resources such as beds in different units. FIG. 25 shows expanded view 2500 of GUI 2200, where an amber alert 2502 is displayed next to the hospital Mount Sinai in New York. In an embodiment, the amber alert may be displayed based on the ICU occupancy rate of 92% at tile 2504 and the ventilator occupancy rate of 81% at tile 2506, regardless of the occupancy rates in pediatric units, observation unit, etc.

FIGS. 26 and 27 show expanded views of GUI 2200, in which settings icon 2220 from FIG. 22 has been selected in order to display a settings panel. FIG. 26 shows expanded view 2600 in which settings panel 2602 comprises various display and control elements that allow a user to customize the dashboard displayed via GUI 2200. In an embodiment, settings panel 2602 may expand or slide out from the right side of GUI 2200, partially obscuring the dashboard displayed via GUI 2200. Settings panel 2602 may include a control element to close the panel, such as panel close element 2604 indicated with an X, the selection of which may cause the control panel to disappear and reveal the full dashboard displayed via GUI 2200. Settings panel 2602 may also include common control elements such as save button 2622, reset button 2624, cancel button 2626, and/or apply button 2628.

Settings panel 2602 may comprise various sections with different control or display elements. In an embodiment, GUI 2200 may include an informative section 2606 that displays information such as a list of all facilities and the regions, states, divisions, etc. in which the facilities are located. As discussed below, informative section 2606 may be updated to indicate the application of sorting or filtering algorithms that may be customized via settings panel 2602.

Settings panel 2602 may also include a sorting control panel 2608, which may provide control elements that permit a user to interactively define criteria for sorting or ordering the data displayed within GUI 2200. The control elements in sorting control panel 2608 may be drop-down menus, radio buttons, checkboxes, or similar interactive controls that allow a user to specify one or more sorting criteria from a selection of options. For example, a user who wishes to sort the data displayed in rows of the resource availability dashboard displayed in GUI 2200 in descending order from top to bottom by the total number of beds may select "All Bed Count" in a drop-down menu populated with options for sorting, and/or "Descending" in a drop-down menu populated with options for sort order (e.g., ascending or descending). An indication of any currently defined sorting criteria may also be displayed within sorting control panel 2608.

Settings panel 2602 may also include a filtering control panel 2610, which may provide control elements that permit a user to interactively define criteria for filtering data displayed within GUI 2200. Filtering control panel 2610 may include a filter selector 2616 for specifying filtering criteria. Filter selector 2616 may be a drop-down menu, radio button, checkbox, or similar interactive control that allows a user to specify one or more filtering criteria from a selection of options. Filtering control panel 2610 may also include a logical operator button 2612 that allows a user to specify a plurality of filter criteria that are appended via one or more logical operators (e.g., AND, OR, etc.). Similarly, filtering control panel 2610 may also include an add filter button 2620 and/or remove filter button 2614, which allow a user to add or remove filter criteria.

In cases in which a plurality of parameters may be associated with a given filtering criteria, filtering control panel 2610 may include a parameter list 2618, where user may select one or more parameter options associated with the corresponding filter criteria. For example, if a user specifies "Alert Level" as filter criteria in filter selector 2616, different types of pre-established alerts as described in FIG. 25 may be displayed as selectable parameters in parameter list 2618 (e.g., Critical, Warning, Beds Available, etc.). Thus, by selecting the parameter "Critical" in parameter list 2618, a user may create a dashboard display in GUI 2200 that displays rows corresponding to states, divisions, facilities, etc. where a critical (e.g., red) alert has been generated, indicating that occupancy or usage rates of the resource in question have exceeded a second threshold. FIG. 27 shows example view 2700 of GUI 2200 with an expanded settings panel 2602 where a user has selected "Alert Level" as filter criteria in filter selector 2616 of filtering control panel 2610. In parameter list 2618, warning parameter 2702 and no alert parameter 2704 have been deselected, indicating that the user does not wish to view any rows with amber alerts or no alerts associated with them (e.g., only rows with red critical alerts indicating high occupancy and green alerts indicating that beds are available will be displayed). Accordingly, in informative section 2606, hospitals displaying amber alerts or no alerts in GUI 2200 such as Mount Sinai, North Shore LU, and NYC Belleview have been disabled (e.g., displayed in gray), indicating that they will not be displayed in GUI 2200 once the new filter settings have been applied. FIG. 28 shows example view 2800 of GUI 2200 in which the filter settings from example view 2700 and FIG. 27 have been applied, whereupon only rows showing red alerts (corresponding to the hospitals NY Presbyterian, NYU Langone, Long Island Jewish, and Montefiore) and green alerts (corresponding to the hospitals Buffalo General, Upstate University, Saratoga, and White Plains) are displayed.

Figure 33:
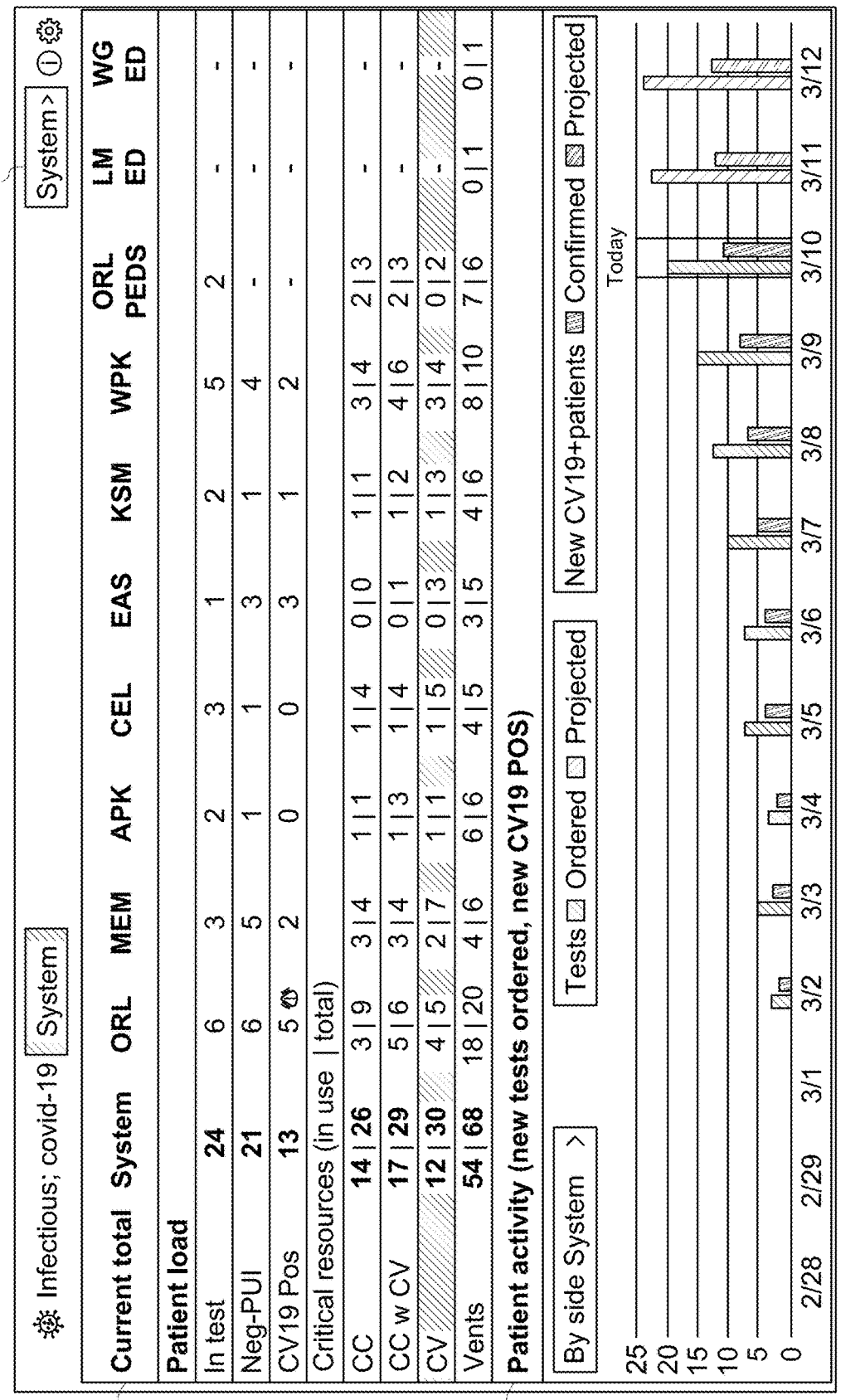
FIG. 33 shows an example view of the GUI of FIG. 29 that displays patient activity projections within a hospital system.
Figure 34:
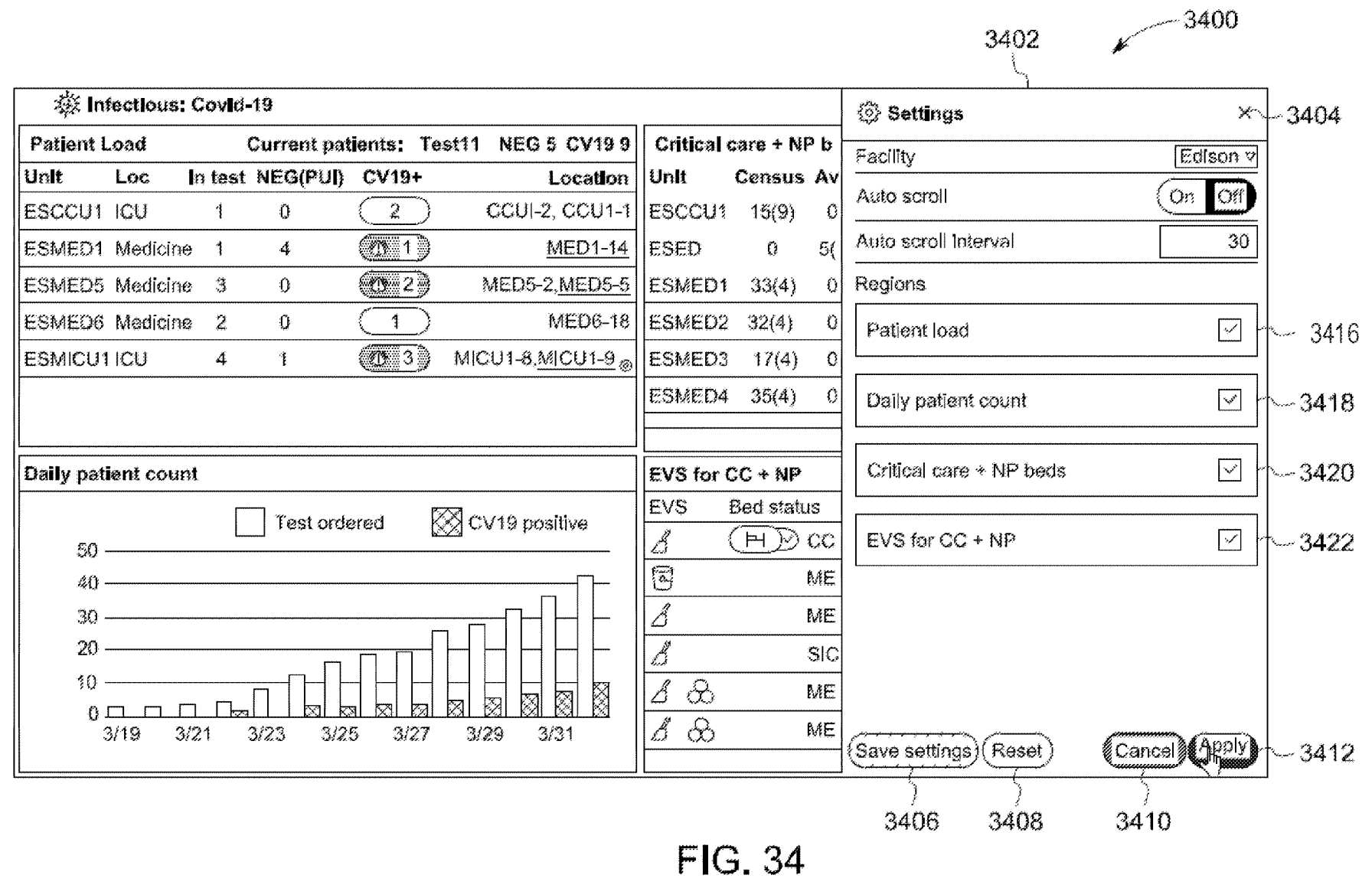
Figure 35:
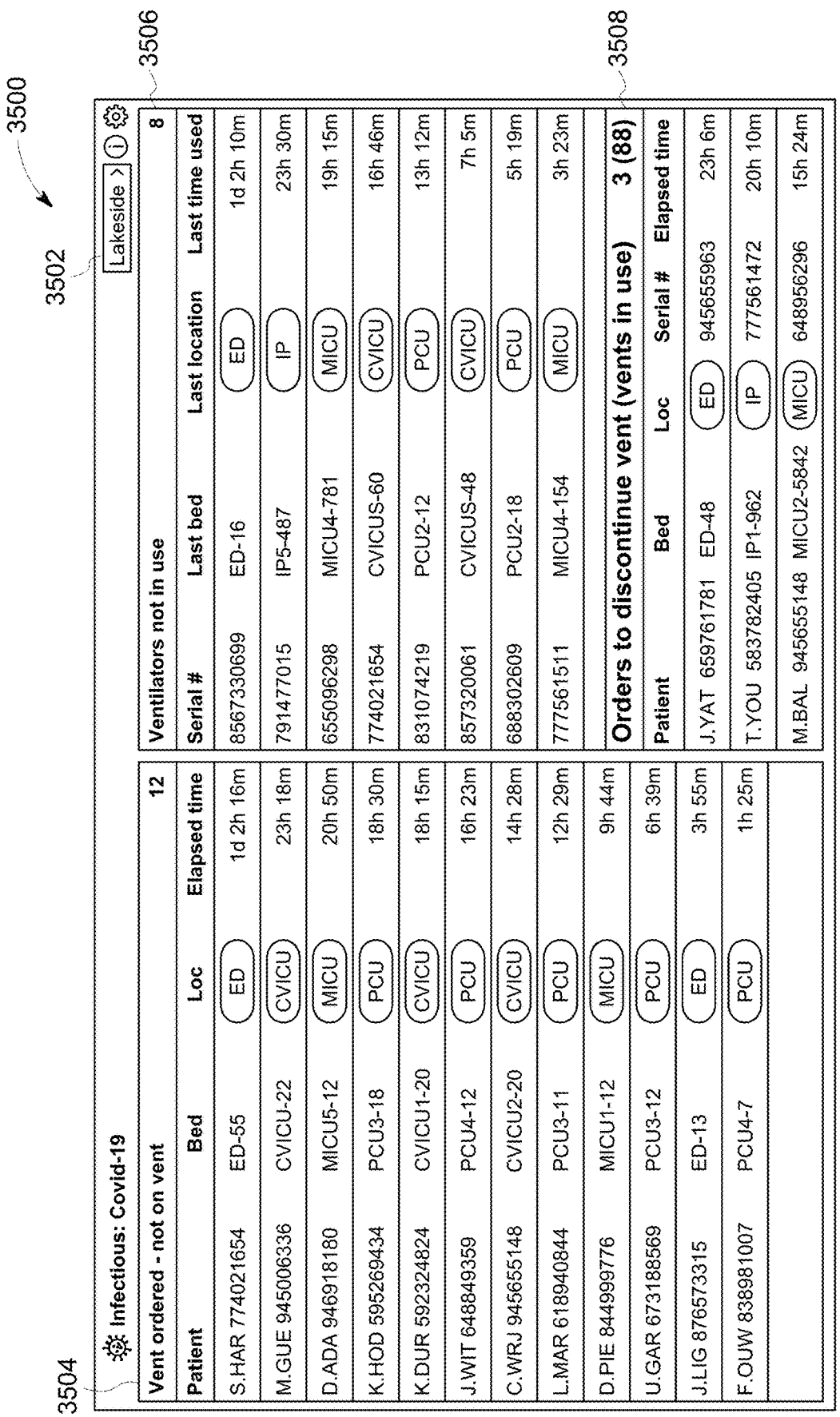

FIGS. 29-36 show example views of a third GUI 2900 (e.g., an infectious disease GUI) for viewing resource utilization data across hospitals or hospital systems. As with GUIs 1500 and 2200, GUI 2900 may be used to display how critical resources such as beds, ventilators, and so forth are distributed and utilized at a hospital and/or a network of hospitals, including an indication of which hospitals may be in short supply of critical resources and which hospitals may have available resources. While GUIs 1500 and 2200 may display resources in a table layout with columns and rows, GUI 2900 may display data via a modular layout of one or more data tiles which may be positioned adjacent to each other in various different arrangements that may be customized by a user. As an example, if one data tile is selected, it may occupy the entire space within GUI 2900; if two data tiles are selected, the two data tiles may be positioned vertically one above the other, as shown in FIG. 33; if three data tiles are selected, the three data tiles may be positioned as shown in FIG. 35; if four data tiles are selected, the four data tiles may be displayed in a quadrant view as shown in FIG. 29; and so on. In some embodiments, data tiles may have a fixed size, while in other embodiments users may be able to resize/rescale the data tiles, for example by selecting a boundary between two tiles and dragging the boundary with an input device such as a mouse. Further, some data tiles may have fixed size while other data tiles may be resizable and/or re-scalable.

FIG. 29 shows example GUI 2900, in which four data tiles are displayed in a quadrant view, each with different data regarding resource use and/or availability within a given scope. For example, GUI 2900 may show occupancy rates of resources within a single hospital or a system of hospitals, as indicated by scope indicator 2902 (e.g., Lakeside Hospital). In an embodiment, scope indicator 2902 may be a drop-down menu that allows a user to select the scope of the data to be displayed, for example, by selecting a hospital from a list of candidate hospitals.

Figure 36:
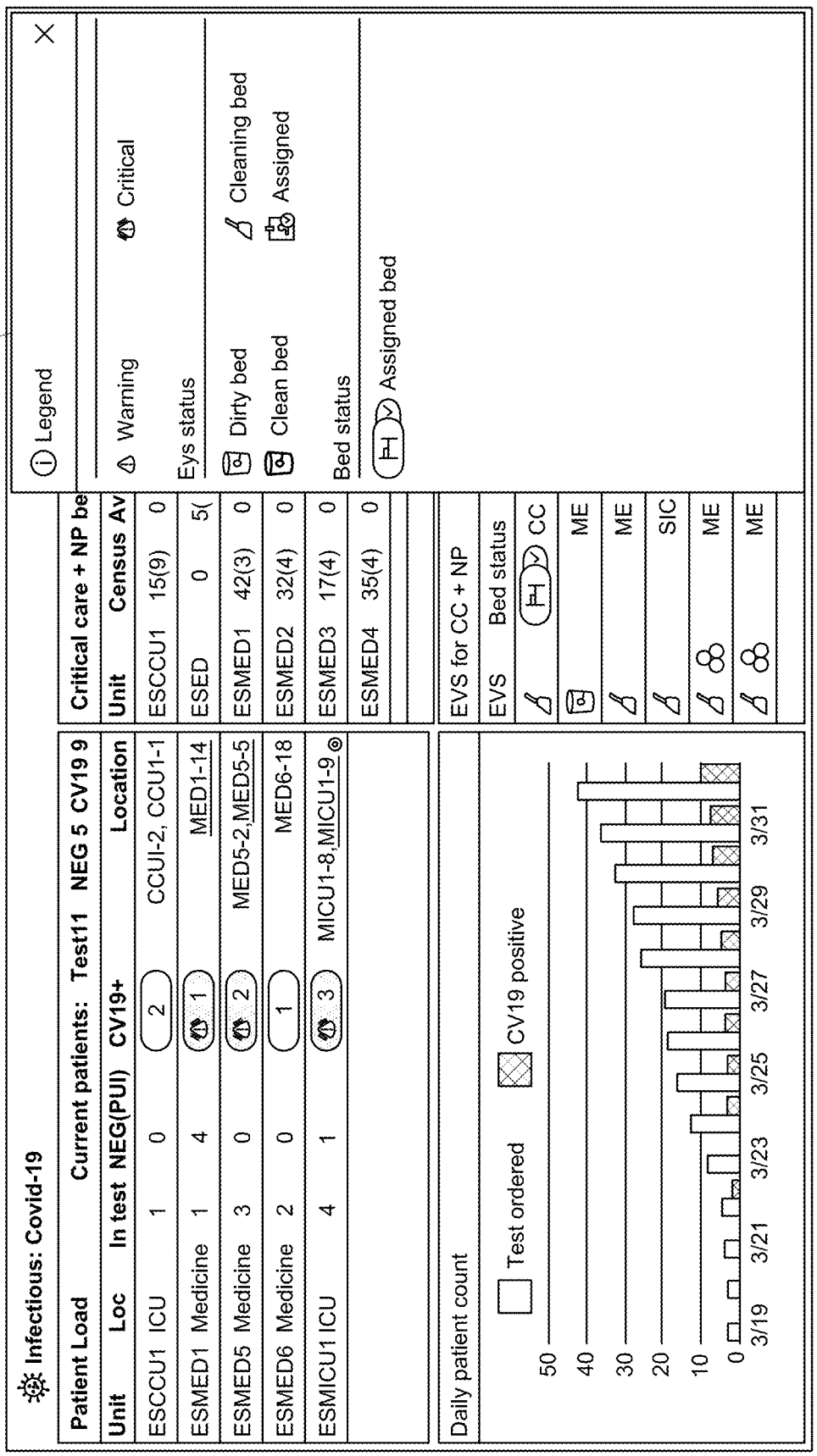
FIG. 36 shows an example view of the GUI of FIG. 29 that displays resource utilization within a hospital, where information may be viewed via a legend panel.
Figure 43:

GUI 2900 may include display elements such as information icon 2904 and settings icon 2906, which when selected may display panels with additional information or selectable options for further filtering the display. In some embodiments, selecting information icon 2904 or settings icon 2906 may trigger a display panel that slides in from one side, partially obscuring GUI 2900, as shown in FIGS. 34-36. Selecting information icon 2904 or settings icon 2906 may also trigger a display panel that pops up as a separate window, or any other type of display panel.

The data tiles included within GUI 2900 may include a suitable type of information display or visualization, including lists of hospital units and the resources or resource occupancy rates associated with that unit; lists of resources such as beds or ventilators and occupancy rates associated with the resources; charts or graphs showing resource allocation, patient activity, projected activity, or any other data that may be displayed via charts or graphs; patient load information broken down and listed by category; and so forth. It should be appreciated that the examples provided herein are for illustrative purposes and should not be construed as limiting in any way. Further, data tile formats may evolve over time, with new types of visualizations being incorporated into GUI 2900. Future embodiments may include new visualization techniques, video, animation, etc.

For example, in FIG. 29, GUI 2900 shows four data tiles displayed on the screen: patient load data tile 2908, CC/CV (ICU, Cardiovascular Unit) targeted bed status tile 2918, patient activity tile 2914, and environmental services (EVS) tile 2924. Patient load data tile 2908 may include a list of hospital units 2912, along with their location, number of patients in test, number of patients under investigation, number of patients who have tested positive for COVID-19, and number of ventilators, as indicated by header row 2910. Patient load data tile 2908 may be used by a hospital administrator to determine where patients with COVID-19 are located, how many have been tested, how many ventilators have been allocated to a given hospital unit, and so forth. Similarly, CC/CV targeted bed status tile 2918 may include a list of hospital units with CC/CV targeted beds, with an indication of how many are in use, how many are available, whether patients have an order to step down, transfer, or discharge (e.g., criteria not met), number ventilators, and number of beds blocked. In contrast, patient activity tile 2914 shows patient activity chart 2916, which may indicate for a given range of dates how many new COVID-19 patients have been confirmed, as well as how many tests have been ordered. As shown in patient activity chart 2916, a date range may extend into the future, and projected numbers of new COVID-19 patients and/or projected numbers of tests ordered may also be displayed.

Data tiles may also include graphical elements (e.g., icons) to indicate urgency, availability, warnings, etc. For example, EVS tile 2924 displays a list of CC/CV targeted beds, where the top two rows display stat icon 2930, indicating high priority. Additional icon such as bucket icon 2932, bed in use icon 2936, and broom icon 2938 may also be used to indicate that a bed requires cleaning, is being cleaned, or is occupied, respectively. An indication such as highlight box 2940 may indicate bed matches for potential boarding patients who have not yet been assigned a bed.

Figure 31:
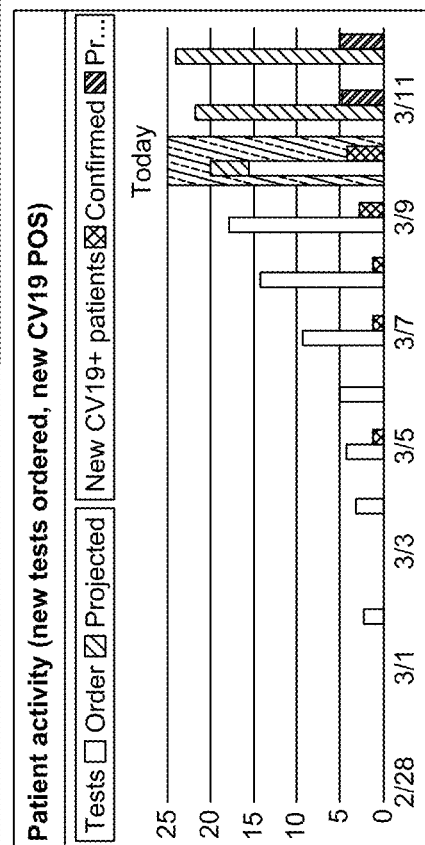

In some embodiments, elements displayed within GUI 2900 may be selected in order to reveal further information relevant to the element (e.g., data point). FIGS. 30-32 show example views of GUI 2900 in which additional data is displayed via a pop-up display panel when an input device such as a mouse hovers over a certain display element. FIG. 30 shows example view 3000 of GUI 2900, where a user is hovering over alert 3004, which triggers display panel 3002 with additional information relevant to alert 3004. For example, pop-up display panel 3002 may include a header explaining what the alert represents, for example, that 4 patients have tested positive for COVID-19 in unit 10 East of Lakeside Hospital. Pop-up display panel 3002 may include information such as a list of the patients who have tested positive for COVID-19 in Lakeside hospital's unit 10 East, the beds the patients have been assigned to, and the amount of time that the beds have been occupied. Further, pop-up display panel 3002 may include links to additional data, for example by displaying icon such as icon 3006 or hypertext links such as hypertext link 3008, which when selected may trigger the appearance of additional display panels.

GUI 2900 may also allow users to turn alerts on or off, such as when patients are transferred into or out of a given unit. FIG. 31 shows an example view 3100 of GUI 2900, in which the display of pop-up confirmation box 3102 has been triggered, for example, by selecting an alert such as alert 3004 in FIG. 30, prompting a user to confirm the removal of the alert. Additionally, GUI 2900 may display information relating to charts or graphs and pop-up display panels. FIG. 32 shows an example view 3200 of GUI 2900, in which a chart showing the number of tests ordered and confirmed cases of COVID-19 over time is displayed in data tile 3202. Pop-up display panel 3204 may be displayed when the user hovers over bar chart column 3206, in order to indicate the number of tests ordered and/or positive test results obtained for COVID-19 on the day indicated by bar chart column 3206. For example, in FIG. 32, pop-up display panel 3204 indicates that 42 tests were ordered, 10 of which resulted positive for COVID-19.

FIG. 33 shows an example view 3300 of GUI 2900 in which resource availability data is displayed for a system of hospitals, as indicated by scope indicator 2902. For example, a user may have selected the option "System" in a drop-down menu with options that included one or more individual hospitals, in order to view resource availability data that has been aggregated over a plurality of hospitals. Example view 3300 shows two vertically aligned data tiles, current total data tile 3302 showing total COVID-19 patient accounts across the hospital system, and patient activity tile 3304 showing the number of new tests ordered and number of tests resulting positive for COVID-19. As discussed earlier, the date range in this example extends into the future, showing projected numbers of new COVID-19 patients and/or projected numbers of tests ordered over the next two days.

FIG. 34 shows an example view 3400 of GUI 2900 in which settings icon 2906 from FIG. 29 has been selected in order to display a settings panel such as settings panel 3402. In an embodiment, settings panel 3402 comprises various display and control elements that allow a user to customize the dashboard displayed via GUI 2900. Settings panel 3402 may expand or slide out from the right side of GUI 2900, partially obscuring the dashboard displayed via GUI 2900. Settings panel 3402 may also include a control element to close the panel, such as panel close element 3404 indicated with an X, the selection of which may cause the control panel to disappear and reveal the full dashboard displayed via GUI 2900. Settings panel 3402 may also include common control elements such as save button 3406, reset button 3408, cancel button 3410, and/or apply button 3412.

Settings panel 3402 may comprise various sections with different control or display elements. In an embodiment, settings panel 3402 may include an interactive control element to select a facility from a pre-populated list of facilities, which may be displayed via a drop-down menu, radio buttons, checkboxes, or any other similar control element for selecting options from a list; options for turning auto scrolling on or off and/or setting an auto scroll interval; and/or a control element for selecting one or more categories of information to display as tiles within GUI 2900, as explained above in FIG. 29. For example, settings panel 3402 shows that four categories of information have been selected to be displayed as tiles arranged in a quadrant as shown in FIG. 29: patient load tile 3416, daily patient count tile 3418, critical care and NP beds tile 3420, and EDS for CC plus NP tile 3422.

Settings panel 3402 may also include control elements that permit a user to interactively define criteria for sorting, ordering, or filtering the data displayed in individual tiles within GUI 2900. The sorting, ordering, or filtering control elements may include drop-down menus, radio buttons, checkboxes, or similar interactive controls that allow a user to specify one or more sorting criteria from a selection of options. For example, a user who wishes to sort the data displayed in rows of a tile displayed in GUI 2900 in descending order from top to bottom by the total number of beds may select the corresponding item in a drop-down menu populated with sorting options, and/or "Descending" in a drop-down menu populated with options for sort order (e.g., ascending or descending). An indication of any currently defined sorting criteria may also be displayed within settings panel 3402. Similarly, GUI 2900 may include control elements for filtering the resource information displayed in rows of a tile, such as filter selectors, logical operator buttons, add filter and remove filter buttons, filter parameter lists, etc.

As an example of the customization options offered by settings panel 3402 in FIG. 34 discussed above, FIG. 35 shows an example view 3500 of GUI 2900 in which a user has selected three categories of information to be displayed as tiles within GUI 2900: ventilators ordered tile 3504, ventilators not used tile 3506, and orders to discontinue ventilator use 3508. Thus, a hospital administrator may be able to visualize all the information they need relevant to the assignment or allocation of ventilators within a hospital in one single dashboard.

FIG. 36 shows an example view 3600 of GUI 2900 in which information icon 2904 from FIG. 29 has been selected in order to display a legend panel such as legend panel 3602. Legend panel 3602 may indicate how different icons displayed in GUI 2900 may be interpreted. In an embodiment, legend panel 3602 may be divided into sections corresponding to different types of icons, within which the interpretations of various icons are displayed next to each icon. For example, legend panel 3602 may include an alerts section that indicates what an amber alert icon or red alert icon should be interpreted as; an environmental services (EVS) status section that indicates what icons are used to indicate what stage of cleaning or preparation a bed is in; and/or a bed status section that indicates what icons are used to indicate whether or not a bed has been assigned, and so forth. It should be appreciated that the elements, sections, and icons mentioned herein are for illustrative purposes and should not be construed as limiting.

FIGS. 37-44 show an alternative embodiment of a national capacity GUI (e.g., an alternative embodiment of GUI 2200 of FIGS. 22-28). The national capacity GUI shown in FIGS. 37-44 may be similar to GUI 2200, but may include a different title (e.g., National Capacity rather than Super Capacity), the bed availability alert may have a different visual appearance (from triangle to circle), the filter icon is moved from the NY row to the Total row, expanded sections of the settings panel are shown, and, as shown in FIG. 44, a pop-up filter display panel may be displayed in response to a user hovering over the filter icon, where the filter display panel includes the filter that has been applied (herein, the alert level of critical, bed available) and illustrates how many facilities are shown and how many facilities are filtered out, with the option to clear the filter.

The systems, methods, and graphical user interfaces provided herein may improve the accuracy of healthcare resource allocation, sharing, and acquisition during high-demand situations where time is limited, such as during infectious disease outbreaks where patient demand of resources may change exponentially and data obtained one day may not be applicable the next day. The time it would take to individually collect data from multiple hospitals (particularly hospitals that do not typically share data), aggregate and analyze the collected data, and visualize the data using standard methods could render the data useless by the time the data was visualized, because resource utilization may change so rapidly. By establishing a system that automatically receives data from all hospitals in real time or near real time, aggregates that information regardless of data format, and continually updates resource availability dashboards as data is received, where the dashboards can be rendered as the GUIs described herein, the approach of the disclosure allows healthcare administrators to make informed decisions about critical healthcare questions, such as when to transfer patients and where to transfer the patients, when to request new resources (e.g., from a state or national stockpile, or from other hospitals), and when to offer to share resources, thereby improving patient care.

In contrast, in prior systems when a healthcare administrator or other authority attempted to request additional resources, transfer patients or accept transferred patients, or offer to share unused resources with another medical facility, errors could be made due to delays in updating resource availability information across multiple units, facilities, and regions. For example, new resources requested by an administrator may not actually be needed by the time the request is entered and executed, due to hospital resource usage having changed without the changes being propagated to the administrator in a timely fashion, or offers by an administrator to share resources may pose issues if those resources are not available due to the hospital's resource demands having changed before the request was entered and executed. The described resource utilization system/GUIs solves this problem by providing a specific, dynamically updating list of critical resources across facility units, facilities, hospital networks, regions, and nationwide. In this way, the resource availability system and generated GUIs provides an improvement to the capability of the healthcare system as a whole. The disclosure provides a specific way of improving the capability of the healthcare system, by providing one or more resource availability GUIs that display dynamically updating critical resource availability lists. The disclosure further provides a specific improvement to the way computers operate by aggregating critical resource availability information for multiple separate facilities in one location and updating the critical resource availability information in real-time, which may obviate the need for users to have to navigate through multiple different data files, manually update information as availability changes, and so forth, thereby increasing the efficiency of the operation of the computer for the user.

Further, hospitals may not be configured to share critical resource data in real-time, even across different units of the hospital. Thus, prior methods of resource availability determination demanded manual collection of data (e.g., visually inspecting each room for bed occupancy and ventilator usage) and aggregation in a spreadsheet or other document, with updates also made manually. Systems were not available to automatically pull data from multiple units and multiple facilities and then aggregate the pulled data into a visually clear format where healthcare decisions can be quickly made just by glancing at a GUI, as described in the embodiments herein. Additionally, different facilities may have different data sharing agreements and the need to comply with HIPAA/patient information sharing laws means that different facilities may provide data in different formats (e.g., HL7 messages versus flat files) and prior systems were unable to automatically aggregate these different formats into a single set of dashboards that can be visualized via GUIs, with the dashboards automatically updated each time new data is received, as described herein.

The resource availability GUIs described herein provide a specific manner of displaying a limited set of information to a user (critical resource availability information), rather than using conventional user interface methods to display a generic index on a computer, requiring the user to step through many layers of menu options to reach the desired data, or burying the desired data within all hospital data. Thus, the user experience with the computer may be improved and made more efficient.

Furthermore, by displaying a limited set of information via the resource availability GUIs as described herein, operation of the computing device(s) that collect and render the data for display may be improved by reducing the processing demands of the computing device(s), thereby increasing the efficiency of the computing device(s). For example, only certain critical resource availability and allocation information may be displayed, which results in a limited amount of the data that is received being processed, which may improve the efficiency of the computing device(s). Further, because the data is processed in real time and updates to the resource availability GUIs are made continuously as data is received, undue processing lags that may occur if updates were made at predefined discrete time points may be reduced, which may improve the efficiency of the computing device(s).

The embodiments described herein may allow for the retrieval/receipt of various types of data from disparate locations and systems (e.g., different hospitals, hospital networks, etc.) and processing of the data to populate the resource availability GUIs as described herein in real time or near real time. The systems described herein may be configured to continue to update the resource availability GUIs even if a hospital or network experiences a lag in data collection or reporting, or if data is otherwise unexpectedly unavailable from a given institution for a period of time. For example, data from other institutions may continue to be reported even if data from other institutions is not available. Further, in some examples, the systems described herein may use prior data from a given institution to project resource availability and report the projected resource availability via the resource availability GUIs when current resource availability data is not available for that institution. In doing so, real time reporting of data may be maintained.

The resource utilization server, included as part of a collaborative resource utilization system as described herein, may provide for high speed data processing that allows for the real-time or near real-time updates to the different resource availability GUIs. For example, the resource utilization server may be configured to update the critical resource GUIs every 30 seconds, rather than every 15 minutes or longer as in some prior systems. To accomplish this, the resource utilization server may be configured with parsers that send data reception acknowledgments (e.g., HL7 acknowledgements) before processing of received packets/messages and may inspect/reject the packets/messages before processing.

Further, the resource utilization server may be configured to derive hospital composition information (e.g., bed inventory, ventilator usage information) by pulling data from the EMR and/or by deriving the composition information from the messages/packets that the resource utilization server sends and receives. For example, the messages may ask for specific information (e.g., bed inventory), and the resource utilization server may calculate the composition information from the responses, e.g., by combing through the data/messages to pull the information. This approach may avoid the need for an upstream user or system (e.g., at the hospital) to fill out a form (such as a bed master form) and send updates, which may allow for faster retrieval of the information.

The technical effect of presenting hospital resource utilization information for a system of hospitals via a GUI as described herein is that hospital administrators and/or health care providers may quickly make decisions about resource sharing/reallocation, new equipment orders, transfer of patients, etc., so that patient care may be improved. Further, the simplicity of use, intuitiveness, and scalability facilitates rapid deployment across hospital networks of any size.

An embodiment of a method is provided, including receiving first data from a first medical facility, the first data received via a first data streaming process and/or in a first format; receiving second data from a second medical facility, the second data received via a second data streaming process and/or in a second format; processing the first data and the second data to generate one or more resource availability graphical user interfaces (GUIs); and outputting the one or more resource availability GUIs for display on a display device. In a first example of the method, the first data is received in HL7 message format via HTTPS/TCP from the first medical facility. In a second example of the method, which optionally includes the first example, the second data is received in one or more flat files via SFTP from the second medical facility. In a third example of the method, which optionally includes one or both of the first and second examples, the first data and the second data are each processed to determine a per-unit bed occupancy rate for the first medical facility and a per-unit bed occupancy rate for the second medical facility, respectively. In a fourth example of the method, which optionally includes one or more or each of the first through third examples, the first data and the second data are each processed to determine a count of occupied beds, a count of blocked beds, a count of unoccupied beds, and a count of negative pressure beds for each unit of the first medical facility and each unit of the second medical facility. In a fifth example of the method, which optionally includes one or more or each of the first through fourth examples, the first data and the second data are each processed to determine a medical device count for the first medical facility and a medical device count for the second medical facility, respectively. In a sixth example of the method, which optionally includes one or more or each of the first through fifth examples, the first data is received and processed in real-time, and wherein the second data is received and processed in near real-time. In a seventh example of the method, which optionally includes one or more or each of the first through sixth examples, the first medical facility is one of a plurality of first medical facilities configured to send first data in the first format and wherein the second medical facility is one of a plurality of second medical facilities configured to send second data in the second format. In an eighth example of the method, which optionally includes one or more or each of the first through seventh examples, the first data from each first medical facility and the second data from each second medical facility are processed to generate the one or more resource availability GUIs. In a ninth example of the method, which optionally includes one or more or each of the first through eighth examples, the one or more resource availability GUIs include a first resource availability GUI configured to display resource availability in a hospital network at a national level, a regional level, and a facility level. In a tenth example of the method, which optionally includes one or more or each of the first through ninth examples, the one or more resource availability GUIs include a second resource availability GUI configured to display resource availability across multiple hospital networks and/or multiple individual hospitals at a national level, a regional level, and a facility level. In an eleventh example of the method, which optionally includes one or more or each of the first through tenth examples, the one or more resource availability GUIs include a third resource availability GUI configured to display resource availability and patient load for a particular disease across one or more hospitals. In a twelfth example of the method, which optionally includes one or more or each of the first through eleventh examples, the particular disease is COVID-19, and wherein the third resource availability GUI is configured to display a count of patients undergoing COVID-19 testing, a count of patients determined to be positive for COVID-19, and a count of patients determined to be still under investigation for COVID-19. In a thirteenth example of the method, which optionally includes one or more or each of the first through twelfth examples, the particular disease is COVID-19, and wherein the third resource availability GUI is configured to display a graph showing past, current, and predicted numbers of COVID-19 tests ordered and past, current, and predicted numbers of new COVID-19 patients. In a fourteenth example of the method, which optionally includes one or more or each of the first through thirteenth examples, the one or more resource availability GUIs are configured to display a resource availability alert in response to determining, based on the first data and/or second data, that a resource availability has dropped below a threshold level.

An embodiment of a system includes a display; and a computing device operably coupled to the display and storing instructions executable to: output, to the display, a graphical user interface (GUI) including one or more of a per-unit bed count, a medical device utilization count, and a disease count for each of a plurality of medical facilities, the one or more of the per-unit bed count, medical device utilization count, and disease count determined based on data sent from each of the plurality of medical facilities, where the data includes data sent in a first format from a first medical facility and data sent in a second format from a second medical facility. In a first example of the system, the per-unit bed count includes a per-unit bed occupancy rate and the GUI is configured to display a graphical representation of each per-unit bed occupancy rate, each graphical representation configured to change in visual appearance if a corresponding bed occupancy rate increases above a threshold rate. In a second example of the system, which optionally includes the first example, the medical device utilization count includes a ventilator occupancy rate and the GUI is configured to display a graphical representation of each ventilator occupancy rate, each graphical representation configured to change in visual appearance if a corresponding ventilator occupancy rate increases above a threshold rate. In a third example of the system, which optionally includes one or both of the first and second examples, the first format includes HL7 messages and the second format includes flat files. In a fourth example of the system, which optionally includes one or more or each of the first through third examples, the instructions are executable to update one or more of the per-unit bed count, the medical device utilization count, and the disease count as the data sent from each of the plurality of medical facilities changes.

An embodiment of a method includes determining, based on one or more test results of one or more tests for a disease included in a data stream from a medical facility and further based on an amount of time since the one or more tests were conducted, whether a patient suspected of having the disease is positive, negative, or under investigation for the disease; and updating one or more resource availability graphical user interfaces (GUIs) based on the determination. In a first example of the method, the determining includes: if the patient has a negative test result for a current test without a prior positive test result, indicating that the patient is negative for the disease responsive to a first threshold amount of time having elapsed since the current test was performed, otherwise indicating the patient is under investigation. In a second example of the method, which optionally includes one or both of the first and second examples, the determining includes: if the patient has an inconclusive test result for a current test without a prior positive test result, indicating the patient is under investigation until a negative test result is received or until the first threshold amount of time has elapsed since the current test was performed, and then indicating the patient is negative. In a fourth example of the method, which optionally includes one or more or each of the first through third examples, the determining includes if the patient has at least one prior positive test result, indicating the patient is positive for the disease until: a) a second threshold amount of time has elapsed since a first negative test result following the prior positive test result; or b) two negative test results are received following the prior positive test result, the two negative tests carried out with at least a third threshold amount of time between the tests. In a fifth example of the method, which optionally includes one or more or each of the first through fourth examples, updating the one or more resource availability GUIs includes removing the patient from a positive count or a person under investigation count responsive to indicating the patient is negative; adding the patient to the positive count responsive to indicating the patient is positive; and adding the patient to the person under investigation count responsive to indicating the patient is under investigation. In a sixth example of the method, which optionally includes one or more or each of the first through fifth examples, the one or more resource availability GUIs includes a first resource availability GUI where the positive count and the person under investigation count are displayed for each of a plurality of census regions. In a seventh example of the method, which optionally includes one or more or each of the first through sixth examples, the first resource availability GUI is configured to display the positive count and the person under investigation count by state and/or hospital in response to a user request. In an eighth example of the method, which optionally includes one or more or each of the first through seventh examples, the first resource availability GUI is configured to display a per-unit bed count and/or bed utilization rate and a medical device utilization count and/or medical device utilization rate for each of a plurality of census regions. In a ninth example of the method, which optionally includes one or more or each of the first through eighth examples, the first resource availability GUI is configured to display the per-unit bed count and/or bed utilization rate and the medical device utilization count and/or the medical device utilization rate by state and/or hospital in response to a user request. In a tenth example of the method, which optionally includes one or more or each of the first through ninth examples, the first resource utilization dashboard is configured to display an alert responsive to a per-unit bed utilization rate or a medical device utilization rate exceeding a respective threshold. In an eleventh example of the method, which optionally includes one or more or each of the first through tenth examples, updating the one or more resource availability GUIs includes, responsive to indicating the patient is positive, adding the patient as a newly diagnosed patient to a bar graph showing past, current, and/or predicted numbers of disease tests ordered and past, current, and/or predicted numbers of newly diagnosed patients. In a twelfth example of the method, which optionally includes one or more or each of the first through eleventh examples, each of the first threshold amount of time, the second threshold amount of time, and the third threshold amount of time are updated based on government agency guidelines. In a thirteenth example of the method, which optionally includes one or more or each of the first through twelfth examples, each of the first threshold amount of time, the second threshold amount of time, and the third threshold amount of time are user-configurable.

Another embodiment of a method includes receiving, from a data stream from a medical facility, a positive test result for a patient suspected to have a disease, and updating one or more resource availability graphical user interfaces (GUIs) to include the patient in a disease-positive count; and if a negative test result for the patient is received in the data stream from the medical facility after the positive test result, updating the one or more resource availability GUIs to remove the patient from the disease-positive count only if a first threshold amount of time has elapsed since the negative test result was received or if the negative test result is a second negative test result following a first negative result, where the second negative test result follows the first negative result by at least a second threshold amount of time. In a first example of the method, the one or more resource availability GUIs include a first resource availability GUI configured to display resource availability in a hospital network at a national level, a regional level, and a facility level. In a second example of the method, which optionally includes the first example, the one or more resource availability GUIs include a second resource availability GUI configured to display resource availability across multiple hospital networks and/or multiple individual hospitals at a national level, a regional level, and a facility level. In a third example of the method, which optionally includes one or both of the first and second examples, the one or more resource availability GUIs include a third resource availability GUI configured to display resource availability and the disease-positive count across one or more hospitals. In a fourth example of the method, which optionally includes one or more or each of the first through third examples, the disease is COVID-19, and wherein the third resource availability GUI is further configured to display a person under investigation count for patients determined to be still under investigation for COVID-19. In a fifth example of the method, which optionally includes one or more or each of the first through fourth examples, the one or more resource availability GUIs are configured to display a resource availability alert in response to determining, that a resource availability has dropped below a threshold level.

An embodiment of a system includes a display; and a computing device operably coupled to the display and storing instructions executable to: output, to the display, a graphical user interface including a positive count for a disease and a person under investigation count for the disease displayed for each of a plurality of census regions, states, hospital networks, hospitals, and/or hospital units; receive, from a plurality of data streams from a plurality of medical facilities, a plurality of test results for the disease; and update the positive count responsive to one of the plurality of test results being a negative test result for a patient counted in the positive count, only if a first threshold amount of time has elapsed since the negative test result was received or if the negative test result is a second negative test result following a first negative result, where the second negative test result follows the first negative result by at least a second threshold amount of time.

An embodiment of a method includes receiving real-time data associated with a plurality of ventilators; determining, for each ventilator of the plurality of ventilators, a ventilator status based on one or more of a ventilation start time, a ventilation stop time, a ventilator type, and a ventilator location, the one or more of the ventilation start time, the ventilation stop time, the ventilator type, and the ventilator location determined from the real-time data; and updating one or more resource availability graphical user interfaces (GUIs) based on the ventilator status. In a first example of the method, determining the ventilator status comprises determining: a) if a ventilation start time has been indicated; b) if a ventilation stop time has not been indicated; c) if a ventilation start time has been indicated after a ventilation stop time; and d) if the ventilator is an invasive ventilator; and if, for a respective ventilator, a), d), and one of b) or c) are true, indicating the ventilator status is in use and that the ventilator is an invasive ventilator. In a second example of the method, which optionally includes the first example, receiving real-time data associated with a plurality of ventilators comprises receiving the real-time data from the plurality of ventilators or from one or more electronic medical record databases and wherein updating the one or more resource availability GUIs based on the ventilator status comprises updating a ventilator occupancy rate displayed on the one or more resource availability GUIs. In a third example of the method, which optionally includes one or both of the first and second examples, the method further includes displaying, via the one or more resource availability GUIs, a graphical representation of the ventilator occupancy rate, the graphical representation configured to change in visual appearance in response to the ventilator occupancy rate increasing above a threshold rate. In a fourth example of the method, which optionally includes one or more or each of the first through third examples, receiving real-time data associated with a plurality of ventilators comprises receiving real-time data from a plurality of ventilators located at a plurality of different medical facilities. In a fifth example of the method, which optionally includes one or more or each of the first through fourth examples, receiving real-time data associated with a plurality of ventilators comprises receiving HL7 messages. In a sixth example of the method, which optionally includes one or more or each of the first through fifth examples, the one or more resource availability GUIs include a first resource availability GUI configured to display resource availability in a hospital network at a national level, a regional level, and a facility level. In a seventh example of the method, which optionally includes one or more or each of the first through sixth examples, the one or more resource availability GUIs include a second resource availability GUI configured to display resource availability across multiple hospital networks and/or multiple individual hospitals at a national level, a regional level, and a facility level. In an eighth example of the method, which optionally includes one or more or each of the first through seventh examples, the one or more resource availability GUIs include a third resource availability GUI configured to display resource availability and patient load for a particular disease across one or more hospitals. In a ninth example of the method, which optionally includes one or more or each of the first through eighth examples, the particular disease is COVID-19, and wherein the third resource availability GUI is configured to display a count of patients undergoing COVID-19 testing, a count of patients determined to be positive for COVID-19, and a count of patients determined to be still under investigation for COVID-19. In a tenth example of the method, which optionally includes one or more or each of the first through ninth examples, the resource availability includes a ventilators in use count and/or a ventilator occupancy rate, each updated based on the ventilator status, and further includes a count of occupied beds, a count of blocked beds, a count of unoccupied beds, and a count of negative pressure beds for each unit of a plurality of medical facilities.

An embodiment of a system includes a display; and a computing device operably coupled to the display and storing instructions executable to: receive real-time data associated with a plurality of ventilators; determine, for each ventilator of the plurality of ventilators, based on the real-time data whether that ventilator is currently in use; output, to the display, a graphical user interface (GUI) including a respective ventilator occupancy rate for a hospital unit, a hospital, a hospital network, a state, a region, and/or a nation, each ventilator occupancy rate determined based on a number of ventilators determined to currently be in use and a location of each ventilator. In a first example of the system, to determine if a ventilator is currently in use, the instructions are executable to determine: a) if a ventilation start time for that ventilator has been indicated; b) if a ventilation stop time for that ventilator has not been indicated; and c) if a ventilation start time for that ventilator has been indicated after a ventilation stop time; and wherein the instructions are further executable to determine that the ventilator is currently in use if a) and one of b) or c) are true. In a second example of the system, which optionally includes the first example, the instructions are executable to determine a location of each ventilator based on the real-time data. In a third example of the system, which optionally includes one or both of the first and second examples, the instructions are executable to update each respective ventilator occupancy rate in real-time as the real-time data is received. In a fourth example of the system, which optionally includes one or more or each of the first through third examples, the GUI further includes a respective bed occupancy rate for one or more hospital units, one or more hospitals, one or more hospital networks, one or more states, one or more regions, and/or one or more nations. In a fifth example of the system, which optionally includes one or more or each of the first through fourth examples, the GUI is configured to display a resource availability alert in response to determining that the ventilator occupancy rate and/or a bed occupancy rate is above a respective threshold level.

An embodiment of a method includes receiving real-time data associated with a plurality of ventilators; determining, for each ventilator of the plurality of ventilators and based on the real-time data, whether that ventilator is currently in use in a defined geographical area; and output, to the display, a graphical user interface (GUI) including a ventilator occupancy rate for the defined geographical area, the ventilator occupancy rate for the defined geographical region determined based on whether or not each ventilator is currently in use in the defined geographical area. In a first example of the method, the determining includes determining for each ventilator: a) if a ventilation start time has been indicated; b) if a ventilation stop time has not been indicated; c) if a ventilation start time has been indicated after a ventilation stop time; and d) if the ventilator is located in the defined geographical area; and if, for a respective ventilator, a), d), and one of b) or c) are true, the method includes indicating that the ventilator is currently in use in the defined geographical area. In a second example of the method, which optionally includes the first example, the method further includes displaying, via the GUI, a graphical representation of the ventilator occupancy rate, the graphical representation configured to change in visual appearance in response to the ventilator occupancy rate increasing above a threshold rate.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first,"

"second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for a resource utilization server, comprising:
   receiving, at the resource utilization server, first data from at least a first medical facility and a second medical facility, the first data received via a first data streaming process and in a first format;
   receiving, at the resource utilization server, second data from at least the first medical facility and the second medical facility, the second data received via a second data streaming process and in a second format;
   sending, with parsers of the resource utilization server, data reception acknowledgments acknowledging reception of the first data for high speed data processing;
   inspecting, with parsers of the resource utilization server, the received data;
   processing, with the resource utilization server, the first data and the second data in real or near real-time to generate a resource availability graphical user interface (GUI) displaying a plurality of aggregated resource availability metrics of a hospital network at a national level, the hospital network including at least the first medical facility and the second medical facility and the plurality of aggregated resource availability metrics determined at least in part based on the first data and the second data, wherein each aggregated resource availability metric is displayed in a plurality of display areas of the resource availability GUI, each display area corresponding to a different national region;
   automatically updating, with the resource utilization server, the resource availability GUI each time additional first data and/or additional second data is received;
   outputting the resource availability GUI for display on a display device; and
   receiving user input to a tab of the resource availability GUI associated with a first national region, and in response, adjusting the resource availability GUI to show resource availability metrics for medical facilities in only the first national region and outputting the adjusted resource availability GUI for display on the display device.

2. The method of claim 1, wherein the first data is received in a first message format via secure channels from at least the first medical facility and the second medical facility and the second data is received in a second message format via secure channels from at least the first medical facility and the second medical facility, and wherein at least some of the first data and/or second data is stored in encrypted form at the first medical facility and the second medical facility.

3. The method of claim 2, wherein the first data is received in a healthcare message format via hypertext transfer protocol secure (HTTPS) from at least the first medical facility and the second medical facility, and wherein the second data is received in one or more flat files via secure file transfer protocol (SFTP) from at least the first medical facility and the second medical facility.

4. The method of claim 1, further comprising determining a per-unit bed occupancy rate for the first medical facility and a per-unit bed occupancy rate for the second medical facility based on the first data and the second data, and wherein the plurality of aggregated resource availability metrics of the resource availability GUI includes a per-unit bed occupancy rate for each national region determined at least based on the per-unit bed occupancy rate for the first medical facility and the per-unit bed occupancy rate for the second medical facility.

5. The method of claim 1, further comprising determining a count of occupied beds, a count of blocked beds, a count of unoccupied beds, and a count of negative pressure beds for each unit of the first medical facility and each unit of the second medical facility based on the first data and the second data.

6. The method of claim 1, further comprising determining a medical device count for the first medical facility and a medical device count for the second medical facility based on the first data and the second data, and wherein the plurality of aggregated resource availability metrics of the resource availability GUI includes a medical device count for each national region determined at least based on the medical device count for the first medical facility and the medical device count for the second medical facility.

7. The method of claim 4, wherein the resource availability metrics of the adjusted resource availability GUI include a per-unit bed occupancy rate for each medical facility in the first national region, including the per-unit bed occupancy rate for the first medical facility and the per-unit bed occupancy rate for the second medical facility.

8. The method of claim 3, wherein the first data comprises admissions, discharge, and transfer data, order entry data, and observation data, and the second data comprises bed occupancy data.

9. The method of claim 8, wherein the first data is filtered prior to being received at the resource utilization server.

10. The method of claim 1, further comprising processing, with the resource utilization server, the first data and the second data to generate a second resource availability GUI configured to display resource availability across multiple hospital networks and/or multiple individual hospitals at a national level, a regional level, and/or a facility level.

11. The method of claim 1, further comprising processing, with the resource utilization server, the first data and the second data to generate a third resource availability GUI configured to display resource availability and patient load for a particular disease across one or more hospitals.

12. The method of claim 11, wherein the particular disease is COVID-19, and wherein the third resource availability GUI is configured to display a count of patients undergoing COVID-19 testing, a count of patients determined to be positive for COVID-19, and a count of patients determined to be still under investigation for COVID-19.

13. The method of claim 11, wherein the particular disease is COVID-19, and wherein the third resource availability GUI is configured to display a graph showing past, current, and predicted numbers of COVID-19 tests ordered and past, current, and predicted numbers of new COVID-19 patients.

14. The method of claim 1, wherein the resource availability GUI is configured to display a resource availability alert in response to determining, based on the first data and/or second data, that an aggregated resource availability metric has dropped below a threshold level.

15. A system, comprising:
a display; and
a computing device operably coupled to the display and storing instructions executable to:
determine a per-unit bed count, a medical device utilization count, and a disease count for each of a plurality of national regions, the per-unit bed count, medical device utilization count, and disease count determined based on data from each of a plurality of medical facilities of the plurality of national regions, wherein the data includes data in a first format from a first medical facility of the plurality of medical facilities and data in a second format from a second medical facility of the plurality of medical facilities, and wherein the data includes hospital composition data obtained by pulling the hospital composition data from one or more electronic medical record (EMR) databases of one or more medical facilities of the plurality of medical facilities and/or by deriving the hospital composition information from messages or packets that the computing device sends and receives, wherein the data in the first format is received in a first message format via secure channels from the first medical facility and the data in the second format is received in a second message format via secure channels from the second medical facility, wherein the EMR database is configured to store data in encrypted form;
send, with parsers of the system, data reception acknowledgements prior to determining the per-unit bed count, the medical device utilization count, and the disease count for reach of a plurality of national regions, in real or near-real time for high speed data processing;
inspect, with parsers of the resource utilization server, the received data prior to determining the per-unit bed count, the medical device utilization count, and the disease count for each of a plurality of national regions;
output, to the display, a graphical user interface (GUI) including the per-unit bed count, the medical device utilization count, and the disease count for each of the plurality of national regions; and
responsive to receiving a user input selecting a first national region of the plurality of national regions, adjust the GUI to show an expanded version of the first national region that includes each of a per-unit bed count, a medical device utilization count, and a disease count for each state and/or medical facility included in the first national region.

16. The system of claim 15, wherein each per-unit bed count includes a per-unit bed occupancy rate and the GUI is configured to display a graphical representation of each per-unit bed occupancy rate, each graphical representation configured to change in visual appearance if a corresponding bed occupancy rate increases above a threshold rate, and wherein the hospital composition data includes bed inventory data.

17. The system of claim 15, wherein the medical device utilization count includes a ventilator occupancy rate and the GUI is configured to display a graphical representation of each ventilator occupancy rate, each graphical representation configured to change in visual appearance if a corresponding ventilator occupancy rate increases above a threshold rate, and wherein the hospital composition data includes ventilator usage data.

18. The system of claim 15, wherein the first format includes messages in a healthcare message format and the second format includes flat files, and wherein the instructions are executable to update one or more of the per-unit bed count, the medical device utilization count, and the disease count as the data sent from each of the plurality of medical facilities changes.

19. A system, comprising:
a display; and
a computing device operably coupled to the display and storing instructions executable to:
receive, at the resource utilization server, first data from at least a first medical facility and a second medical facility, the first data received via a first data streaming process and in a first format;
receive, at the resource utilization server, second data from at least the first medical facility and the second medical facility, the second data received via a second data streaming process and in a second format;
send, with parsers of the resource utilization server, data reception acknowledgments acknowledging reception of the first data for high speed data processing;
inspect, with parsers of the resource utilization server, the received data;
process, with the resource utilization server, the first data and the second data in real or near real-time to generate a resource availability graphical user interface (GUI) displaying a plurality of aggregated resource availability metrics of a hospital network at a national level, the hospital network including at least the first medical facility and the second medical facility and the plurality of aggregated resource availability metrics determined at least in part based on the first data and the second data, wherein each aggregated resource availability metric is displayed in a plurality of display areas of the resource availability GUI, each display area corresponding to a different national region;
automatically update, with the resource utilization server, the resource availability GUI each time additional first data and/or additional second data is received;
output the resource availability GUI for display on a display device; and
responsive to receiving user input to a tab of the resource availability GUI associated with a first national region, and in response, adjust the resource availability GUI to show resource availability metrics for medical facilities in only the first national region and output the adjusted resource availability GUI for display on the display device.

* * * * *